United States Patent
Copeland et al.

(10) Patent No.: US 9,333,217 B2
(45) Date of Patent: *May 10, 2016

(54) INHIBITORS OF HUMAN EZH2, AND METHODS OF USE THEREOF

(71) Applicant: Epizyme, Inc., Cambridge, MA (US)

(72) Inventors: Robert A. Copeland, Lexington, MA (US); Victoria M. Richon, Wellesley, MA (US); Margaret D. Scott, Beverly, MA (US); Christopher J. Sneeringer, San Francisco, CA (US); Kevin W. Kuntz, Woburn, MA (US); Sarah K. Knutson, Cambridge, MA (US); Roy M. Pollock, Medford, MA (US)

(73) Assignee: Epizyme, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/540,977

(22) Filed: Nov. 13, 2014

(65) Prior Publication Data

US 2015/0141362 A1    May 21, 2015

Related U.S. Application Data

(63) Continuation of application No. 13/230,703, filed on Sep. 12, 2011, now Pat. No. 8,895,245.

(60) Provisional application No. 61/381,684, filed on Sep. 10, 2010.

(51) Int. Cl.
| | |
|---|---|
| *A61P 35/00* | (2006.01) |
| *C12Q 1/68* | (2006.01) |
| *A61K 31/7076* | (2006.01) |
| *C07D 473/34* | (2006.01) |
| *C12Q 1/48* | (2006.01) |
| *G01N 33/50* | (2006.01) |
| *G01N 33/574* | (2006.01) |
| *C07D 493/04* | (2006.01) |
| *A61P 35/02* | (2006.01) |

(52) U.S. Cl.
CPC .......... *A61K 31/7076* (2013.01); *C07D 473/34* (2013.01); *C07D 493/04* (2013.01); *C12Q 1/48* (2013.01); *C12Q 1/6876* (2013.01); *G01N 33/5011* (2013.01); *G01N 33/57426* (2013.01); *G01N 2333/91011* (2013.01)

(58) Field of Classification Search
None
See application file for complete search history.

(56) References Cited

U.S. PATENT DOCUMENTS

| | | | |
|---|---|---|---|
| 5,716,993 A | 2/1998 | Ozaki et al. | |
| 5,948,803 A | 9/1999 | Maeda et al. | |
| 6,689,583 B1 | 2/2004 | Jenuwein et al. | |
| 7,122,547 B1 | 10/2006 | Huth et al. | |
| 7,252,968 B2 | 8/2007 | Jenuwein et al. | |
| 7,442,685 B2 | 10/2008 | Zhang et al. | |
| 7,563,589 B2 | 7/2009 | Zhang et al. | |
| 7,923,219 B2 | 4/2011 | Wang et al. | |
| 8,691,507 B2 | 4/2014 | Copeland et al. | |
| 8,765,732 B2 | 7/2014 | Kuntz et al. | |
| 8,895,245 B2 | 11/2014 | Copeland et al. | |
| 2002/0183324 A1 | 12/2002 | Jacobson et al. | |
| 2004/0082619 A1 | 4/2004 | Tada et al. | |
| 2005/0059682 A1 | 3/2005 | Rubinfeld | |
| 2005/0266473 A1 | 12/2005 | Zhang et al. | |
| 2008/0182844 A1 | 7/2008 | Bjergarde et al. | |
| 2008/0222741 A1 | 9/2008 | Chinnaiyan | |
| 2008/0269289 A1 | 10/2008 | Frank et al. | |
| 2008/0312292 A1 | 12/2008 | Yasui et al. | |
| 2009/0012031 A1 | 1/2009 | Chinnaiyan et al. | |
| 2009/0012175 A1 | 1/2009 | Bacopoulos et al. | |
| 2009/0061443 A1 | 3/2009 | Zhang et al. | |
| 2009/0203057 A1 | 8/2009 | Zhang et al. | |
| 2010/0035912 A1 | 2/2010 | Debnath et al. | |
| 2010/0113415 A1 | 5/2010 | Rajapakse et al. | |
| 2011/0021362 A1 | 1/2011 | Trojer et al. | |
| 2013/0040906 A1 | 2/2013 | Kuntz et al. | |
| 2014/0275081 A1 | 9/2014 | Kuntz et al. | |

FOREIGN PATENT DOCUMENTS

| | | |
|---|---|---|
| CN | 1683526 A | 10/2005 |
| CN | 101365806 A | 2/2009 |
| EP | 1357111 A1 | 10/2003 |
| JP | 7033729 A | 2/1995 |
| KR | 20070029617 A | 3/2007 |

(Continued)

OTHER PUBLICATIONS

Barski et al. "High-Resolution Profiling of Histone Methylations in the Human Genome." *Cell.* 129.4(2007):823-837.

(Continued)

*Primary Examiner* — Nancy J Leith

(74) *Attorney, Agent, or Firm* — Cooley LLP; Ivor R. Elrifi; Heidi A. Erlacher

(57) ABSTRACT

The invention relates to inhibition of wild-type and certain mutant forms of human histone methyltransferase EZH2, the catalytic subunit of the PRC2 complex which catalyzes the mono- through tri-methylation of lysine 27 on histone H3 (H3-K27). In one embodiment the inhibition is selective for the mutant form of the EZH2, such that trimethylation of H3-K27, which is associated with certain cancers, is inhibited. The methods can be used to treat cancers including follicular lymphoma and diffuse large B-cell lymphoma (DL-BCL). Also provided are methods for identifying small molecule selective inhibitors of the mutant forms of EZH2 and also methods for determining responsiveness to an EZH2 inhibitor in a subject.

6 Claims, 14 Drawing Sheets

(56) References Cited

FOREIGN PATENT DOCUMENTS

| | | |
|---|---|---|
| WO | WO-9640100 A1 | 12/1996 |
| WO | WO-0018725 A1 | 4/2000 |
| WO | WO-03079788 A2 | 10/2003 |
| WO | WO-2005018578 A2 | 3/2005 |
| WO | WO-2006116713 A1 | 11/2006 |
| WO | WO-2007045462 A2 | 4/2007 |
| WO | WO-2007050347 A1 | 5/2007 |
| WO | WO-2007070818 A1 | 6/2007 |
| WO | WO-2007072225 A2 | 6/2007 |
| WO | WO-2007136592 A2 | 11/2007 |
| WO | WO-2008073138 A2 | 6/2008 |
| WO | WO-2008103277 A2 | 8/2008 |
| WO | WO-2008104077 A1 | 9/2008 |
| WO | WO-2008108825 A2 | 9/2008 |
| WO | WO-2008113006 A1 | 9/2008 |
| WO | WO-2009058298 A1 | 5/2009 |
| WO | WO-2009077766 A1 | 6/2009 |
| WO | WO-2009124137 A2 | 10/2009 |
| WO | WO-2010018328 A1 | 2/2010 |
| WO | WO-2010111653 A2 | 9/2010 |
| WO | WO-2011082044 A1 | 7/2011 |
| WO | WO-2011140324 A1 | 11/2011 |
| WO | WO-2011140325 A1 | 11/2011 |
| WO | WO-2011160206 A1 | 12/2011 |
| WO | WO-2012005805 A1 | 1/2012 |
| WO | WO-2012034132 A2 | 3/2012 |
| WO | WO-2012068589 A2 | 5/2012 |
| WO | WO-2012075080 A1 | 6/2012 |
| WO | WO-2012075500 A2 | 6/2012 |
| WO | WO-2012118812 A2 | 9/2012 |
| WO | WO-2012142513 A1 | 10/2012 |
| WO | WO-2013049770 A2 | 4/2013 |
| WO | WO 2013/155464 | 10/2013 |

OTHER PUBLICATIONS

Beisel et al. "Histone Methylation by the *Drosophila* Epigenetic Transcriptional Regulator Ash1." *Nature.* 419(2002):857-862.

Bernstein et al. "A Bivalent Chromatin Structure Marks Key Developmental Genes in Embryonic Stem Cells." *Cell.* 125.2(2006):315-326.

Bracken et al. "*EZH2* is Downstream of the pRB-E2F Pathway, Essential for Proliferation and Amplified in Cancer." *EMBO J.* 22.20(2003):5323-5335.

Braña et al. "Reaction of N-(2-Pyridylmethyl)-3,5-dimethylbenzamide and N-(3-Pyridylmethyl)-3,5-dimethylbenzamide N-Oxides With Acetic Anhydride." *Journal of Heterocyclic Chemistry.* 19.6(1982):1297-1300.

Cao et al. "Role of Histone H3 Lysine 27 Methylation in Polycomb-Group Silencing." *Science.* 298(2002):1039-1043.

Cao et al. "Role of hPHF1 in H3K27 Methylation and Hox Gene Silencing." *Mol. Cell. Biol.* 28.5(2008):1862-1872.

Cao et al. "SUZ12 is Required for Both the Histone Methyltransferase Activity and the Silencing Function of the EED-EZH2 Complex." *Mol. Cell.* 15.1(2004):57-67.

Copeland et al. "Targeting Epigenetic Enzymes for Drug Discovery." *Curr. Opin. Chem. Biol.* 14.4(2010):505-510.

Cui et al. "Chromatin Signatures in Multipotent Human Hematopoietic Stem Cells Indicate the Fate of Bivalent Genes During Differentiation." *Cell Stem Cell.* 4.1(2009):80-93.

Czermin et al. "*Drosphila* Enhancer of Zeste/ESC Complexes Have a Histone H3 Methyltransferase Activity That Marks Chromosomal Polycomb Sites." *Cell.* 111.2(2002):185-196.

Erhardt et al. "Consequence of the Depletion of Zygotic and Embryonic Enhancer of Zests 2 During Preimplantation Mouse Development." *Development.* 130(2003):4235-4248.

Francis et al. "Mechanisms of Transcriptional Memory." *Nat. Rev. Mol. Cell Biol.* 2(2001):409-421.

GenBank Accession No. CAB02546, Apr. 18, 2005.
GenBank Accession No. NM_001203249.1, Jun. 26, 2012.
GenBank Accession No. NM_003797, Jun. 27, 2012.
GenBank Accession No. NM_004447, Jun. 26, 2012.
GenBank Accession No. NM_004456, Jun. 26, 2012.
GenBank Accession No. NM_005610, Jun. 27, 2012.
GenBank Accession No. NM_015355, Jun. 28, 2012.
GenBank Accession No. NM_152998, Jun. 26, 2012.
GenBank Accession No. NM_153207, Jun. 30, 2012.
GenBank Accession No. NP_001190178.1, Jun. 26, 2012.
GenBank Accession No. NP_694543, Jun. 26, 2012.

Gura et al. "Systems for Identifying New Drugs are Often Faulty." *Science.* 278.5340(1997):1041-1042.

International Application No. PCT/US2012/026953 filed Feb. 28, 2012.

International Application No. PCT/US2012/033662 filed Apr. 13, 2012.

Johnson et al. "Relationships Between Drug Activity in NCI Preclinical in vitro and in vivo Models and Early Clinical Trials." *Brit. J. Cancer.* 84.10(2001):1424-1431.

Kirmizis et al. "Identification of the Polycomb Group Protein SU(Z)12 as a Potential Molecular Target for Human Cancer Therapy." *Mol. Cancer Ther.* 2(2003):113-121.

Kirmizis et al. "Silencing of Human Polycomb Target Genes is Associated With Methylation of Histone H3 Lys 27." *Genes Dev.* 18(2004):1592-1605.

Kleer et al. "EZH2 is a Marker of Aggressive Breast Cancer and Promotes Neoplastic Transformation of Breast Epithelial Cells." *PNAS.* 100.20(2003):11606-11611.

Knutson et al. "A Selective Inhibitor of EZH2 Blocks H3K27 Methylation and Kills Mutant Lymphoma Cells." *Nat. Chem. Biol.* 8(2012):890-896.

Kubicek et al."Reversal of H3K9me2 by a Small Molecule Inhibitor for the G9a Histone Methytransferase." *Mol. Cell.* 25(2007):473-481.

Kuzmichev et al. "Histone Methyltransferase Activity Associated With a Human Multiprotein Complex Containing the Enhancer of Zeste Protein." *Genes Dev.* 16(2002):2893-2905.

Lohr et al. "Discovery and Prioritization of Somatic Mutations in Diffuse Large B-Cell Lymphoma (DLBCL) by Whole-Exome Sequencing." *PNAS.* 109.10(2012):3879-3884. Epub Feb. 17, 2012.

Müller et al. "Histone Methyltransferase Activity of a *Drosophila* Polycomb Group Repressor Complex." *Cell.* 111.2(2002):197-208.

Majer et al. "A687V EZH2 is a Gain-of-Function Mutation Found in Lymphoma Patients." *FEBS Lett.* 586.19(2012):3448-3451.

Martinez-Garcia et al. "Deregulation of H3K27 Methylation in Cancer." *Nat. Genet.* 42(2010):100-101.

Martinez-Garcia et al. "The MMSET Histone Methyl Transferase Switches Global Histone Methylation and Alters Gene Expression in t(4;14) Multiple Myeloma Cells." Blood. 117(2011):211-220.

McCabe et al. "EZH2 Inhibition as a Therapeutic Strategy for Lymphoma With EZH2-Activating Mutations." *Nature.* Epub: Oct. 10, 2012.

McCabe et al. "Mutation of A677 in Histone Methyltransferase EZH2 in Human B-Cell Lymphoma Promotes Hypertrimethylation of Histone H3 on Lysine 27 (H3K27)." *PNAS.* 109.8(2012):2989-2994.

Milne et al. "MLL Targets SET Domain Methyltransferase Activity to *Hox* Gene Promoters." *Mol. Cell.* 10.5(2002):1107-1117.

Miranda et al. "DZNep is a Global Histone Methylation Inhibitor That Reactivates Developmental Genes not Silenced by DNA Methylation." *Mol. Cancer Ther.* 8.6(2009):1579-1588.

Nakamura et al. "ALL-1 is a Histone Methyltransferase That Assembles a Supercomplex of Proteins Involved in Transcriptional Regulation." *Mol. Cell.* 10.5(2002):1119-1128.

Otte et al. "Gene Repression by Polycomb Group Protein Complexes: A Distinct Complex for Every Occasion?" *Curr. Opin. Genet. Dev.* 13.5(2003):448-454.

Pearce et al. "Failure Modes in Anticancer Drug Discovery and Development." *Cancer Drug Design and Discovery.* Neidle, ed. Boston: Elsevier. (2008):424-435.

Plath et al. "Role of Histone H3 Lysince 27 Methylation in X Inactivation." *Science.* 300(2003):131-135.

Ryan et al. "EZH2 Codon 641 Mutations are Common in BCL2-Rearranged Germinal Center B Cell Lymphomas." *PLoS One.* 6.12(2011):E28585.

(56) References Cited

OTHER PUBLICATIONS

Sarma et al. "EZH2 Requires PHF1 to Efficiently Catalyze H3 Lysine 27 Trimethylation In Vivo." *Mol. Cell. Biol.* 28.8(2008):2718-2731.
Sculley et al. "Some Amide Derivatives of Certain Aminomethylpyridines." *J. Am. Chem. Soc.* 75.14(1953):3400-3403.
Shen et al. "EZH1 Mediates Methylation on Histone H3 Lysine 27 and Complements EZH2 in Maintaining Stem Cell Identity and Executing Pluripotency." *Mol. Cell.* 32.4(2008):491-502.
Silva et al. "Establishment of Histone H3 Methylation on the Inactive X Chromosome Requires Transient Recruitment of Eed-Enx1 Polycomb Group Complexes." *Dev. Cell.* 4.4(2003):481-495.
Simon et al. "Roles of the EZH2 Histone Methyltransferase in Cancer Epigenetics." *Mutat. Res.* 647.1-2(2008):21-29.
Simone. "Oncology: Introduction." *Cecil Textbook of Medicine.* Bennett et al., eds. Philadelphia: W. B. Saunders Co. 20th ed. 1(1996):1004-1104.
Sneeringer et al. "Coordinated Activities of Wild-Type Plus Mutant EZH2 Drive Tumor-Associated Hypertrimethylation of Lysine 27 on Histone H3 (H3K27) in Human B-Cell Lymphomas." *PNAS.* 107.49(2010):20980-20985.
Swiss-Prot Accession No. Q15910, Mar. 21, 2012.
Townsend et al. "New S-Adenosyl-L-Methionine Analogues: Synthesis and Reactivity Studies." *Org. Lett.* 11.14(2009):2976-2979.
van Haaften et al. "Somatic Mutations of the Histone H3K27 Demethylase Gene *UTX* in Human Cancer." *Nat. Genet.* 41(2009):521-523.
Varambally et al. "The Polycomb Group Protein EZH2 is Involved in Progression of Prostate Cancer." *Nature.* 419(2002):624-629.
Wang et al. "A Novel Human Homologue of *Drosophila* Polycomb-like Gene is Up-Regulated in Multiple Cancers." *Gene.* 343.1(2004):69-78.
Wigle et al. "The Y641C Mutation of EZH2 Alters Substrate Specificity for Histone H3 Lysine 27 Methylation States." *FEBS Lett.* 585.19(2011):3011-3014.
Wilson et al. "Epigenetic Antagonism Between Polycomb and SWI/SNF Complexes During Oncogenic Transformation." *Cancer Cell.* 18(2010):316-328.
Yap et al. "Somatic Mutations at EZH2 Y641 Act Dominantly Through a Mechanism of Selectively Altered PRC2 Catalytic Activity, to Increase H30K27 Trimethylation." *Blood.* 117.8(2010):2451-2459.
Richon, Victoria M. et al.: "Lymphoma-Associated Mutations of EZH2 Result in a Change-of-function", Blood, American Society of Hematology, vol. 116, No. 21, Nov. 1, 2010, p. 312, XP009176070, ISSN: 0006-4971.
Garapaty-Rao, Shivani et al.: "Identification of EZH2 and EZH1 Small Molecule Inhibitors with Selective Impact on Diffuse Large B Cell Lymphoma Cell Growth", *Chemistry & Biology*, vol. 20, No. 11, Nov. 1, 2013, pp. 1329-1339, XP055101733, ISSN: 1074-5521, DOI: 10.1016/j.chembiol.2013.09.013.
Wei, Qi et al.: "Selective inhibition of Ezh2 by a small molecule inhibitor blocks tumor cells proliferation", *Proceedings of the National Academy of Sciences of the United States of America*, Dec. 26, 2012, vol. 109, No. 52, pp. 21360-21365, XP002720302, ISSN: 1091-6490.
Copeland et al., "Protein methyltransferases as a target class for drug discovery" *Nature Reviews Drug Discovery* 8(2009): 724-732.
Morin et al., "Somatic mutations altering EZH2 (Tyr641) in follicular and diffuse large B-cell lymphomas of germinal-center origin" *Nature Genetics* 42(2010): 181-185; Article and Article including Supplemental Information provided.
Pollock et al., "Epigenetic approaches to cancer therapy" *Drug Discovery Today: Therapeutic Strategies* 6(2) (2009): 71-79.
Chen et al., "Cloning of a Human Homolog of the *Drosophila* Enhancer of zeste Gene (*EZH2*) That Maps to Chromosome 21q22.2" *Genomics* 38(1996): 30-37.
Fiskus et al., "Combined epigenetic therapy with the histone methyltransferase EZH2 inhibitor 3-deazaneplanocin A and the histone deacetylase inhibitor panobinostat against human AML cells" *Blood* 114(13) (2009): 2733-2743.
Siegel et al., "Cancer Statistics, 2013" *CA: A Cancer Journal for Clinicians* 63(1)(2013): 11-30.
Fiskus et al., "Combined Epigenetic Therapy with the Novel Histone Methyl Transferase EZH2 Inhibitor 3-Deazaneplanocin and Histone Deacetylase Inhibitor Panobinostat Exerts Synergistic Activity against Human Mantle Cell Lymphoma Cells", *Blood*, (ASH Annual Meeting Abstracts), 2008, 112: Abstract 3622.

EZH2 Mutation

KDM6A/UTX mutation

EZH2 overexpression

PHF19/PCL3 overexpression

FIG. 6

H3 Peptide Panel

| H3 amino acids | 1-15 | 6-20 | 11-25 | 16-30 | 21-35 | 26-40 | 31-45 | 36-50 | 41-55 | 46-60 | 51-65 | 56-70 | 61-75 | 66-80 | 71-85 | 76-90 | 81-95 | 86-100 | 91-105 | 96-110 | 101-115 | 106-120 | 111-125 | 116-130 | 121-135 |
|---|---|---|---|---|---|---|---|---|---|---|---|---|---|---|---|---|---|---|---|---|---|---|---|---|---|
| WT | 42 | 29 | 4 | 1045 | 15 | 12 | 3 | 3 | 3 | 2 | 2 | 2 | 2 | 2 | 2 | 1 | 1 | 2 | 2 | 2 | 1 | 2 | 1 | 1 | 2 |
| Y641F | 6 | 5 | 2 | 161 | 2 | 3 | 2 | 2 | 1 | 1 | 1 | 2 | 1 | 2 | 2 | 0 | 1 | 1 | 0 | 1 | 1 | 1 | 2 | 0 | 2 |
| Y641H | 2 | 2 | 0 | 9 | 0 | 0 | 1 | 2 | 1 | 1 | 0 | 0 | 1 | 1 | 1 | 1 | 1 | 1 | 1 | 0 | 0 | 0 | 3 | 0 | 1 |
| Y641N | 2 | 2 | 1 | 4 | 1 | 1 | 1 | 0 | 1 | 1 | 0 | 1 | 1 | 1 | 1 | 0 | 0 | 1 | 1 | 1 | 0 | 0 | 1 | 0 | 0 |
| Y641S | 2 | 2 | 0 | 13 | 0 | 1 | 2 | 0 | 1 | 0 | 0 | 0 | 0 | 1 | 2 | 0 | 1 | 0 | 0 | 0 | 0 | 0 | 2 | 1 | 0 |

H4 Peptide Panel

| H4 amino acids | 1-15 | 6-20 | 11-25 | 16-30 | 21-35 | 26-40 | 31-45 | 36-50 | 41-55 | 46-60 | 51-65 | 56-70 | 61-75 | 66-80 | 71-85 | 76-90 | 81-95 | 86-100 | 91-105 |
|---|---|---|---|---|---|---|---|---|---|---|---|---|---|---|---|---|---|---|---|
| WT | 2 | 5 | 2 | 3 | 1 | 3 | 4 | 4 | 2 | 1 | 1 | 1 | 1 | 1 | 1 | 2 | 2 | 2 | 5 |
| Y641F | 1 | 3 | 2 | 2 | 3 | 3 | 2 | 2 | 1 | 1 | 0 | 1 | 1 | 2 | 0 | 1 | 1 | 0 | 1 |
| Y641H | 1 | 1 | 0 | 0 | 0 | 3 | 0 | 1 | 0 | 0 | 0 | 0 | 0 | 1 | 0 | 1 | 0 | 0 | 0 |
| Y641N | 1 | 0 | 1 | 0 | 0 | 0 | 0 | 1 | 0 | 0 | 0 | 1 | 0 | 1 | 0 | 1 | 0 | 0 | 0 |
| Y641S | 0 | 1 | 1 | 0 | 1 | 2 | 0 | 0 | 1 | 0 | 0 | 0 | 0 | 1 | 0 | 0 | 1 | 1 | 0 |

Potency of SAH against EZH2 mutants

Compound 75 potency against EZH2 WT and Y641 mutants

INHIBITORS OF HUMAN EZH2, AND METHODS OF USE THEREOF

RELATED REFERENCE

This application is a continuation of U.S. patent application Ser. No. 13/230,703, filed on Sep. 12, 2011, now U.S. Pat. No. 8,895,245, which claims priority to, and benefit of, U.S. Provisional Application No. 61/381,684, filed Sep. 10, 2010, the contents of each of which are incorporated herein by reference in their entireties.

FIELD OF THE INVENTION

This invention relates to inhibition of wild-type and certain mutant forms of human histone methyltransferase EZH2, the catalytic subunit of the PRC2 complex which catalyzes the mono- through tri-methylation of lysine 27 on histone H3 (H3-K27), methods for treating cancers including follicular lymphoma and diffuse large B-cell lymphoma (DLBCL) and methods for determining responsiveness to an EZH2 inhibitor in a subject.

BACKGROUND

In eukaryotic cells DNA is packaged with histones to form chromatin. Approximately 150 base pairs of DNA are wrapped twice around an octamer of histones (two each of histones 2A, 2B, 3 and 4) to form a nucleosome, the basic unit of chromatin. Changes in the ordered structure of chromatin can lead to alterations in transcription of associated genes. This process is highly controlled because changes in gene expression patterns can profoundly affect fundamental cellular processes, such as differentiation, proliferation and apoptosis. Control of changes in chromatin structure (and hence of transcription) is mediated by covalent modifications to histones, most notably of their N-terminal tails. These modifications are often referred to as epigenetic because they can lead to heritable changes in gene expression, but they do not affect the sequence of the DNA itself. Covalent modifications (for example, methylation, acetylation, phosphorylation and ubiquitination) of the side chains of amino acids are enzymatically mediated.

The selective addition of methyl groups to specific amino acid sites on histones is controlled by the action of a unique family of enzymes known as histone methyltransferases (HMTs). The level of expression of a particular gene is influenced by the presence or absence of one or more methyl groups at a relevant histone site. The specific effect of a methyl group at a particular histone site persists until the methyl group is removed by a histone demethylase, or until the modified histone is replaced through nucleosome turnover. In a like manner, other enzyme classes can decorate DNA and histones with other chemical species, and still other enzymes can remove these species to provide control of gene expression.

The orchestrated collection of biochemical systems behind transcriptional regulation must be tightly controlled in order for cell growth and differentiation to proceed optimally. Disease states result when these controls are disrupted by aberrant expression and/or activity of the enzymes responsible for DNA and histone modification. In human cancers, for example, there is a growing body of evidence to suggest that dysregulated epigenetic enzyme activity contributes to the uncontrolled cell proliferation associated with cancer as well as other cancer-relevant phenotypes such as enhanced cell migration and invasion. Beyond cancer, there is growing evidence for a role of epigenetic enzymes in a number of other human diseases, including metabolic diseases (such as diabetes), inflammatory diseases (such as Crohn's disease), neurodegenerative diseases (such as Alzheimer's disease), and cardiovascular diseases. Therefore, selectively modulating the aberrant action of epigenetic enzymes holds great promise for the treatment of a range of diseases.

Histone Methyltransferase EZH2

Polycomb group (PcG) and trithorax group (trxG) proteins are known to be part of the cellular memory system. Francis et al. (2001) *Nat Rev Mol Cell Biol* 2:409-21; Simon et al. (2002) *Curr Opin Genet Dev* 12:210-8. Both groups of proteins are involved in maintaining the spatial patterns of homeotic box (Hox) gene expression, which are established early in embryonic development by transiently expressed segmentation genes. In general, PcG proteins are transcriptional repressors that maintain the "off state," and trxG proteins are transcriptional activators that maintain the "on state." Because members of PcG and trxG proteins contain intrinsic histone methyltransferase (HMTase) activity, PcG and trxG proteins may participate in cellular memory through methylation of core histones. Beisel et al. (2002) *Nature* 419:857-62; Cao et al. (2002) *Science* 298:1039-43; Czermin et al. (2002) *Cell* 111:185-96; Kuzmichev et al. (2002) *Genes Dev* 16:2893-905; Milne et al. (2002) *Mol Cell* 10:1107-17; Muller et al. (2002) *Cell* 111:197-208; Nakamura et al. (2002) *Mol Cell* 10:1119-28.

Biochemical and genetic studies have provided evidence that *Drosophila* PcG proteins function in at least two distinct protein complexes, the Polycomb repressive complex 1 (PRC1) and the ESC-E(Z) complex (also known as Polycomb repressive complex 2 (PRC2)), although the compositions of the complexes may be dynamic. Otte et al. (2003) *Curr Opin Genet Dev* 13:448-54. Studies in *Drosophila* (Czermin et al. (supra); Muller et al. (supra)) and mammalian cells (Cao et al. (supra); Kuzmichev et al. (supra)) have demonstrated that the ESC-E(Z)/EED-EZH2 (i.e., PRC2) complexes have intrinsic histone methyltransferase activity. Although the compositions of the complexes isolated by different groups are slightly different, they generally contain EED, EZH2, SUZ12, and RbAp48 or *Drosophila* homologs thereof. However, a reconstituted complex comprising only EED, EZH2, and SUZ12 retains histone methyltransferase activity for lysine 27 of histone H3. U.S. Pat. No. 7,563,589 (incorporated by reference).

Of the various proteins making up PRC2 complexes, EZH2 (Enhancer of Zeste Homolog 2) is the catalytic subunit. The catalytic site of EZH2 in turn is present within a SET domain, a highly conserved sequence motif (named after Su(var)3-9, Enhancer of Zeste, Trithorax) that is found in several chromatin-associated proteins, including members of both the Trithorax group and Polycomb group. SET domain is characteristic of all known histone lysine methyltransferases except the H3-K79 methyltransferase DOT1.

In addition to Hox gene silencing, PRC2-mediated histone H3-K27 methylation has been shown to participate in X-inactivation. Plath et al. (2003) *Science* 300:131-5; Silva et al. (2003) *Dev Cell* 4:481-95. Recruitment of the PRC2 complex to Xi and subsequent trimethylation on histone H3-K27 occurs during the initiation stage of X-inactivation and is dependent on Xist RNA. Furthermore, EZH2 and its associated histone H3-K27 methyltransferase activity was found to mark differentially the pluripotent epiblast cells and the differentiated trophectoderm. Erhardt et al. (2003) *Development* 130:4235-48).

Consistent with a role of EZH2 in maintaining the epigenetic modification patterns of pluripotent epiblast cells, Cremediated deletion of EZH2 results in loss of histone H3-K27 methylation in the cells. Erhardt et al. (supra). Further, studies in prostate and breast cancer cell lines and tissues have revealed a strong correlation between the levels of EZH2 and SUZ12 and the invasiveness of these cancers (Bracken et al. (2003) *EMBO J* 22:5323-35; Kirmizis et al. (2003) *Mol Cancer Ther* 2:113-21; Kleer et al. (2003) *Proc Natl Acad Sci USA* 100:11606-11; Varambally et al. (2002) *Nature* 419:624-9), indicating that dysfunction of the PRC2 complex may contribute to cancer.

Recently, somatic mutations of tyrosine 641 (Y641F, Y641N, Y641S and Y641H) of EZH2 were reported to be associated with follicular lymphoma (FL) and the germinal center B cell-like (GCB) subtype of diffuse large B-cell lymphoma (DLBCL). Morin et al. (2010) *Nat Genet* 42:181-5. In all cases, occurrence of the mutant EZH2 gene was found to be heterozygous, and expression of both wild-type and mutant alleles was detected in the mutant samples profiled by transcriptome sequencing. It was also demonstrated that all of the mutant forms of EZH2 could be incorporated into the multi-protein PRC2 complex, but that the resulting complexes lacked the ability to catalyze methylation of the H3-K27 equivalent residue of a peptidic substrate. Hence, it was concluded that the disease-associated changes at Tyr641 of EZH2 resulted in loss of function with respect to EZH2-catalyzed H3-K27 methylation.

SUMMARY OF THE INVENTION

One aspect of the present invention relates to modulating the activity of the wild-type and mutant histone methyltransferase EZH2, the catalytic subunit of the PRC2 complex which catalyzes the mono- through tri-methylation of lysine 27 on histone H3 (H3-K27). For example, the present invention relates to inhibiting the activity of certain mutant forms of EZH2. The mutant forms of EZH2 include a substitution of another amino acid residue for tyrosine 641 (Y641, also Tyr641) of wild-type EZH2.

Another aspect of the present invention relates to determining a patient's responsiveness to an EZH2 inhibitor according to the dimethylated H3-K27me2 level, or preferably according to the levels of dimethylated H3-K27me2 and trimethylated H3-K27me3. For example, cells with low or undetectable level of dimethylated H3-K27me2 or cells with low ratio of H3-K27me2/me3 are much more responsive to the antiproliferative effect of an EZH2 inhibitor than cells with the more typical higher H3-K27me2/me3 ratio.

An aspect of the invention is a method of inhibiting in a subject conversion of H3-K27 to trimethylated H3-K27. The method comprises the step of administering to a subject expressing a Y641 mutant of EZH2 a therapeutically effective amount of an inhibitor of EZH2, wherein the inhibitor inhibits histone methyltransferase activity of EZH2, thereby inhibiting conversion of H3-K27 to trimethylated H3-K27 in the subject.

In this and other aspects of the invention, in one embodiment the inhibitor inhibits histone methyltransferase activity of the Y641 mutant of EZH2.

In this and other aspects of the invention, in one embodiment the inhibitor selectively inhibits histone methyltransferase activity of the Y641 mutant of EZH2.

In this and other aspects of the invention, in one embodiment the Y641 mutant of EZH2 is selected from the group consisting of Y641F, Y641H, Y641N, and Y641 S.

In this and other aspects of the invention, in one embodiment the inhibitor of EZH2 is S-adenosyl-L-homocysteine or a pharmaceutically acceptable salt thereof.

In this and other aspects of the invention, in one embodiment the inhibitor of EZH2 is Compound 75

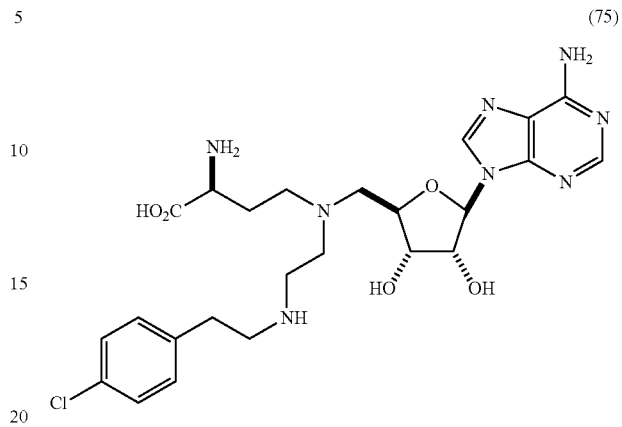

(75)

or a pharmaceutically acceptable salt thereof.

An aspect of the invention is a method of inhibiting in a subject conversion of H3-K27 to trimethylated H3-K27. The method comprises the steps of performing an assay to detect a Y641 mutant of EZH2 in a sample from a subject; and administering to a subject expressing a Y641 mutant of EZH2 a therapeutically effective amount of an inhibitor of EZH2, wherein the inhibitor inhibits histone methyltransferase activity of EZH2, thereby inhibiting conversion of H3-K27 to trimethylated H3-K27 in the subject.

In this and other aspects of the invention, in one embodiment, performing the assay to detect the Y641 mutant of EZH2 includes whole-genome resequencing or target region resequencing that detects a nucleic acid encoding the Y641 mutant of EZH2.

In this and other aspects of the invention, in one embodiment, performing the assay to detect the Y641 mutant of EZH2 includes contacting the sample with an antibody that binds specifically to a polypeptide or fragment thereof characteristic of the Y641 mutant of EZH2.

In this and other aspects of the invention, in one embodiment, performing the assay to detect the Y641 mutant of EZH2 includes contacting the sample under highly stringent conditions with a nucleic acid probe that hybridizes to a nucleic acid encoding a polypeptide or fragment thereof characteristic of the Y641 mutant of EZH2.

An aspect of the invention is a method of inhibiting conversion of H3-K27 to trimethylated H3-K27. The method comprises the step of contacting a Y641 mutant of EZH2 with a histone substrate comprising H3-K27 and an effective amount of an inhibitor of EZH2, wherein the inhibitor inhibits histone methyltransferase activity of EZH2, thereby inhibiting conversion of H3-K27 to trimethylated H3-K27.

An aspect of the invention is a method of identifying a subject as a candidate for treatment with an inhibitor of EZH2. The method comprises the steps of performing an assay to detect a Y641 mutant of EZH2 in a sample from a subject; and identifying a subject expressing a Y641 mutant of EZH2 as a candidate for treatment with an inhibitor of EZH2, wherein the inhibitor inhibits histone methyltransferase activity of EZH2.

An aspect of the invention is a method identifying an inhibitor of a Y641 mutant of EZH2. The method comprises the steps of combining an isolated Y641 mutant of EZH2 with a histone substrate, a methyl group donor, and a test compound, wherein the histone substrate comprises a form of H3-K27 selected from the group consisting of unmethylated H3-K27, monomethylated H3-K27, dimethylated H3-K27, and any combination of thereof; and performing an assay to detect methylation of H3-K27 in the histone substrate, thereby identifying the test compound as an inhibitor of the Y641 mutant of EZH2 when methylation of H3-K27 in the presence of the test compound is less than methylation of H3-K27 in the absence of the test compound.

In one embodiment, performing the assay to detect methylation of H3-K27 in the histone substrate comprises measuring incorporation of labeled methyl groups.

In one embodiment, the labeled methyl groups are isotopically labeled methyl groups.

In one embodiment, performing the assay to detect methylation of H3-K27 in the histone substrate comprises contacting the histone substrate with an antibody that binds specifically to trimethylated H3-K27.

An aspect of the invention is a method of identifying an inhibitor of a Y641 mutant of EZH2. The method comprises the steps of combining an isolated Y641 mutant of EZH2 with a histone substrate, a methyl group donor, and a test compound, wherein the histone substrate comprises a form of H3-K27 selected from the group consisting of unmethylated H3-K27, monomethylated H3-K27, dimethylated H3-K27, and any combination thereof; and performing an assay to detect formation of trimethylated H3-K27 in the histone substrate, thereby identifying the test compound as an inhibitor of the Y641 mutant of EZH2 when formation of trimethylated H3-K27 in the presence of the test compound is less than formation of trimethylated H3-K27 in the absence of the test compound.

In one embodiment, performing the assay to detect formation of trimethylated H3-K27 in the histone substrate comprises measuring incorporation of labeled methyl groups.

In one embodiment, the labeled methyl groups are isotopically labeled methyl groups.

In one embodiment, performing the assay to detect formation of trimethylated H3-K27 in the histone substrate comprises contacting the histone substrate with an antibody that binds specifically to trimethylated H3-K27.

An aspect of the invention is a method of identifying a selective inhibitor of a Y641 mutant of EZH2. The method comprises the steps of combining an isolated Y641 mutant of EZH2 with a histone substrate, a methyl group donor, and a test compound, wherein the histone substrate comprises a form of H3-K27 selected from the group consisting of monomethylated H3-K27, dimethylated H3-K27, and a combination of monomethylated H3-K27 and dimethylated H3-K27, thereby forming a test mixture; combining an isolated wild-type EZH2 with a histone substrate, a methyl group donor, and a test compound, wherein the histone substrate comprises a form of H3-K27 selected from the group consisting of monomethylated H3-K27, dimethylated H3-K27, and a combination of monomethylated H3-K27 and dimethylated H3-K27, thereby forming a control mixture; performing an assay to detect trimethylation of the histone substrate in each of the test mixture and the control mixture; calculating the ratio of (a) trimethylation with the Y641 mutant of EZH2 and the test compound (M+) to (b) trimethylation with the Y641 mutant of EZH2 without the test compound (M−); calculating the ratio of (c) trimethylation with wild-type EZH2 and the test compound (WT+) to (d) trimethylation with wild-type EZH2 without the test compound (WT−); comparing the ratio (a)/(b) with the ratio (c)/(d); and identifying the test compound as a selective inhibitor of the Y641 mutant of EZH2 when the ratio (a)/(b) is less than the ratio (c)/(d).

An aspect of the invention is a method of treating cancer. The method comprises the step of administering to a subject having a cancer expressing a Y641 mutant of EZH2 a therapeutically effective amount of an inhibitor of EZH2, wherein the inhibitor inhibits histone methyltransferase activity of EZH2, thereby treating the cancer.

In this and other aspects of the invention, in one embodiment the cancer is selected from the group consisting of follicular lymphoma and diffuse large B-cell lymphoma (DLBCL) of germinal center B cell-like (GCB) subtype.

An aspect of the invention is a method of treating cancer. The method comprises the step of administering to a subject having a cancer expressing a Y641 mutant of EZH2 a therapeutically effective amount of an inhibitor of EZH2, wherein the inhibitor selectively inhibits histone methyltransferase activity of the Y641 mutant of EZH2, thereby treating the cancer.

An aspect of the invention is a method of treating cancer. The method comprises the steps of performing an assay to detect a Y641 mutant of EZH2 in a sample comprising cancer cells from a subject having a cancer, and administering to a subject expressing a Y641 mutant of EZH2 a therapeutically effective amount of an inhibitor of EZH2, wherein the inhibitor inhibits histone methyltransferase activity of EZH2, thereby treating the cancer.

Another aspect of the invention is a method for determining responsiveness to an EZH2 inhibitor in a subject. In one embodiment the method includes isolating a tissue sample from the subject; detecting a dimethylation (me2) level of H3-K27 in the tissue sample; comparing the dimethylation (me2) level to a control dimethylation (me2) level; and identifying the subject is responsive to said EZH2 inhibitor when the dimethylation (me2) level is absent or lower than the control dimethylation (me2) level. In one embodiment, the method further includes detecting a trimethylation (me3) level of H3-K27 in the tissue sample; comparing the trimethylation (me3) level to a control trimethylation (me3) level and the dimethylation (me2) level to a control dimethylation (me2) level; and identifying said subject is responsive to the EZH2 inhibitor when the trimethylation (me3) level is same as or higher than the control trimethylation (me3) level and the dimethylation (me2) level is absent or lower than the control dimethylation (me2) level. In another embodiment, the method further includes obtaining a ratio of the dimethylation (me2) level to the trimethylation (me3) level of H3-K27 in the tissue sample; obtaining a control ratio of the control dimethylation (me2) level to the control trimethylation (me3) level; comparing the ratio to the control ratio; and identifying the subject is responsive to said EZH2 inhibitor when said ratio is lower than said control ratio. In a preferred embodiment, the subject has cancer. In one embodiment, the cancer is a follicular lymphoma. Alternatively, the cancer is a diffuse large B-cell lymphoma (DLBCL). In another preferred embodiment, the subject expresses a Y641 mutant EZH2. In a preferred embodiment, the Y641 mutant is Y641F, Y641H, Y641N or Y641S.

An aspect of the invention is method for selecting a treatment for a subject having a cancer. The method includes determining responsiveness of the subject to an EZH2 inhibitor by the dimethylated H3-K27 level or preferably by the levels of dimethylated H3-K27 and trimethlated H3-K27; and providing the EZH2 inhibitor to the subject when the subject is responsive to the EZH2 inhibitor. In one embodiment, the cancer is a follicular lymphoma. Alternatively, the cancer is a diffuse large B-cell lymphoma (DLBCL). In another preferred embodiment, the subject expresses a Y641 mutant EZH2. In a preferred embodiment, the Y641 mutant is Y641F, Y641H, Y641N or Y641S.

An aspect of the invention is Compound 75

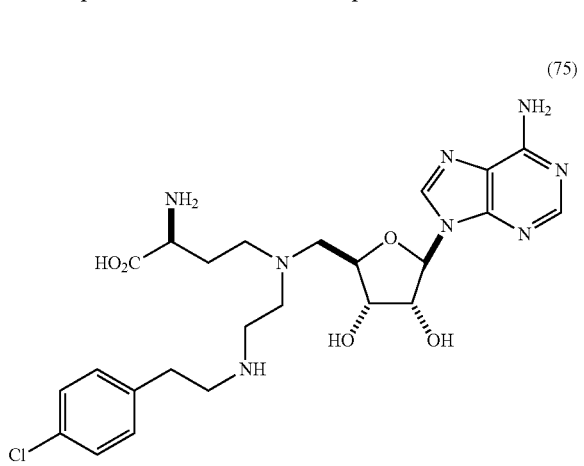

(75)

or a pharmaceutically acceptable salt thereof.

An aspect of the invention is a pharmaceutical composition comprising Compound 75

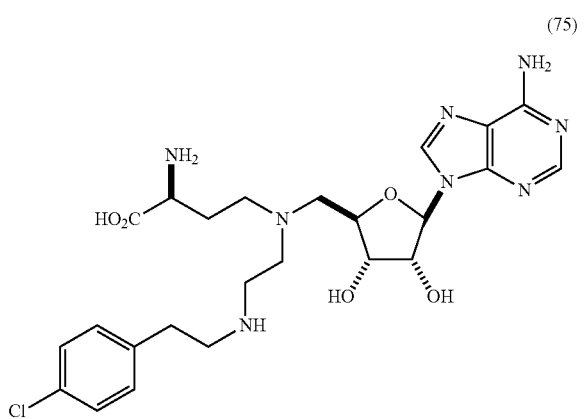

(75)

or a pharmaceutically acceptable salt thereof.

An aspect of the invention is the use of Compound 75

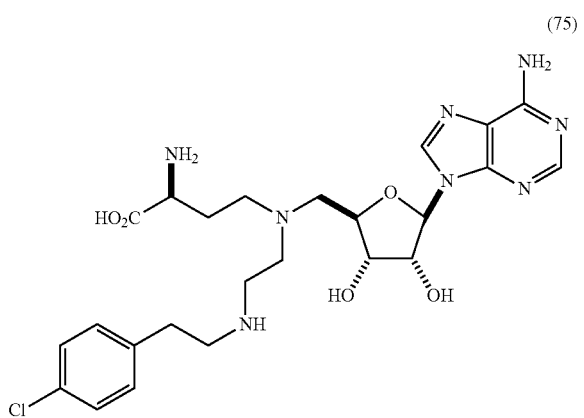

(75)

or a pharmaceutically acceptable salt thereof in the treatment of follicular lymphoma.

An aspect of the invention is the use of Compound 75

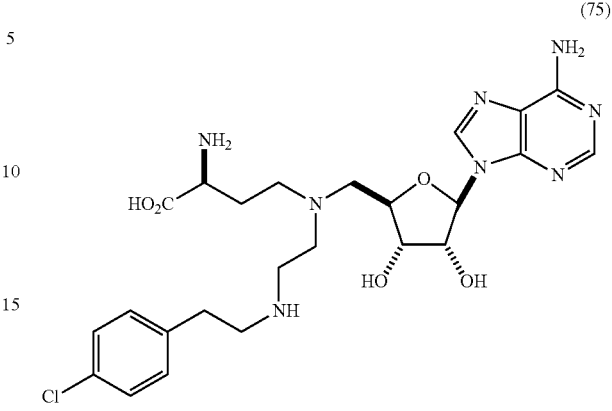

(75)

or a pharmaceutically acceptable salt thereof in the treatment of diffuse large B-cell lymphoma (DLBCL).

Unless otherwise defined, all technical and scientific terms used herein have the same meaning as commonly understood by one of ordinary skill in the art to which this invention belongs. In the specification, the singular forms also include the plural unless the context clearly dictates otherwise. Although methods and materials similar or equivalent to those described herein can be used in the practice or testing of the present invention, suitable methods and materials are described below. All publications, patent applications, patents and other references mentioned herein are incorporated by reference. The references cited herein are not admitted to be prior art to the claimed invention. In the case of conflict, the present specification, including definitions, will control. In addition, the materials, methods and examples are illustrative only and are not intended to be limiting.

Other features and advantages of the invention will be apparent from the following detailed description and claims.

BRIEF DESCRIPTION OF THE FIGURES

(FIG. 2A) Methyltransferase activity of mutant and wild-type (WT) complexes on unmethylated peptide (open bars), monomethylated peptide (hashed bars), and dimethylated peptide (closed bars). (FIG. 2B) Affinity for peptide substrates as judged by $K_{1/2}$ is similar across all peptide methylation states for PRC2 complexes containing wild-type (○), Y641F (●), Y641H (□), Y641N (■), and Y641S (▲) EZH2. Note that the variation in $K_{1/2}$ values across all substrates and all enzyme forms is less than 3.5-fold. For any particular methylation state of substrate the variation in $K_{1/2}$ value is less than 2-fold. (FIG. 2C) Enzyme turnover number ($k_{cat}$) varies with substrate methylation status in opposing ways for WT and Y641 mutants of EZH2. The $k_{cat}$ decreases with increasing K27 methylation states for wild-type (○), but increases for Y641F (●), Y641H (□), Y641N (■), and Y641S (▲) mutants of EZH2. (FIG. 2D) Catalytic efficiency ($k_{cat}/K_{1/2}$) decreases with increasing K27 methylation states for wild-type (○), but increases for Y641F (●), Y641H (□), Y641N (■), and Y641S (▲) mutants of EZH2. In panels B-D, the lines drawn to connect the data points are not intended to imply any mathematical relationship; rather, they are merely intended to serve as visual aides.

FIG. 4A) mutation of Y641 in EZH2 resulting in a change in substrate preference from the nonmethylated to the mono- and di-methylated histone H3-K27; FIG. 4B) overexpression of EZH2; FIG. 4C) mutations in UTX that inactivate enzyme function, causing a decrease in demethylation of H3-K27me3; and FIG. 4D) overexpression of the PRC2 complex subunit PHF19/PCL3 that leads to increases in recruitment of the PRC2 complex to specific genes and an increase in histone H3-K27 trimethylation. In all four models the alteration leads to aberrant histone H3-K27 trimethylation in the proximal promoter regions of genes resulting in transcriptional repression of key genes in cancer.

FIG. 6 is a pair of tables showing that mutant and wild-type (WT) PRC2 complexes display strong substrate preference for H3-K27-containing peptides. Each enzyme was tested against a panel of overlapping 15-mer peptides covering all of H3 and H4. Activity was measured as velocity (CPM per minute), and the reported value represents the mean of two independent determinations for each reaction. For all the complexes the most favored peptide was H3:16-30. WT complex had greater than 6-fold more activity against this peptide than any of the mutant complexes.

FIG. 9A) Histones were extracted from the cell lines shown, fractionated by SDS-PAGE on a 4-20% gel, transferred to nitrocellulose membranes, and probed with antibodies to Histone H3, H3-K27me1, me2, or me3. EZH2 levels were determined by preparing whole cell lysates from the cell lines shown, treating as above and probing with an antibody to EZH2; FIG. 9B) Histones were extracted from the cell lines shown and treated as above, except EZH2 levels were not determined.

DETAILED DESCRIPTION

Figure 1B:
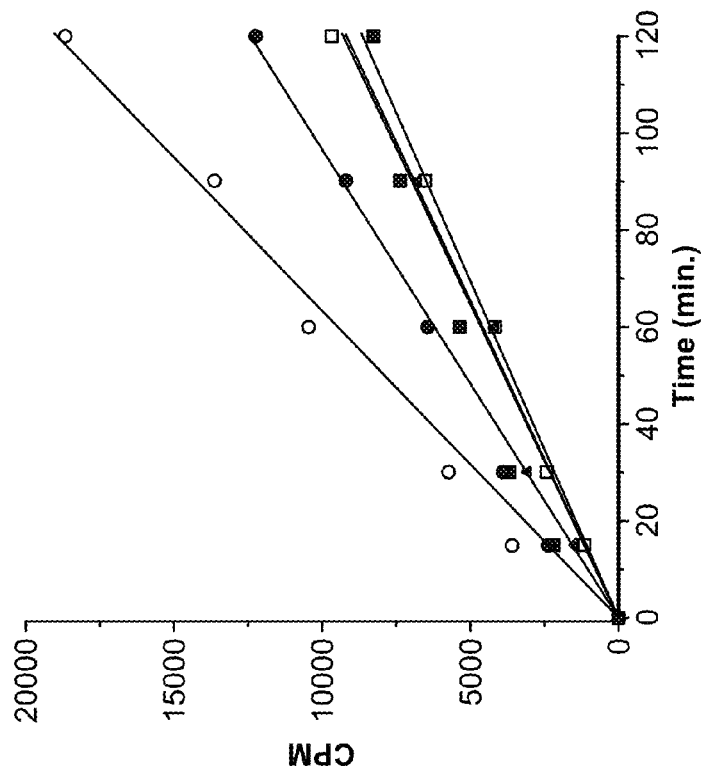
FIGS. 1A and 1B are two graphs establishing that B-cell lymphoma-associated mutants of EZH2 are active histone methyltransferases. In vitro methyltransferase activity of PRC2 complexes containing wild-type and various Y641 mutants of EZH2 was measured as (FIG. 1A) methyl transfer reactions using a peptide (H3 21-44) as substrate, and (FIG. 1B) methyl transfer reactions using avian nucleosomes as substrate. Symbols: wild-type (●), Y641F (○), Y641H (□), Y641N (■), and Y641S (▲). CPM is counts per minute, referring to scintillation counting as a result of $^3$H radiation.

Chromatin structure is important in gene regulation and epigenetic inheritance. Post-translational modifications of histones are involved in the establishment and maintenance of higher-order chromatin structure; for example, the tails of certain core histones are modified by acetylation, methylation, phosphorylation, ribosylation and/or ubiquitination.

EZH2 is a histone methyltransferase that is the catalytic subunit of the PRC2 complex which catalyzes the mono- through tri-methylation of lysine 27 on histone H3 (H3-K27). Histone H3-K27 trimethylation is a mechanism for suppressing transcription of specific genes that are proximal to the site of histone modification. This trimethylation is known to be a cancer marker with altered expression in cancer, such as prostate cancer (see, e.g., U.S. Patent Application Publication No. 2003/0175736; incorporated herein by reference in its entirety). EZH2 belongs to the Polycomb group protein family (PcG). The polycomb group proteins help in maintaining cellular identity by transcriptional repression of target genes. Jacobs et al. (1999) *Semin Cell Dev Biol* 10(2):227-35; Jacobs et al. (2002) *Biochim Biophys Acta* 1602(2):151-61. DNA microarrays identified EZH2 as being up-regulated in hormone-refractory metastatic prostate cancer. Dhanasekaran et al. (2001) *Nature* 412(6849):822-6; Varambally et al. (2002) *Nature* 419(6907):624-9. EZH2 is up-regulated in aggressive breast tumors and is a mediator of a pro-invasive phenotype. Kleer et al. (2003) *Proc Natl Acad Sci USA* 100(20): 11606-11. Overexpression of EZH2 in immortalized human mammary epithelial cell lines promotes anchorage-independent growth and cell invasion. Kleer et al. (supra). EZH2-mediated cell invasion required an intact SET domain and histone deacetylase activity. Previous studies provided evidence for a functional link between dysregulated EZH2 expression, transcriptional repression, and neoplastic transformation. Varambally et al. (supra); Kleer et al (supra).

An aspect of the present invention relates to inhibiting the activity of EZH2, including certain mutant forms of EZH2. In one embodiment the present invention relates to inhibiting selectively the activity of certain mutant forms of EZH2.

Point mutations of the EZH2 gene at a single amino acid residue (Tyr641, herein referred to as Y641) of EZH2 have been reported to be linked to subsets of human B-cell lymphoma. Morin et al. (2010) *Nat Genet* 42(2):181-5. In particular, Morin et al. reported that somatic mutations of tyrosine 641 (Y641F, Y641H, Y641N, and Y641S) of EZH2 were associated with follicular lymphoma (FL) and the germinal center B cell-like (GCB) subtype of diffuse large B-cell lymphoma (DLBCL). The mutant allele is always found associated with a wild-type allele (heterozygous) in disease cells, and the mutations were reported to ablate the enzymatic activity of the PRC2 complex for methylating an unmodified peptide substrate.

It has now been unexpectedly discovered that the wild-type (WT) EZH2 enzyme displays greatest catalytic efficiency (kcat/K) for the zero- to mono-methylation reaction of H3-K27 and lesser efficiency for subsequent (mono- to di- and di- to tri-methylation) reactions; whereas, in stark contrast, the disease-associated Y641 mutations display very limited ability to perform the first methylation reaction but have enhanced catalytic efficiency for the subsequent reactions relative to wild-type enzyme. These results imply that the malignant phenotype of disease exploits the combined activities of a H3-K27 mono-methylating enzyme (PRC2 containing WT EZH2 or EZH1) together with PRC2 containing mutant EZH2 for augmented conversion of H3-K27 to the tri-methylated form (H3-K27me3).

While not intending to be bound by any one theory, it is hypothesized that the mutation of Y641 to phenylalanine (F), histidine (H), asparagine (N), or serine (S) in EZH2 may facilitate multiple rounds of H3-K27 methylation by impacting the H-bonding pattern and/or steric crowding in the active site of the enzyme-bisubstrate ternary complex, affecting the formation of a proper water channel for deprotonation of the reacting lysine. Zhang et al. (2008) *Proc Natl Acad Sci USA* 105:5728-32. This inference is drawn by analogy to the crystallographic and molecular dynamic simulation results seen for tyrosine mutation in the related protein lysine methyltransferases LSMT, Dim-5 and SET7/9.

For example, when tyrosine 245 of recombinant SET7/9 was mutated to alanine a change in substrate specificity was observed. Dillon et al. (2005) *Genome Biol* 6:227. The ability of the Y245A mutant SET7/9 to methylate an unmodified 20-residue peptide, representing the sequence surrounding H3-K4, was reduced to ca. 20% of WT enzyme. Xiao et al. (2003) *Nature* 421:652-6. At the same time, the ability of the Y245A mutant to further methylate H3-K4me1 and H3-K4me2 peptides was greatly augmented (ca. 7-fold and 5-fold, respectively) relative to WT enzyme. In contrast to the instant disclosure in respect of mutations of Y641 of EZH2, however, mutation of SET7/9 Y245 to phenylalanine did not enhance mono-to-di nor di-to-tri methylation of the peptide; rather, the Y245F mutant of SET7/9 displayed minimal catalytic activity for all peptidic substrates. Similarly, the wild-type enzyme G9a can dimethylate H3-K9 but is unable to perform the di-to-tri methylation reaction. Yet, when tyrosine 1067 of G9a (analogous to Y641 of EZH2) is mutated to phenylalanine, the enzyme now gains the ability to trimethylate H3-K9. Wu, H. et al. (2010) *PLoS One* 5, e8570, doi: 10.1371/journal.pone.0008570).

Human EZH2 nucleic acids and polypeptides have previously been described. See, e.g., Chen et al. (1996) *Genomics* 38:30-7 [746 amino acids]; Swiss-Prot Accession No. Q15910 [746 amino acids]; GenBank Accession Nos. NM_004456 and NP_004447 (isoform a [751 amino acids]); and GenBank Accession Nos. NM_152998 and NP_694543 (isoform b [707 amino acids]), each of which is incorporated herein by reference in its entirety.

```
Amino acid sequence of human EZH2 (Swiss-Prot
Accession No. Q15910)
                                          (SEQ ID NO: 1)
MGQTGKKSEKGPVCWRKRVKSEYMRLRQLKRFRRADEVKSMFSSNRQKIL

ERTEILNQEWKQRRIQPVHILTSVSSLRGTRECSVTSDLDFPTQVIPLKT

LNAVASVPIMYSWSPLQQNFMVEDETVLHNIPYMGDEVLDQDGTFIEELI

KNYDGKVHGDRECGFINDEIFVELVNALGQYNDDDDDDGDDPEEREEKQ

KDLEDHRDDKESRPPRKFPSDKIFEAISSMFPDKGTAEELKEKYKELTEQ

QLPGALPPECTPNIDGPNAKSVQREQSLHSFHTLFCRRCFKYDCFLHPFH

ATPNTYKRKNTETALDNKPCGPQCYQHLEGAKEFAAALTAERIKTPPKRP

GGRRRGRLPNNSSRPSTPTINVLESKDTDSDREAGTETGGENNDKEEEEK

KDETSSSSEANSRCQTPIKMKPNIEPPENVEWSGAEASMFRVLIGTYYDN

FCAIARLIGTKTCRQVYEFRVKESSIIAPAPAEDVDTPPRKKKRKHRLWA

AHCRKIQLKKDGSSNHVYNYQPCDHPRQPCDSSCPCVIAQNFCEKFCQCS

SECQNRFPGCRCKAQCNTKQCPCYLAVRECDPDLCLTCGAADHWDSKNVS

CKNCSIQRGSKKHLLLAPSDVAGWGIFIKDPVQKNEFISEYCGEIISQDE

ADRRGKVYDKYMCSFLFNLNNDFVVDATRKGNKIRFANHSVNPNCYAKVM

MVNGDHRIGIFAKRAIQTGEELFFDYRYSQADALKYVGIEREMEIP mRNA sequence of human EZH2, transcript variant 1
(GenBank Accession No. NM_004456)
                                          (SEQ ID NO: 2)
ggcggcgcttgattgggctggggggggccaaataaaagcgatggcgattgg gctgccgcgtttggcgctcggtccggtcgcgtccgacacccggtgggact cagaaggcagtggagcccggcggcggcggcggcggcgcgggggcgac gcgcgggaacaacgcgagtcggcgcgcgggacgaagaataatcatgggcc agactgggaagaaatctgagaagggaccagtttgttggcggaagcgtgta aaatcagagtacatgcgactgagacagctcaagaggttcagacgagctga tgaagtaaagagtatgtttagttccaatcgtcagaaaattttggaaagaa cggaaatcttaaaccaagaatggaaacagcgaaggatacagcctgtgcac
``` atcctgacttctgtgagctcattgcgcgggactagggagtgttcggtgac
cagtgacttggattttccaacacaagtcatcccattaaagactctgaatg
cagttgcttcagtacccataatgtattcttggtctcccctacagcagaat
tttatggtggaagatgaaactgttttacataacattccttatatgggaga
tgaagtttagatcaggatggtactttcattgaagaactaataaaaaatt
atgatgggaaagtacacggggatagagaatgtgggtttataaatgatgaa
attttgtggagttggtgaagaaatttccttctgataaaattttttgaagc
cattcctcaatgtttccagataagggcacagcagaagaactaaaggaaa
aatataaagaactcaccgaacagcagctcccaggcgcacttcctcctgaa
tgtaccccaacatagatggaccaaatgctaaatctgttcagagagagca
aagcttacactccttcatacgcttttctgtaggcgatgttttaaatatg
actgcttcctacatcgtaagtgcaattattcttttcatgcaacacccaac
acttataagcggaagaacacagaaacagctctagacaacaaaccttgtgg
accacagtgttaccagcatttggagggagcaaaggagtttgctgctgctc
tcaccgctgagcggataaagaccccaccaaaacgtccaggaggccgcaga
agaggacggcttcccaataacagtagcaggcccagcaccccaccattaa
tgtgctggaatcaaaggatacagacagtgatagggaagcagggactgaaa
cgggggggagagaacaatgataaagaagaagaagaagaaagatgaaact
tcgagctcctctgaagcaaattctcggtgtcaaacaccaataaagatgaa
gccaaatattgaacctcctgagaatgtggagtggagtggtgctgaagcct
caatgtttagagtcctcattggcacttactatgacaatttctgtgccatt
gctaggttaattgggaccaaaacatgtagacaggtgtatgagtttagagt
caaagaatctagcatcatagctccagctcccgctgaggatgtggatactc
ctccaaggaaaaagaagaggaaacaccggttgtgggctgcacactgcaga
aagatacagctgaaaaggacggctcctctaaccatgtttacaactatca
accctgtgatcatccacggcagccttgtgacagttcgtgcccttgtgtga
tagcacaaaattttgtgaaaagttttgtcaatgtagttcagagtgtcaa
aaccgctttccgggatgccgctgcaaagcacagtgcaacaccaagcagtg
cccgtgctacctggctgtccgagagtgtgaccctgacctctgtcttactt
gtggagccgctgaccattgggacagtaaaaatgtgtcctgcaagaactgc
agtattcagcggggctccaaaaagcatctattgctggcaccatctgacgt
ggcaggctggggattttttatcaaagatcctgtgcagaaaaatgaattca
tctcagaatactgtggagagattatttctcaagatgaagctgacagaaga
gggaaagtgtatgataaatcatgtgcagctttctgttcaacttgaacaa
tgattttgtggtggatgcaacccgcaagggtaacaaaattcgttttgcaa
atcattcggtaaatccaaactgctatgcaaaagttatgatggttaacggt
gatcacaggataggtattttttgccaagagagccatccagactggcgaaga
gctgtttttgattacagatacagccaggctgatgccctgaagtatgtcg
gcatcgaaagagaatggaaatcccttgacatctgctacctcctcccccc
tcctctgaaacagctgccttagcttcaggaaccctcgagtactgtgggcaa
tttagaaaaagaacatgcagtttgaaattctgaatttgcaaagtactgta
agaataatttatagtaatgagtttaaaaatcaacttttttattgccttctc
accagctgcaaagtgttttgtaccagtgaattttttgcaataatgcagtat
ggtacatttttcaactttgaataaagaatacttgaacttgtccttgttga
atc Full amino acid of EZH2, isoform a (GenBank
Accession No. NP_004447)
(SEQ ID NO: 3)
MGQTGKKSEKGPVCWRKRVKSEYMRLRQLKRFRRADEVKSMFSSNRQKIL
ERTEILNQEWKQRRIQPVHILTSVSSLRGTRECSVTSDLDFPTQVIPLKT
LNAVASVPIMYSWSPLOQNFMVEDETVLHNIPYMGDEVLDQDGTFIEELI
KNYDGKVHGDRECGFINDEIFVELVNALGQYNDDDDDDGDDPEEREEKQ
KDLEDHRDDKESRPPRKFPSDKIFEAISSMFPDKGTAEELKEKYKELTEQ
QLPGALPPECTPNIDGPNAKSVQREQSLHSFHTLFCRRCFKYDCFLHRKC
NYSFHATPNTYKRKNTETALDNKPCGPQCYQHLEGAKEFAAALTAERIKT
PPKRPGGRRRGRLPNNSSRPSTPTINVLESKDTDSDREAGTETGGENNDK
EEEEKKDETSSSSEANSRCQTPIKMKPNIEPPENVEWSGAEASMFRVLIG
TYYDNFCAIARLIGTKTCRQVYEFRVKESSIIAPAPAEDVDTPPRKKKRK
HRLWAAHCRKIQLKKDGSSNHVYNYQPCDHPRQPCDSSCPCVIAQNFCEK
FCQCSSECQNRFPGCRCKAQCNTKQCPCYLAVRECDPDLCLTCGAADHWD
SKNVSCKNCSIQRGSKKHLLLAPSDVAGWGIFIKDPVQKNEFISEYCGEI
ISQDEADRRGKVYDKYMCSFLFNLNNDFVVDATRKGNKIRFANHSVNPNC
YAKVMMVNGDHRIGIFAKRAIQTGEELFFDYRYSQADALKYVGIEREMEI
P mRNA sequence of human EZH2, transcript variant 2
(GenBank Accession No. NN_152998)
(SEQ ID NO: 4)
ggcggcgcttgattgggctggggggggccaaataaaagcgatggcgattgg
gctgccgcgtttggcgctcggtccggtcgcgtccgacacccggtgggact
cagaaggcagtggagcccggcggcggcggcggcggcgcgcgggggcgac
gcgcgggaacaacgcgagtcggcgcgcgggacgaagaataatcatgggcc
agactgggaagaaatctgagaagggaccagtttgttggcggaagcgtgta
aaatcagagtacatgcgactgagacagctcaagaggttcagacgagctga
tgaagtaaagagtatgtttagttccaatcgtcagaaaattttggaaagaa
cggaaatcttaaaccaagaatggaaacagcgaaggatacagcctgtgcac
atcctgacttctgtgagctcattgcgcgggactagggaggtggaagatga
aactgttttacataacattccttatatgggagatgaagtttagatcagg
atggtactttcattgaagaactaataaaaaattatgatgggaaagtacac
ggggatagagaatgtgggtttataaatgatgaaattttgtggagttggt
gaatgcccttggtcaatataatgatgatgacgatgatgatgatggagacg
atcctgaagaaagagaagaaaagcagaaagatctggaggatcaccgagat
gataaagaagccgcccacctcggaaatttccttctgataaaattttttga
agccatttcctcaatgtttccagataagggcacagcagaagaactaaagg
aaaaatataaagaactcaccgaacagcagctcccaggcgcacttcctcct -continued

```
gaatgtaccccaacatagatggaccaaatgctaaatctgttcagagaga gcaaagcttacactcctttcatacgcttttctgtaggcgatgttttaaat atgactgcttcctacatccttttcatgcaacacccaacacttataagcgg aagaacacagaaacagctctagacaacaaaccttgtggaccacagtgtta ccagcatttggagggagcaaaggagtttgctgctgctctcaccgctgagc ggataaagaccccaccaaaacgtccaggaggccgcagaagaggacggctt cccaataacagtagcaggcccagcaccccaccattaatgtgctggaatc aaaggatacagacagtgataggg aagcagggactgaaacgggggagaga acaatgataaagaagaagaagagaagaaagatgaaacttcgagctcctct gaagcaaattctcggtgtcaaacaccaataaagatgaagccaaatattga acctcctgagaatgtggagtggagtggtgctgaagcctcaatgtttagag tcctcattggcacttactatgacaatttctgtgccattgctaggttaatt gggaccaaaacatgtagacaggtgtatgagtttagagtcaaagaatctag catcatagctccagctcccgctgaggatgtggatactcctccaaggaaaa agaagaggaaacaccggttgtgggctgcacactgcagaaagatacagctg aaaaaggacggctcctctaaccatgtttacaactatcaaccctgtgatca tccacggcagccttgtgacagttcgtgccttgtgtgatagcacaaaatt tttgtgaaaagttttgtcaatgtagttcagagtgtcaaaaccgctttccg ggatgccgctgcaaagcacagtgcaacaccaagcagtgcccgtgctacct ggctgtccgagagtgtgaccctgacctctgtcttacttgtggagccgctg accattgggacagtaaaaatgtgtcctgcaagaactgcagtattcagcgg ggctccaaaaagcatctattgctggcaccatctgacgtggcaggctgggg gattttatcaaagatcctgtgcagaaaaatgaattcatctcagaatact gtggagagattatttctcaagatgaagctgacagaagagggaaagtgtat gataaatacatgtgcagctttctgttcaacttgaacaatgattttgtggt ggatgcaacccgcaagggtaacaaaattcgtttttgcaaatcattcggtaa atccaaactgctatgcaaaagttatgatggttaacggtgatcacaggata ggtattttgccaagagagccatccagactggcgaagagctgttttttga ttacagatacagccaggctgatgccctgaagtatgtcggcatcgaaagag aaatggaaatcccttgacatctgctacctcctccccctcctctgaaaca gctgccttagcttcaggaacctcgagtactgtgggcaatttagaaaaga acatgcagtttgaaattctgaatttgcaaagtactgtaagaataatttat agtaatgagtttaaaaatcaactttttattgccttctcaccagctgcaaa gtgttttgtaccagtgaatttttgcaataatgcagtatggtacattttc aactttgaataaagaatacttgaacttgtccttgttgaatc
```

Full amino acid of EZH2, isoform b (GenBank Accession No. NP_694543)

(SEQ ID NO: 5)
MGQTGKKSEKGPVCWRKRVKSEYMRLRQLKKFRRADEVKSMFSSNRQKIL
ERTEILNQEWKQRRIQPVHILTSVSSLRGTREVEDETVLHNIPYMGDEVL
DQDGTFIEELIKNYDGKVHGDRECGFINDEIFVELVNALGQYNDDDDDDD
GDDPEEREEKQKDLEDHRDDKESRPPRKFPSDKIFEAISSMFPDKGTAEE

LKEKYKELTEQQLPGALPPECTPNIDGPNAKSVQREQSLHSFHTLFCRRC
FKYDCFLHPFHATPNTYKRKNTETALDNKPCGPQCYQHLEGAKEFAAALT
AERIKTPPKRPGGRRRGRLPNNSSRPSTPTINVLESKDTDSDREAGTETG
GENNDKEEEEKKDETSSSSEANSRCQTPIKMKPNIEPPENVEWSGAEASM
FRVLIGTYYDNFCAIARLIGTKTCRQVYEFRVKESSIIAPAPAEDVDTPP
RKKKRKHRLWAAHCRKIQLKKDGSSNHVYNYQPCDHPRQPCDSSCPCVIA
QNFCEKFCQCSSECQNRFPGCRCKAQCNTKQCPCYLAVRECDPDLCLTCG
AADHWDSKNVSCKNCSIQRGSKKHLLLAPSDVAGWGIFIKDPVQKNEFIS
EY̲CGEIISQDEADRRGKVYDKYMCSFLFNLNNDFVVDATRKGNKIRFANH
SVNPNCYAKVMMVNGDHRIGIFAKRAIQTGEELFFDYRYSQADALKYVGI
EREMEIP

As mentioned above, the catalytic site of EZH2 is believed to reside in a conserved domain of the protein known as the SET domain. The amino acid sequence of the SET domain of EZH2 is provided by the following partial sequence spanning amino acid residues 613-726 of Swiss-Prot Accession No. Q15910 (SEQ ID NO: 1):

(SEQ ID NO:6)
HLLLAPSDVAGWGIFIKIDPVQKNEFISEY̲CGEIISQDEADRRGKVYDKY
MCSFLFNLNNDFVVDATRKGNKIRFANHSVNPNCYAKVMMVNGDHRIGIF
AKRAIQTGEELFFDY.

The tyrosine (Y) residue shown underlined in SEQ ID NO: 6 is Tyr641 (Y641) in Swiss-Prot Accession No. Q15910 (SEQ ID NO: 1).

The SET domain of GenBank Accession No. NP_004447 (SEQ ID NO: 3) spans amino acid residues 618-731 and is identical to SEQ ID NO:6. The tyrosine residue corresponding to Y641 in Swiss-Prot Accession No. Q15910 shown underlined in SEQ ID NO: 6 is Tyr646 (Y646) in GenBank Accession No. NP_004447 (SEQ ID NO: 3).

The SET domain of GenBank Accession No. NP_694543 (SEQ ID NO: 5) spans amino acid residues 574-687 and is identical to SEQ ID NO: 6. The tyrosine residue corresponding to Y641 in Swiss-Prot Accession No. Q15910 shown underlined in SEQ ID NO: 6 is Tyr602 (Y602) in GenBank Accession No. NP_694543 (SEQ ID NO: 5).

The nucleotide sequence encoding the SET domain of GenBank Accession No. NP_004447 is (SEQ ID NO: 7)
catctattgctggcaccatctgacgtggcaggctgggggatttttatcaa
agatcctgtgcagaaaaatgaattcatctcagaata̲c̲tgtggagagatta
tttctcaagatgaagctgacagaagagggaaagtgtatgataaatacatg
tgcagctttctgttcaacttgaacaatgattttgtggtggatgcaacccg
caagggtaacaaaattcgttttgcaaatcattcggtaaatccaaactgct
atgcaaaagttatgatggttaacggtgatcacaggataggtattttgcc
aagagagccatccagactggcgaagagctgttttttgattac, where the codon encoding Y641 is shown underlined.

For purposes of this application, amino acid residue Y641 of human EZH2 is to be understood to refer to the tyrosine residue that is or corresponds to Y641 in Swiss-Prot Accession No. Q15910.

Full amino acid sequence of Y641 mutant EZH2
(SEQ ID NO: 8)
MGQTGKKSEKGPVCWRKRVKSEYMRLRQLKRFRRADEVKSMFSSNRQKIL

ERTEILNQEWKQRRIQPVHILTSVSSLRGTRECSVTSDLDFPTQVIPLKT

LNAVASVPIMYSWSPLQQNFMVEDETVLHNIPYMGDEVLDQDGTFIEELI

KNYDGKVHGDRECGFINDEIFVELVNALGQYNDDDDDDGDDPEEREEKQ

KDLEDHRDDKESRPPRKFPSDKIFEAISSMFPDKGTAEELKEKYKELTEQ

QLPGALPPECTPNIDGPNAKSVQREQSLHSFHTLFCRRCFKYDCFLHPFH

ATPNTYKRKNTETALDNKPCGPQCYQHLEGAKEFAAALTAERIKTPPKRP

GGRRRGRLPNNSSRPSTPTINVLESKDTDSDREAGTETGGENNDKEEEEK

KDETSSSSEANSRCQTPIKMKPNIEPPENVEWSGAEASMFRVLIGTYYDN

FCAIARLIGTKTCRQVYEFRVKESSIIAPAPAEDVDTPPRKKKRKHRLWA

AHCRKIQLKKDGSSNHVYNYQPCDHPRQPCDSSCPCVIAQNFCEKFCQCS

SECQNRFPGCRCKAQCNTKQCPCYLAVRECDPDLCLTCGAADHWDSKNVS

CKNCSIQRGSKKHLLLAPSDVAGWGIFIKDPVQKNEFISEXCGEIISQDE

ADRRGKVYDKYMCSFLFNLNNDFVVDATRKGNKIRFANHSVNPNCYAKVM

MVNGDHRIGIFAKRAIQTGEELFFDYRYSQADALKYVGIEREMEIP

Wherein x can be any amino acid residue other than tyrosine (Y)

Also for purposes of this application, a Y641 mutant of human EZH2, and, equivalently, a Y641 mutant of EZH2, is to be understood to refer to a human EZH2 in which the amino acid residue corresponding to Y641 of wild-type human EZH2 is substituted by an amino acid residue other than tyrosine.

In one embodiment the amino acid sequence of a Y641 mutant of EZH2 differs from the amino acid sequence of wild-type human EZH2 only by substitution of a single amino acid residue corresponding to Y641 of wild-type human EZH2 by an amino acid residue other than tyrosine.

In one embodiment the amino acid sequence of a Y641 mutant of EZH2 differs from the amino acid sequence of wild-type human EZH2 only by substitution of phenylalanine (F) for the single amino acid residue corresponding to Y641 of wild-type human EZH2. The Y641 mutant of EZH2 according to this embodiment is referred to herein as a Y641F mutant or, equivalently, Y641F.

Y641F
(SEQ ID NO: 9)
MGQTGKKSEKGPVCWRKRVKSEYMRLRQLKRFRRADEVKSMFSSNRQKIL

ERTEILNQEWKQRRIQPVHILTSVSSLRGTRECSVTSDLDFPTQVIPLKT

LNAVASVPIMYSWSPLQQNFMVEDETVLHNIPYMGDEVLDQDGTFIEELI

KNYDGKVHGDRECGFINDEIFVELVNALGQYNDDDDDDGDDPEEREEKQ

KDLEDHRDDKESRPPRKFPSDKIFEAISSMFPDKGTAEELKEKYKELTEQ

QLPGALPPECTPNIDGPNAKSVQREQSLHSFHTLFCRRCFKYDCFLHPFH

ATPNTYKRKNTETALDNKPCGPQCYQHLEGAKEFAAALTAERIKTPPKRP

GGRRRGRLPNNSSRPSTPTINVLESKDTDSDREAGTETGGENNDKEEEEK

KDETSSSSEANSRCQTPIKMKPNIEPPENVEWSGAEASMFRVLIGTYYDN

FCAIARLIGTKTCRQVYEFRVKESSIIAPAPAEDVDTPPRKKKRKHRLWA

AHCRKIQLKKDGSSNHVYNYQPCDHPRQPCDSSCPCVIAQNFCEKFCQCS

SECQNRFPGCRCKAQCNTKQCPCYLAVRECDPDLCLTCGAADHWDSKNVS

CKNCSIQRGSKKHLLLAPSDVAGWGIFIKDPVQKNEFISEFCGEIISQDE

ADRRGKVYDKYMCSFLFNLNNDFVVDATRKGNKIRFANHSVNPNCYAKVM

MVNGDHRIGIFAKRAIQTGEELFFDYRYSQADALKYVGIEREMEIP

In one embodiment the amino acid sequence of a Y641 mutant of EZH2 differs from the amino acid sequence of wild-type human EZH2 only by substitution of histidine (H) for the single amino acid residue corresponding to Y641 of wild-type human EZH2. The Y641 mutant of EZH2 according to this embodiment is referred to herein as a Y641H mutant or, equivalently, Y641H.

Y641H
(SEQ ID NO: 10)
MGQTGKKSEKGPVCWRKRVKSEYMRLRQLKRFRRADEVKSMFSSNRQKIL

ERTEILNQEWKQRRIQPVHILTSVSSLRGTRECSVTSDLDFPTQVIPLKT

LNAVASVPIMYSWSPLQQNFMVEDETVLHNIPYMGDEVLDQDGTFIEELI

KNYDGKVHGDRECGFINDEIFVELVNALGQYNDDDDDDGDDPEEREEKQ

KDLEDHRDDKESRPPRKFPSDKIFEAISSMFPDKGTAEELKEKYKELTEQ

QLPGALPPECTPNIDGPNAKSVQREQSLHSFHTLFCRRCFKYDCFLHPFH

ATPNTYKRKNTETALDNKPCGPQCYQHLEGAKEFAAALTAERIKTPPKRP

GGRRRGRLPNNSSRPSTPTINVLESKDTDSDREAGTETGGENNDKEEEEK

KDETSSSSEANSRCQTPIKMKPNIEPPENVEWSGAEASMFRVLIGTYYDN

FCAIARLIGTKTCRQVYEFRVKESSIIAPAPAEDVDTPPRKKKRKHRLWA

AHCRKIQLKKDGSSNHVYNYQPCDHPRQPCDSSCPCVIAQNFCEKFCQCS

SECQNRFPGCRCKAQCNTKQCPCYLAVRECDPDLCLTCGAADHWDSKNVS

CKNCSIQRGSKKHLLLAPSDVAGWGIFIKDPVQKNEFISEHCGEIISQDE

ADRRGKVYDKYMCSFLFNLNNDFVVDATRKGNKIRFANHSVNPNCYAKVM

MVNGDHRIGIFAKRAIQTGEELFFDYRYSQADALKYVGIEREMEIP

In one embodiment the amino acid sequence of a Y641 mutant of EZH2 differs from the amino acid sequence of wild-type human EZH2 only by substitution of asparagine (N) for the single amino acid residue corresponding to Y641 of wild-type human EZH2. The Y641 mutant of EZH2 according to this embodiment is referred to herein as a Y641N mutant or, equivalently, Y641N.

Y641N
(SEQ ID NO: 11)
MGQTGKKSEKGPVCWRKRVKSEYMRLRQLKRFRRADEVKSMFSSNRQKIL

ERTEILNQEWKQRRIQPVHILTSVSSLRGTRECSVTSDLDFPTQVIPLKT

LNAVASVPIMYSWSPLQQNFMVEDETVLHNIPYMGDEVLDQDGTFIEELI

KNYDGKVHGDRECGFINDEIFVELVNALGQYNDDDDDDGDDPEEREEKQ

-continued
KDLEDHRDDKESRPPRKFPSDKIFEAISSMFPDKGTAEELKEKYKELTEQ

QLPGALPPECTPNIDGPNAKSVQREQSLHSFHTLFCRRCFKYDCFLHPFH

ATPNTYKRKNTETALDNKPCGPQCYQHLEGAKEFAAALTAERIKTPPKRP

GGRRRGRLPNNSSRPSTPTINVLESKDTDSDREAGTETGGENNDKEEEEK

KDETSSSSEANSRCQTPIKMKPNIEPPENVEWSGAEASMFRVLIGTYYDN

FCAIARLIGTKTCRQVYEFRVKESSIIAPAPAEDVDTPPRKKKRKHRLWA

AHCRKIQLKKDGSSNHVYNYQPCDHPRQPCDSSCPCVIAQNFCEKFCQCS

SECQNRFPGCRCKAQCNTKQCPCYLAVRECDPDLCLTCGAADHWDSKNVS

CKNCSIQRGSKKHLLLAPSDVAGWGIFIKDPVQKNEFISENCGEIISQDE

ADRRGKVYDKYMCSFLFNLNNDFVVDATRKGNKIRFANHSVNPNCYAKVM

MVNGDHRIGIFAKRAIQTGEELFFDYRYSQADALKYVGIEREMEIP

In one embodiment the amino acid sequence of a Y641 mutant of EZH2 differs from the amino acid sequence of wild-type human EZH2 only by substitution of serine (S) for the single amino acid residue corresponding to Y641 of wild-type human EZH2. The Y641 mutant of EZH2 according to this embodiment is referred to herein as a Y641S mutant or, equivalently, Y641S.

Y641S
(SEQ ID NO: 12)
MGQTGKKSEKGPVCWRKRVKSEYMRLRQLKRFRRADEVKSMFSSNRQKIL

ERTEILNQEWKQRRIQPVHILTSVSSLRGTRECSVTSDLDFPTQVIPLKT

LNAVASVPIMYSWSPLQQNFMVEDETVLHNIPYMGDEVLDQDGTFIEELI

KNYDGKVHGDRECGFINDEIFVELVNALGQYNDDDDDDGDDPEEREEKQ

KDLEDHRDDKESRPPRKFPSDKIFEAISSMFPDKGTAEELKEKYKELTEQ

QLPGALPPECTPNIDGPNAKSVQREQSLHSFHTLFCRRCFKYDCFLHPFH

ATPNTYKRKNTETALDNKPCGPQCYQHLEGAKEFAAALTAERIKTPPKRP

GGRRRGRLPNNSSRPSTPTINVLESKDTDSDREAGTETGGENNDKEEEEK

KDETSSSSEANSRCQTPIKMKPNIEPPENVEWSGAEASMFRVLIGTYYDN

FCAIARLIGTKTCRQVYEFRVKESSIIAPAPAEDVDTPPRKKKRKHRLWA

AHCRKIQLKKDGSSNHVYNYQPCDHPRQPCDSSCPCVIAQNFCEKFCQCS

SECQNRFPGCRCKAQCNTKQCPCYLAVRECDPDLCLTCGAADHWDSKNVS

CKNCSIQRGSKKHLLLAPSDVAGWGIFIKDPVQKNEFISESCGEIISQDE

ADRRGKVYDKYMCSFLFNLNNDFVVDATRKGNKIRFANHSVNPNCYAKVM

MVNGDHRIGIFAKRAIQTGEELFFDYRYSQADALKYVGIEREMEIP

The tolerance for multiple Y641 mutations in EZH2 suggests that a release of steric crowding may allow greater access for proper alignment of the larger dimethyl lysine as the substrate for the di-to-tri methylation reaction. Crystallographic analysis of the protein methyltransferases SET7/9 and G9a reveals that the side chain hydroxyls of the active site tyrosine residues are involved in H-bonding interactions directly with the amine of the methyl-accepting lysine, or indirectly through an intervening water molecule. While the larger active site of the Y641 mutants is favorable for di- and tri-methylation, the loss of the tyrosine hydroxyl hydrogen bond acceptor may result in an unfavorable orientation of the active site for initial methyl transfer to the lysine amine.

The implications of the present results for human disease are made clear by the data summarized in Table 1 (see below).

Cells heterozygous for EZH2 would be expected to display a malignant phenotype due to the efficient formation of H3-K27me1 by the WT enzyme and the efficient, subsequent transition of this progenitor species to H3-K27me2, and, especially, H3-K27me3, by the mutant enzyme form(s).

It has been reported that H3-K27me1 formation is not exclusively dependent on WT-EZH2 catalysis. Knockout studies of EZH2 and of another PRC2 subunit, EED, have demonstrated H3-K27me1 formation can be catalyzed by PRC2 complexes containing either EZH2 or the related protein EZH1 as the catalytic subunit. Shen, X. et al. (2008) *Mol Cell* 32:491-502. Hence, catalytic coupling between the mutant EZH2 species and PRC2 complexes containing either WT-EZH2 or WT-EZH1 would suffice to augment H3-K27me2/3 formation, and thus produce the attendant malignant phenotype. The data therefore suggest that the malignant phenotype of follicular lymphoma (FL) and diffuse large B-cell lymphoma (DLBCL) of the germinal center B cell (GCB) subtype, associated with expression of mutant forms of EZH2, is the result of an overall gain of function with respect to formation of the trimethylated form of H3-K27. This interpretation of the data also helps to reconcile the existence of cancer-associated overexpression of EZH2 or PRC2 associated proteins (e.g., PHF19/PCL3) and also loss-of-function genotypes for the histone H3-K27 demethylase UTX. Loss of UTX activity would be enzymatically equivalent to a gain of function for EZH2, in either situation resulting in greater steady state levels of tri-methylated H3-K27 in cancer cells (FIGS. 4A-D).

The mono-, di-, and tri-methylation states of histone H3-K27 are associated with different functions in transcriptional control. Histone H3-K27 monomethylation is associated with active transcription of genes that are poised for transcription. Cui et al. (2009) *Cell Stem Cell* 4:80-93; Barski (2007) *Cell* 129:823-37. In contrast, trimethylation of histone H3-K27 is associated with either transcriptionally repressed genes or genes that are poised for transcription when histone H3-K4 trimethylation is in cis. Cui et al. (supra); Kirmizis et al. (2007) *Genes Dev* 18:1592-1605; Bernstein et al. (2006) *Cell* 125:315-26. Taken together, alterations in the PRC2 complex activity reported in cancer, including the Y641 mutation of EZH2, are predicted to result in an increase in the trimethylated state of histone H3-K27 and thus to result in transcriptional repression.

Figure 9A:
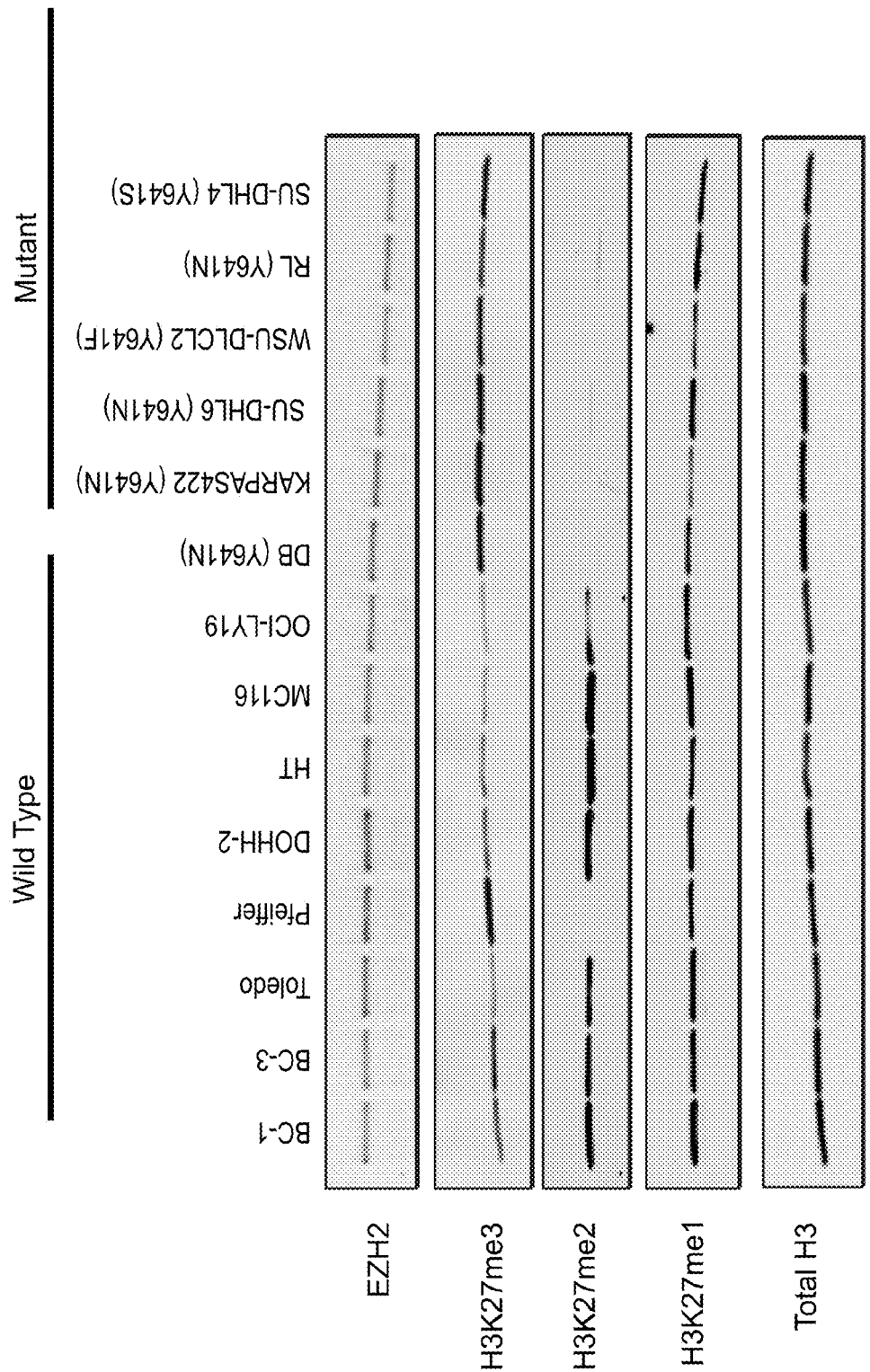
FIGS. 9A and 9B depict a Western Blot analysis of relative levels of H3-K27me1, me2 and me3 in a cell line pane, including multiple DLBCL lines expressing WT or Y641 mutant EZH2.
Figure 9B:
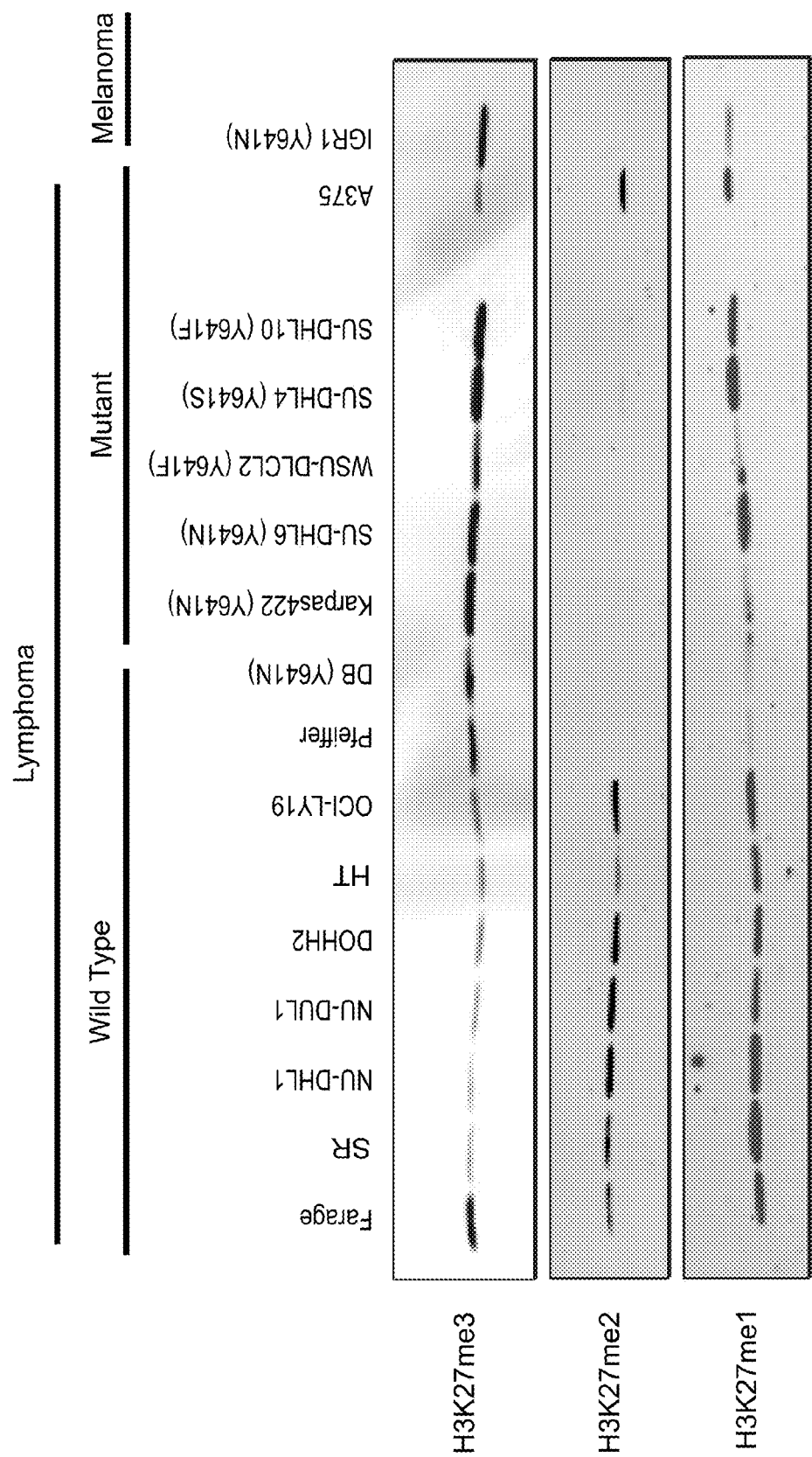
Figure 10:
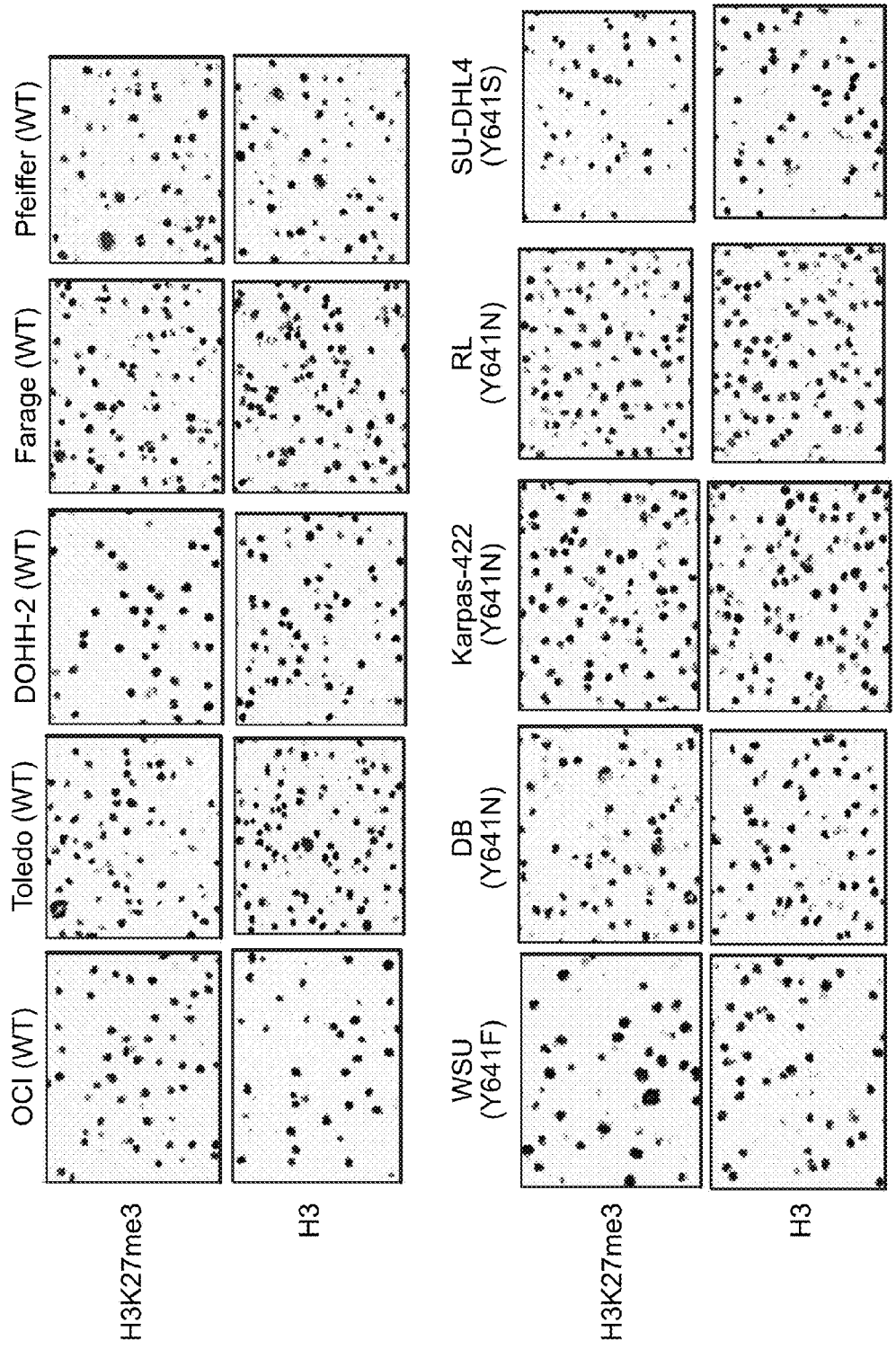
FIG. 10 depicts an immunocytochemistry analysis of H3 and H3-K27me3 levels in a panel of WT and Y641 mutant lymphoma cell lines. Cell pellets from the indicated cell lines were fixed and embedded in paraffin. Slides were prepared and levels of H3 and H3-K27me3 were evaluated by immunocytochemistry using antibodies to histone H3, or H3-K27me3.
Figure 11:
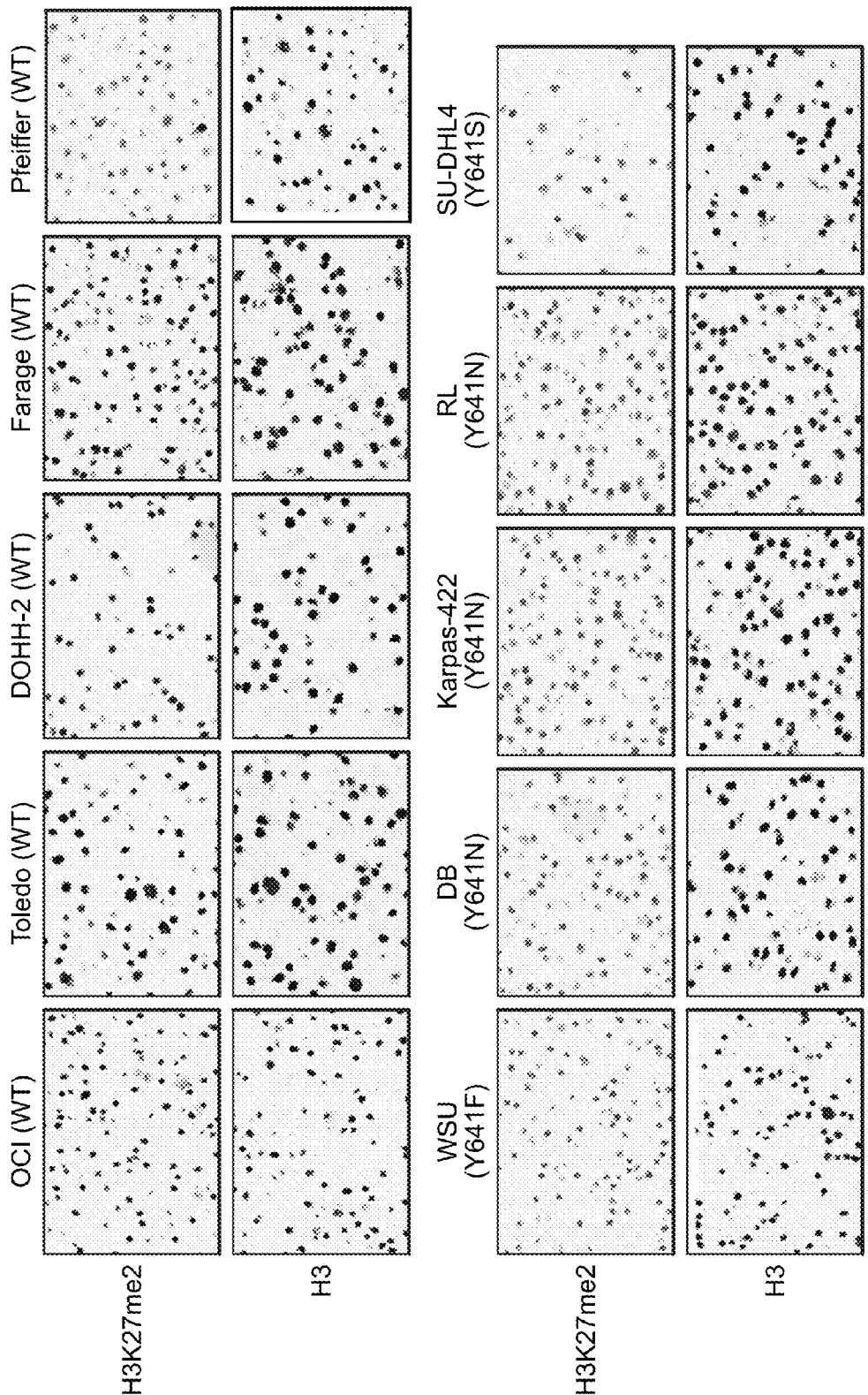
FIG. 11 depicts an immunocytochemistry analysis of H3 and H3-K27me2 levels in a panel of WT and Y641 mutant lymphoma cell lines. Cell pellets from the indicated cell lines were fixed and embedded in paraffin. Slides were prepared and levels of H3 and H3-K27me2 were evaluated by immunocytochemistry using antibodies to histone H3, or H3-K27me2.
Figure 13:
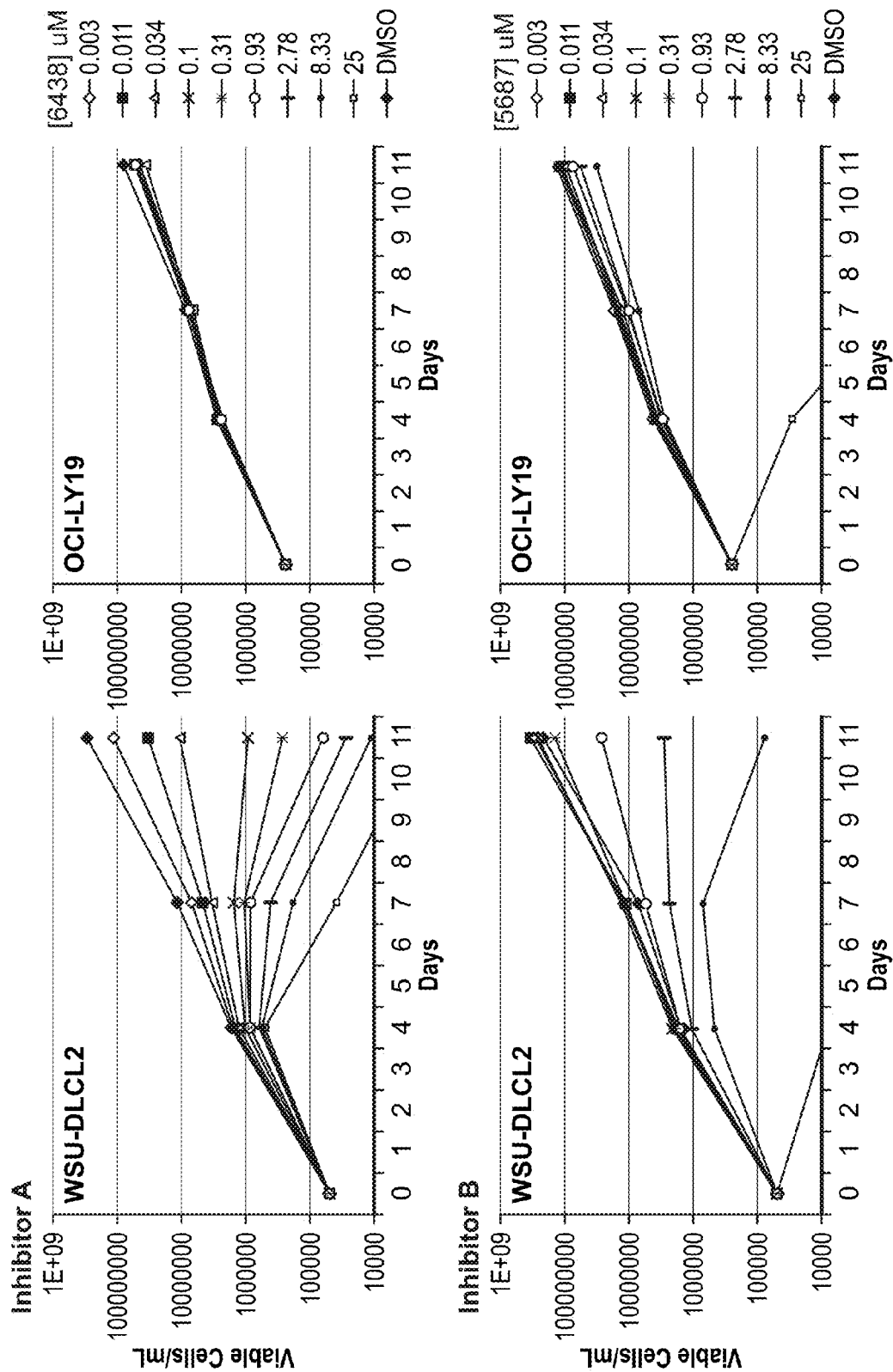
FIG. 13 is a graph showing that the EZH2 inhibitors can block proliferation of a Y641 mutant WSU-DLCL2 cells, but has little effect on non Y641 mutant OCI-LY19 cells. Cells were incubated in the presence of increasing concentrations of EZH2 inhibitor A or B for eleven days. Vehicle treated (DMSO) cells were included as controls. Cell number and viability was determined using the Guava Viacount assay in a Guava EasyCyte Plus instrument. Cells were split and media and compound was replenished every 3-4 days.
Figure 14B:
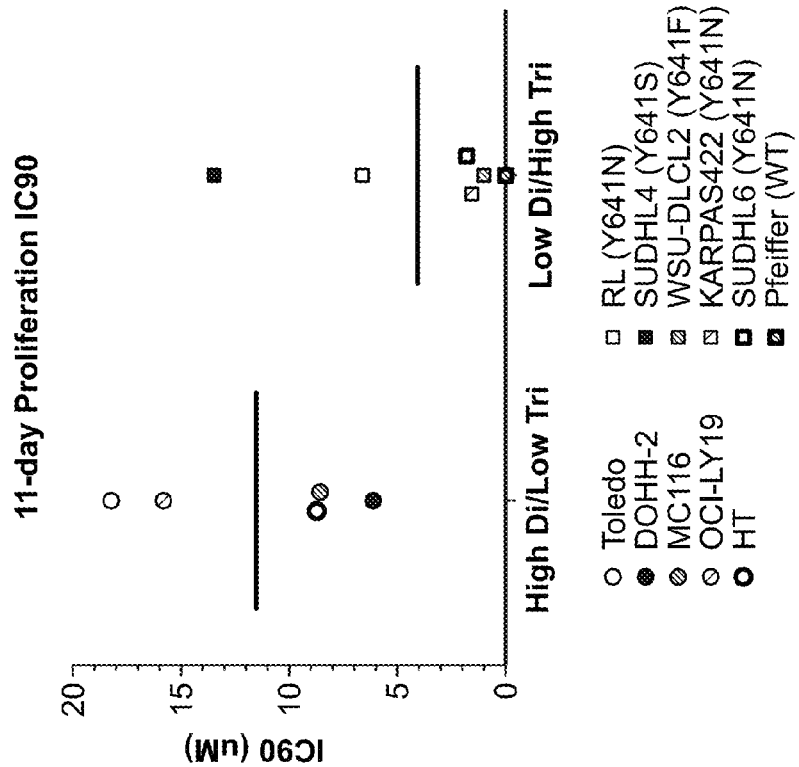
FIGS. 14A and 14B are a series of graphs showing the presence of an EZH2 (Y641) mutation and/or high H3-K27me3 and low H3-K27me2 levels predict sensitivity to EZH2 inhibitors. Cell lines were maintained in the presence of increasing concentrations of one EZH2 inhibitor up to 25 µM. Viable cells counts were used to derive $IC_{90}$ values after 11 days of treatment. Results are plotted with cell lines segregated according to EZH2 mutational status (A), or segregated according to H3-K27me2 and H3-K27me3 levels (B). In both plots, the line shows the average IC90 values from the indicated cell line group.

Another discovery of the present invention is that cells expressing Y641 mutant EZH2 are, in general, more sensitive to small molecule EZH2 inhibitors than cells expressing WT EZH2. Specifically, cells expressing Y641 mutant EZH2 show reduced growing, dividing or proliferation, or even undergo apoptosis or necrosis after the treatment of EZH2 inhibitors. In contrast, cells expressing WT EZH2 are not responsive to the anti-proliferative effect of the EZH2 inhibitors (FIGS. 13 and 14). Another surprising discovery of the present invention is that it is possible for cells expressing WT EZH2 to display a similar methylation status of histone H3-K27 as cells expressing Y641 EZH2, and that this methylation status can also correlate with sensitivity to an EZH2 inhibitor independently of EZH2 mutational status. In general, global H3-K27me3 levels are similar or higher in Y641 mutant containing cell lines than in cell lines expressing WT EZH2; however levels of H3-K27me2 are dramatically lower in EZH2 Y641 mutant cell lines and certain wild type cell lines, such as the Pfeiffer cell line than in other wild type cell lines (FIGS. 9, 10 and 11). Thus the ratio of H3-K27me2/me3 signal in Y641 mutant lines and the Pfeiffer cell line is much lower than that observed in other WT lines. The present data further demonstrate that cell lines with low H3-K27me2 signal and similar or higher H3-K27me3 signal relative to typical WT EZH2 expressing cells lines are more sensitive to small molecule EZH2 inhibitors. Specifically, cells with a low H3-K27me2 signal and a normal or high H3K27me3 signal stop dividing or even die after treatment with EZH2 inhibitors (FIGS. 9, 10, 11, 13, and 14). In contrast, cells with a higher ratio of H3-K27me2/me3 signal are not responsive to the anti-proliferative effect of the EZH2 inhibitors (FIGS. 9, 10, 11, 13, and 14). The instant invention provides previously unknown and unexpected results that identifying EZH2 Y641 mutations in patient tumors and/or detecting low levels of H3-K27me2 and normal or high levels of H3-K27me3 relative to a control, through use of techniques such as western blot, MS or IHC in a patient can be used to identify which patient will respond to an EZH2 inhibitor treatment.

EZH2 and other protein methyltransferases have been suggested to be attractive targets for drug discovery. Copeland et al. (2009) *Nat Rev Drug Discov* 8:724-32; Copeland et al. (2010) *Curr Opin Chem Biol* 14(4):505-10; Pollock et al. (2010) *Drug Discovery Today: Therapeutic Strategies* 6(1): 71-9. The present data also suggest an experimental strategy for development of FL and GCB lymphoma-specific drugs. As the differences in substrate recognition between the WT and disease-associated mutants derive from transition state interactions, small molecule inhibitors that selectively mimic the transition state of the mutant EZH2 over that of the WT enzyme should prove to be effective in blocking H3-K27 methylation in mutation-bearing cells. Inhibitors of this type would be expected to display a large therapeutic index, as target-mediated toxicity would be minimal for any cells bearing only the WT enzyme. Transition state mimicry has proved to be an effective strategy for drug design in many disease areas. See, for example, Copeland, R. A. *Enzymes: A Practical Introduction to Structure, Mechanism and Data Analysis*. 2nd ed, (Wiley, 2000).

The present results point to a previously unrecognized, surprising dependency on enzymatic coupling between enzymes that perform H3-K27 mono-methylation and certain mutant forms of EZH2 for pathogenesis in follicular lymphoma and diffuse large B-cell lymphoma. While not intending to be bound by any one theory, it is believed the data constitute the first example of a human disease that is dependent on such coupling of catalytic activity between normal (WT) and disease-associated mutant (Y641) enzymes.

An aspect of the invention is a method for inhibiting in a subject conversion of H3-K27 to trimethylated H3-K27. The inhibition can involve inhibiting in a subject conversion of unmethylated H3-K27 to monomethylated H3-K27, conversion of monomethylated H3-K27 to dimethylated H3-K27, conversion of dimethylated H3-K27 to trimethylated H3-K27, or any combination thereof, including, for example, conversion of monomethylated H3-K27 to dimethylated H3-K27 and conversion of dimethylated H3-K27 to trimethylated H3-K27. As used herein, unmethylated H3-K27 refers to histone H3 with no methyl group covalently linked to the amino group of lysine 27. As used herein, monomethylated H3-K27 refers to histone H3 with a single methyl group covalently linked to the amino group of lysine 27. Monomethylated H3-K27 is also referred to herein as H3-K27me1. As used herein, dimethylated H3-K27 refers to histone H3 with two methyl groups covalently linked to the amino group of lysine 27. Dimethylated H3-K27 is also referred to herein as H3-K27me2. As used herein, trimethylated H3-K27 refers to histone H3 with three methyl groups covalently linked to the amino group of lysine 27. Trimethylated H3-K27 is also referred to herein as H3-K27me3.

Histone H3 is a 136 amino acid long protein, the sequence of which is known. See, for example, GenBank Accession No. CAB02546, the contents of which is incorporated herein by reference. As disclosed further herein, in addition to full-length histone H3, peptide fragments of histone H3 comprising the lysine residue corresponding to K27 of full-length histone H3 can be used as substrate for EZH2 (and likewise for mutant forms of EZH2) to assess conversion of H3-K27m1 to H3-K27m2 and conversion of H3-K27m2 to H3-K27m3. In one embodiment, such peptide fragment corresponds to amino acid residues 21-44 of histone H3. Such peptide fragment has the amino acid sequence LATKAARK-SAPATGGVKKPHRYRP (SEQ ID NO: 13).

The method involves administering to a subject expressing a Y641 mutant of EZH2 a therapeutically effective amount of an inhibitor of EZH2, wherein the inhibitor inhibits histone methyltransferase activity of EZH2, thereby inhibiting conversion of H3-K27 to trimethylated H3-K27 in the subject. In one embodiment a subject expressing a Y641 mutant of EZH2 refers to a subject having a detectable amount of a Y641 mutant EZH2 polypeptide. In one embodiment a subject expressing a Y641 mutant of EZH2 refers to a subject having a detectable amount of a nucleic acid encoding a Y641 mutant EZH2 polypeptide.

A Y641 mutant EZH2 polypeptide can be detected using any suitable method. For example, a Y641 mutant EZH2 polypeptide can be detected using an antibody that binds specifically to the Y641 mutant EZH2 polypeptide or to a peptide fragment that is characteristic of the Y641 mutant EZH2 polypeptide. A peptide fragment that is characteristic of the Y641 mutant EZH2 polypeptide may include, for example, a SET domain as provided in SEQ ID NO: 6, except for substitution of Y641 by an amino acid residue other than tyrosine. In another embodiment, a peptide fragment that is characteristic of the Y641 mutant EZH2 polypeptide may include, for example, a 10-113 amino acid fragment of the SET domain as provided in SEQ ID NO: 6, except for substitution of Y641 by an amino acid residue other than tyrosine, provided that the fragment includes the amino acid residue corresponding to Y641. It is expected that the epitope for such antibody includes the amino acid residue corresponding to Y641 of wild-type EZH2. An antibody is considered to bind specifically to the Y641 mutant EZH2 polypeptide or to a peptide fragment that is characteristic of the Y641 mutant EZH2 polypeptide if it binds to that mutant EZH2 polypeptide or peptide fragment thereof but not to the corresponding wild-type EZH2 polypeptide or peptide fragment thereof. In one embodiment, such antibody is considered to bind specifically to the Y641 mutant EZH2 polypeptide or to a peptide fragment that is characteristic of the Y641 mutant EZH2 polypeptide if it binds to that mutant EZH2 polypeptide or peptide fragment thereof with an affinity that is at least ca. 100-fold greater than for the corresponding wild-type EZH2 polypeptide or peptide fragment thereof. In one embodiment, such antibody is considered to bind specifically to the Y641 mutant EZH2 polypeptide or to a peptide fragment that is characteristic of the Y641 mutant EZH2 polypeptide if it binds to that mutant EZH2 polypeptide or peptide fragment thereof with an affinity that is at least ca. 1000-fold greater than for the corresponding wild-type EZH2 polypeptide or peptide fragment thereof. The antibody can be used, for example, in an enzyme-linked immunosorbent assay (ELISA) or Western blot assay.

In one embodiment the antibody is a monoclonal antibody. A monoclonal antibody can be prepared according to conventional methods well known in the art. See, for example, Köhler and Milstein (1975) *Nature* 256 (5517):495-7.

As another example, a Y641 mutant EZH2 polypeptide can be detected using mass spectrometry (MS), e.g., electrospray ionization coupled with time-of-flight (ESI-TOF) or matrix-assisted laser desorption/ionization coupled with time-of-flight (MALDI-TOF). Such methods are well known in the art. The analysis will involve identification of one or more peptide fragments comprising the mutation of interest, for example, a peptide 12 to 24 amino acids long comprising a sequence spanning the amino acid corresponding to Y641 in wild-type EZH2.

A nucleic acid encoding a Y641 mutant EZH2 polypeptide or a peptide fragment that is characteristic of the Y641 mutant EZH2 polypeptide can be detected using any suitable method. For example, a nucleic acid encoding a Y641 mutant EZH2 polypeptide can be detected using whole-genome resequencing or target region resequencing (the latter also known as targeted resequencing) using suitably selected sources of DNA and polymerase chain reaction (PCR) primers in accordance with methods well known in the art. See, for example, Bentley (2006) *Curr Opin Genet Dev.* 16:545-52, and Li et al. (2009) *Genome Res* 19:1124-32. The method typically and generally entails the steps of genomic DNA purification, PCR amplification to amplify the region of interest, cycle sequencing, sequencing reaction cleanup, capillary electrophoresis, and data analysis. High quality PCR primers to cover region of interest are designed using in silico primer design tools. Cycle sequencing is a simple method in which successive rounds of denaturation, annealing, and extension in a thermal cycler result in linear amplification of extension products. The products are typically terminated with a fluorescent tag that identifies the terminal nucleotide base as G, A, T, or C. Unincorporated dye terminators and salts that may compete for capillary electrophoretic injection are removed by washing. During capillary electrophoresis, the products of the cycle sequencing reaction migrate through capillaries filled with polymer. The negatively charged DNA fragments are separated by size as they move through the capillaries toward the positive electrode. After electrophoresis, data collection software creates a sample file of the raw data. Using downstream software applications, further data analysis is performed to translate the collected color data images into the corresponding nucleotide bases. Alternatively or in addition, the method may include the use of microarray-based targeted region genomic DNA capture and/or sequencing. Kits, reagents, and methods for selecting appropriate PCR primers and performing resequencing are commercially available, for example, from Applied Biosystems, Agilent, and NimbleGen (Roche Diagnostics GmbH). Methods such as these have been used to detect JAK2 and myeloproliferative leukemia gene (MPL) mutations and to diagnose polycythemia vera, essential thrombocythemia, and idiopathic myelofibrosis. For use in the instant invention, PCR primers may be selected so as to amplify, for example, at least a relevant portion of SEQ ID NO: 7 (above).

Alternatively or in addition, a nucleic acid encoding a Y641 mutant EZH2 polypeptide may be detected using a Southern blot in accordance with methods well known in the art. In one embodiment a DNA sequence encoding a Y641 mutant EZH2 polypeptide is detected using nucleic acid hybridization performed under highly stringent conditions. A nucleic acid probe is selected such that its sequence is complementary to a target nucleic acid sequence that includes a codon for the mutant amino acid corresponding to Y641 of wild-type EZH2.

A sequence-specific probe is combined with a sample to be tested under highly stringent conditions. The term "highly stringent conditions" as used herein refers to parameters with which the art is familiar. Nucleic acid hybridization parameters may be found in references that compile such methods, e.g., J. Sambrook, et al., eds., *Molecular Cloning: A Laboratory Manual*, Second Edition, Cold Spring Harbor Laboratory Press, Cold Spring Harbor, N.Y., 1989, or F. M. Ausubel, et al., eds., *Current Protocols in Molecular Biology*, John Wiley & Sons, Inc., New York. More specifically, highly stringent conditions, as used herein, refers, for example, to hybridization at 65° C. in hybridization buffer (3.5×SSC, 0.02% Ficoll, 0.02% polyvinyl pyrrolidone, 0.02% bovine serum albumin (BSA), 2.5 mM $NaH_2PO_4$ (pH 7), 0.5% SDS, 2 mM EDTA). SSC is 0.15 M sodium chloride/0.015 M sodium citrate, pH 7; SDS is sodium dodecyl sulphate; and EDTA is ethylenediaminetetraacetic acid. After hybridization, the membrane upon which the DNA is transferred is washed, for example, in 2×SSC at room temperature and then at 0.1-0.5×SSC/0.1×SDS at temperatures up to 68° C.

There are other conditions, reagents, and so forth that can be used, which result in a similar degree of stringency. The skilled artisan will be familiar with such conditions, and thus they are not given here. It will be understood, however, that the skilled artisan will be able to manipulate the conditions in a manner to permit the clear identification of EZH2-associated nucleic acids of the invention, including, in particular, nucleic acids encoding Y641 mutants of EZH2 (e.g., by using lower stringency conditions). The skilled artisan also is familiar with the methodology for screening cells and libraries for expression of such molecules, which then are routinely isolated, followed by isolation of the pertinent nucleic acid molecule and sequencing.

The subject is administered a therapeutically effective amount of an inhibitor of EZH2. As used herein, an inhibitor of EZH2 refers, generally, to a small molecule, i.e., a molecule of molecular weight less than about 1.5 kilodaltons (kDa), which is capable of interfering with the histone methyltransferase enzymatic activity of EZH2.

In one embodiment the inhibitor of EZH2 inhibits histone methyltransferase activity of wild-type EZH2. In one embodiment the inhibitor of EZH2 inhibits histone methyltransferase activity of the Y641 mutant of EZH2. In one embodiment the inhibitor of EZH2 inhibits histone methyltransferase activity of wild-type EZH2 and histone methyltransferase activity of the Y641 mutant of EZH2. In one embodiment the inhibitor of EZH2 selectively inhibits histone methyltransferase activity of the Y641 mutant of EZH2.

As disclosed herein, certain Y641 mutants of EZH2 are relatively poor catalysts for conversion of unmethylated H3-K27 to H3-K27me1 and yet unexpectedly effective catalysts for conversion of H3-K27me2 to H3-K27me3. Conversely, wild-type EZH2 is a relatively effective catalyst for conversion of unmethylated H3-K27 to H3-K27me1 and yet unexpectedly ineffective catalyst for conversion of H3-K27me2 to H3-K27me3. This is important because mono-, di- and tri-methylated states of H3-K27 exhibit different functions in transcriptional control. For example, H3-K27me1 is associated with active transcription of genes that are poised for transcription, while H3-K27me3 is associated with transcriptionally repressed genes or genes that are poised for transcription when H3-K4 trimethylation is in cis. Thus, selective inhibition of histone methyltransferase activity of the Y641 mutant of EZH2 effects selective inhibition of production of the trimethylated form of H3-K27, thereby favoring transcription associated with H3-K27me1 and disfavoring repression of transcription associated with H3-K27me3.

An inhibitor of EZH2 "selectively inhibits" histone methyltransferase activity of the Y641 mutant of EZH2 when it inhibits histone methyltransferase activity of the Y641 mutant of EZH2 more effectively than it inhibits histone methyltransferase activity of wild-type EZH2. For example, in one embodiment the selective inhibitor has an IC50 for the Y641 mutant of EZH2 that is at least 40 percent lower than the IC50 for wild-type EZH2. In one embodiment the selective inhibitor has an IC50 for the Y641 mutant of EZH2 that is at least 50 percent lower than the IC50 for wild-type EZH2. In one embodiment the selective inhibitor has an IC50 for the Y641 mutant of EZH2 that is at least 60 percent lower than the IC50 for wild-type EZH2. In one embodiment the selective inhibitor has an IC50 for the Y641 mutant of EZH2 that is at least 70 percent lower than the IC50 for wild-type EZH2. In one embodiment the selective inhibitor has an IC50 for the Y641 mutant of EZH2 that is at least 80 percent lower than the IC50 for wild-type EZH2. In one embodiment the selective inhibitor has an IC50 for the Y641 mutant of EZH2 that is at least 90 percent lower than the IC50 for wild-type EZH2.

In one embodiment, the selective inhibitor of a Y641 mutant of EZH2 exerts essentially no inhibitory effect on wild-type EZH2.

The inhibitor inhibits conversion of H3-K27me2 to H3-K27me3. In one embodiment the inhibitor is said to inhibit trimethylation of H3-K27. Since conversion of H3-K27me1 to H3-K27me2 precedes conversion of H3-K27me2 to H3-K27me3, an inhibitor of conversion of H3-K27me1 to H3-K27me2 naturally also inhibits conversion of H3-K27me2 to H3-K27me3, i.e., it inhibits trimethylation of H3-K27. It is also possible to inhibit conversion of H3-K27me2 to H3-K27me3 without inhibition of conversion of H3-K27me1 to H3-K27me2. Inhibition of this type would also result in inhibition of trimethylation of H3-K27, albeit without inhibition of dimethylation of H3-K27.

In one embodiment the inhibitor inhibits conversion of H3-K27me1 to H3-K27me2 and the conversion of H3-K27me2 to H3-K27me3. Such inhibitor may directly inhibit the conversion of H3-K27me1 to H3-K27me2 alone. Alternatively, such inhibitor may directly inhibit both the conversion of H3-K27me1 to H3-K27me2 and the conversion of H3-K27me2 to H3-K27me3.

The inhibitor inhibits histone methylase activity. Inhibition of histone methylase activity can be detected using any suitable method. The inhibition can be measured, for example, either in terms of rate of histone methylase activity or as product of histone methylase activity. Methods suitable for either of these readouts are included in the Examples below.

The inhibition is a measurable inhibition compared to a suitable negative control. In one embodiment, inhibition is at least 10 percent inhibition compared to a suitable negative control. That is, the rate of enzymatic activity or the amount of product with the inhibitor is less than or equal to 90 percent of the corresponding rate or amount made without the inhibitor. In various other embodiments, inhibition is at least 20, 25, 30, 40, 50, 60, 70, 75, 80, 90, or 95 percent inhibition compared to a suitable negative control. In one embodiment, inhibition is at least 99 percent inhibition compared to a suitable negative control. That is, the rate of enzymatic activity or the amount of product with the inhibitor is less than or equal to 1 percent of the corresponding rate or amount made without the inhibitor.

In one embodiment, the inhibitor is S-adenosyl-L-homocysteine (SAH). SAH has the structural formula

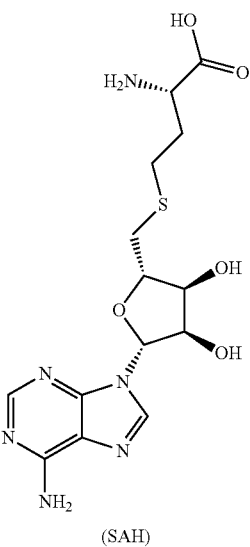 [SMILES: Nc1ncnc2c1ncn2[C@@H]1O[C@H](CSCC[C@H](N)C(=O)O)[C@@H](O)[C@H]1O]

(SAH)

and is commercially available from a number of suppliers, including, for example, Sigma-Aldrich, St. Louis, Mo. SAH has been described as an inhibitor of transmethylation by S-adenosylmethionine-dependent methyltransferases.

In one embodiment, the inhibitor is Compound 75

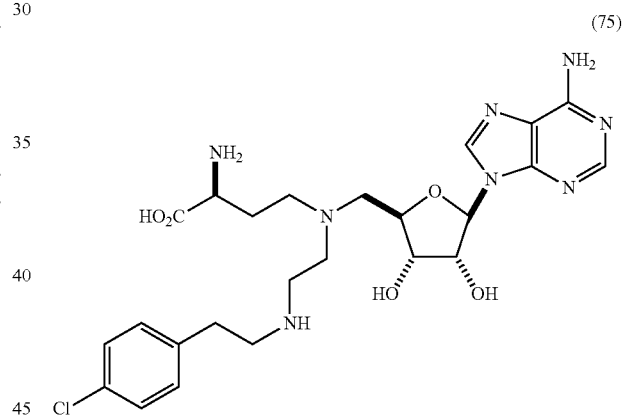

(75)

or a pharmaceutically acceptable salt thereof.

In certain embodiments the invention comprises the step of performing an assay to detect a Y64 mutant of EZH2 in a sample from a subject. Assays of this type are described above. As used herein, a "sample from a subject" refers to any suitable sample containing cells or components of cells obtained or derived from a subject. In one embodiment the sample includes cells suspected to express Y641 mutant of EZH2, e.g., cancer cells. In one embodiment the sample is a blood sample. In one embodiment the sample is a biopsy sample obtained from, for example, a lymphatic tissue (e.g., lymph node) or bone marrow. In one embodiment the sample is a biopsy sample obtained from a tissue other than or in addition to a lymphatic tissue (e.g., lymph node) or bone marrow. For example, in one embodiment the sample is a biopsy from a cancer, e.g., a tumor composed of cancer cells. Cells in the sample can be isolated from other components of the sample. For example, peripheral blood mononuclear cells (PBMCs) can be isolated as a buffy coat from a blood sample that has been centrifuged in accordance with methods familiar to those of skill in the art.

When the result of the assay on a sample from a subject indicates that a Y641 mutant of EZH2 is present in the sample, the subject is said to express the Y641 mutant of EZH2. Indeed, in one embodiment, when the result of the assay on a sample from a subject indicates that a Y641 mutant of EZH2 is present in the sample, the subject is identified as a candidate for treatment with an inhibitor of EZH2, wherein the inhibitor selectively inhibits histone methyltransferase activity of the Y641 mutant of EZH2.

When the result of the assay on a sample from a cancer indicates that a Y641 mutant of EZH2 is present in the cancer, the cancer is said to express the Y641 mutant of EZH2.

Similarly, when the result of the assay on a sample comprising cancer cells from a subject having a cancer indicates that a Y641 mutant of EZH2 is present in the sample, the subject is said to express the Y641 mutant of EZH2.

The present invention also provides a previously unrecognized, surprising correlation of a patient's responsiveness to an EZH2 inhibitor with the H3-K27me2 level or preferably with the levels of H3-K27me and H3-K27me3. For example, cells with a low H3-K27me2 and normal or high me3 levels relative to a control are much more responsive to the antiproliferative effect of an EZH2 inhibitor than cells with a normal H3-K27 me2 and me3 levels.

An aspect of the invention is a method for determining responsiveness to an EZH2 inhibitor in a subject. In one embodiment the method includes isolating a tissue sample from the subject; detecting a dimethylation (me2) level of H3-K27 in the tissue sample; comparing the dimethylation (me2) level to a control dimethylation (me2) level; and identifying the subject is responsive to said EZH2 inhibitor when the dimethylation (me2) level is absent or lower than the control dimethylation (me2) level. In one embodiment, the method further includes detecting a trimethylation (me3) level of H3-K27 in the tissue sample; comparing the trimethylation (me3) level to a control trimethylation (me3) level and the dimethylation (me2) level to a control dimethylation (me2) level; and identifying said subject is responsive to the EZH2 inhibitor when the trimethylation (me3) level is same as or higher than the control trimethylation (me3) level and the dimethylation (me2) level is absent or lower than the control dimethylation (me2) level. In another embodiment, the method further includes obtaining a ratio of the dimethylation (me2) level to the trimethylation (me3) level of H3-K27 in the tissue sample; obtaining a control ratio of the control dimethylation (me2) level to the control trimethylation (me3) level; comparing the ratio to the control ratio; and identifying the subject is responsive to said EZH2 inhibitor when said ratio is lower than said control ratio. In a preferred embodiment, the subject has cancer. In one embodiment, the cancer is a follicular lymphoma. Alternatively, the cancer is a diffuse large B-cell lymphoma (DLBCL). In another preferred embodiment, the subject expresses a Y641 mutant EZH2. In a preferred embodiment, the Y641 mutant is Y641F, Y641H, Y641N or Y641S.

Detection of dimethylated H3-K27 or trimethylated H3-K27 can be accomplished using any suitable method in the art. In one embodiment, the methylation level is detected using antibodies specific for dimethylated H3-K27 or trimethlated H3-K27. For example, the isolated tissue is formalin fixed and embedded in paraffin blocks for long term preservation. The blocks can be used to prepare slides for immunohistochemical staining or fluorescent staining with antibodies against methylated H3-K27. Alternatively, whole cell lysates or histone extracts can be prepared from the isolated tissue sample and subsequently used for immunohistochemical staining, western blot analysis or fluorescent staining. In another embodiment the methylation level is detected using a polypeptide or an aptamer specific for dimethylated H3-K27 or trimethlated H3-K27. In another embodiment, the methylation level is detected using mass spectrometry (MS).

A control dimethylated H3-K27 or a control trimethlated H3-K27 can be established from a control sample, e.g., an adjacent non-tumor tissue isolated from the subject or a healthy tissue from a healthy subject. Alternatively, the control methylation level of H3-K27me2 or H3-K27me3 can be established by a pathologist with known methods in the art.

Screening Methods

An aspect of the invention is a method for identifying a test compound as an inhibitor of a Y641 mutant of EZH2. In one embodiment the method includes combining an isolated Y641 mutant of EZH2 with a histone substrate, a methyl group donor (such as S-adenosyl methionine (SAM)), and a test compound, wherein the histone substrate comprises a form of H3-K27 selected from the group consisting of unmethylated H3-K27, monomethylated H3-K27, dimethylated H3-K27, and any combination thereof; and performing an assay to detect methylation of H3-K27 in the histone substrate, thereby identifying the test compound as an inhibitor of the Y641 mutant of EZH2 when methylation of H3-K27 in the presence of the test compound is less than methylation of H3-K27 in the absence of the test compound. The assay to detect methylation of H3-K27 can be selected to measure the rate of methylation, the extent of methylation, or both the rate and extent of methylation.

The Y641 mutant of EZH2 is isolated as a PRC2 complex or functional equivalent thereof. As used herein, the term "isolated" means substantially separated from other components with which the complex may be found as it occurs in nature. A compound can be isolated without necessarily being purified. In one embodiment the mutant of EZH2 is isolated as a complex of a Y641 mutant of EZH2 together with EED and SUZ12. In another embodiment the mutant of EZH2 is isolated as a complex of a Y641 mutant of EZH2 together with EED, SUZ12, and RbAp48. Under appropriate conditions, a PRC2 complex or functional equivalent thereof exhibits histone methyltransferase activity for H3-K27. In one embodiment the complex is composed of recombinantly expressed component polypeptides, e.g., EZH2, EED, SUZ12, with or without RbAp48.

The isolated Y641 mutant of EZH2 is combined with a histone substrate. A histone substrate includes any suitable source of histone polypeptides or fragments thereof that can serve as substrate for EZH2. In one embodiment the histone substrate includes histones isolated from a subject. The histones can be isolated from cells of a subject using any suitable method; such methods are well known to persons skilled in the art and need not be further specified here. See, for example, Fang et al. (2004) *Methods Enzymol* 377:213-26. In accordance with the Examples below, in one embodiment the histone substrate is provided as nucleosomes. In accordance with the Examples below, in one embodiment the histone substrate is provided as avian (chicken) erythrocyte nucleosomes.

Histone substrate so provided may include an admixture of states of histone modification, including various states of H3-K27 methylation as judged by Western blotting with H3-K27 methylation state-specific antibodies. In one embodiment the histone substrate may be provided as purified full-length histone H3. Such purified full-length histone H3 may be provided as a homogeneous preparation in respect of states of H3-K27 methylation, or as an admixture of various states of H3-K27 methylation. Homogeneous preparations of isolated histone H3 in respect of states of H3-K27 methylation may be prepared in part by passage over an immunoaffinity column loaded with suitable H3-K27 methylation state-specific antibodies or by immunoprecipitation using magnetic beads coated with suitable H3-K27 methylation state-specific antibodies. Alternatively or in addition, the methylation state of H3-K27 can be characterized as part of performing the assay. For example, the starting material histone substrate might be characterized as containing 50 percent unmethylated H3-K27, 40 percent monomethylated H3-K27, 10 percent dimethylated H3-K27, and 0 percent trimethylated H3-K27.

In one embodiment the histone substrate includes a peptide library or a suitable peptide comprising one or more amino acid sequences related to histone H3, including, in particular, a sequence that encompasses H3-K27. For example, in one embodiment, the histone substrate is a peptide fragment that corresponds to amino acid residues 21-44 of histone H3. Such peptide fragment has the amino acid sequence LATKAARK-SAPATGGVKKPHRYRP (SEQ ID NO: 13). The peptide library or peptide can be prepared by peptide synthesis according to techniques well known in the art and optionally modified so as to incorporate any desired degree of methylation of lysine corresponding to H3-K27. As described in the Examples below, such peptides can also be modified to incorporate a label, such as biotin, useful in performing downstream assays. In one embodiment the label is appended to the amino (N)-terminus of the peptide(s). In one embodiment the label is appended to the carboxy (C)-terminus of the peptide(s).

H3-K27 methylation-specific antibodies are available from a variety of commercial sources, including, for example, Cell Signaling Technology (Danvers, Mass.) and Active Motif (Carlsbad, Calif.).

The isolated Y641 mutant of EZH2 is combined with a test compound. As used herein, a "test compound" refers to a small organic molecule having a molecular weight of less than about 1.5 kDa. In one embodiment a test compound is a known compound. In one embodiment a test compound is a novel compound. In one embodiment, a test compound can be provided as part of a library of such compounds, wherein the library includes, for example, tens, hundreds, thousands, or even more compounds. A library of compounds may advantageously be screened in a high throughput screening assay, for example, using arrays of test compounds and robotic manipulation in accordance with general techniques well known in the art.

In certain embodiments a test compound is a compound that is a derivative of SAH or a derivative of Compound 75.

Detection of methylation of H3-K27 can be accomplished using any suitable method. In one embodiment, the source of donor methyl groups includes methyl groups that are labeled with a detectable label. The detectable label in one embodiment is an isotopic label, e.g., tritium. Other types of labels may include, for example, fluorescent labels.

Detection of formation of trimethylated H3-K27 can be accomplished using any suitable method. For example, detection of formation of trimethylated H3-K27 can be accomplished using an assay to detect incorporation of labeled methyl groups, such as described above, optionally combined with a chromatographic or other method to separate labeled products by size, e.g., polyacrylamide gel electrophoresis (PAGE), capillary electrophoresis (CE), or high pressure liquid chromatography (HPLC). Alternatively or in addition, detection of formation of trimethylated H3-K27 can be accomplished using antibodies that are specific for trimethylated H3-K27.

Detection of conversion of monomethylated H3-K27 to dimethylated H3-K27 can be accomplished using any suitable method. In one embodiment the conversion is measured using antibodies specific for monomethylated H3-K27 and dimethylated H3-K27. For example, starting amounts or concentrations of monomethylated H3-K27 and dimethylated H3-K27 may be determined using appropriate antibodies specific for monomethylated H3-K27 and dimethylated H3-K27. Following the combination of enzyme, substrate, methyl group donor, and test compound, resulting amounts or concentrations of monomethylated H3-K27 and dimethylated H3-K27 may then be determined using appropriate antibodies specific for monomethylated H3-K27 and dimethylated H3-K27. The beginning and resulting amounts or concentrations of monomethylated H3-K27 and dimethylated H3-K27 can then be compared. Alternatively or in addition, beginning and resulting amounts or concentrations of monomethylated H3-K27 and dimethylated H3-K27 can then be compared to corresponding amounts of concentrations from a negative control. A negative control reaction, in which no test agent is included in the assay, can be run in parallel or as a historical control. Results of such control reaction can optionally be subtracted from corresponding results of the experimental reaction prior to or in conjunction with making the comparison mentioned above.

Because the dimethylated form of H3-K27 may be further methylated in the same assay, a reduction in the amount or concentration of monomethylated H3-K27 may not appear to correspond directly to an increase in dimethylated H3-K27. In this instance, it may be presumed, however, that a reduction in the amount or concentration of monomethylated H3-K27 is, by itself, reflective of conversion of monomethylated H3-K27 to dimethylated H3-K27.

Detection of conversion of dimethylated H3-K27 to trimethylated H3-K27 can be accomplished using any suitable method. In one embodiment the conversion is measured using antibodies specific for dimethylated H3-K27 and trimethylated H3-K27. For example, starting amounts or concentrations of dimethylated H3-K27 and trimethylated H3-K27 may be determined using appropriate antibodies specific for dimethylated H3-K27 and trimethylated H3-K27. Following the combination of enzyme, substrate, and test compound, resulting amounts or concentrations of dimethylated H3-K27 and trimethylated H3-K27 may then be determined using appropriate antibodies specific for dimethylated H3-K27 and trimethylated H3-K27. The beginning and resulting amounts or concentrations of dimethylated H3-K27 and trimethylated H3-K27 can then be compared. Alternatively or in addition, beginning and resulting amounts or concentrations of dimethylated H3-K27 and trimethylated H3-K27 can then be compared to corresponding amounts of concentrations from a negative control. A negative control reaction, in which no test agent is included in the assay, can be run in parallel or as a historical control. Results of such control reaction can optionally be subtracted from corresponding results of the experimental reaction prior to or in conjunction with making the comparison mentioned above.

A test agent is identified as an inhibitor of the Y641 mutant of EZH2 when methylation of H3-K27 with the test compound is less than methylation of H3-K27 without the test compound. In one embodiment, a test agent is identified as an inhibitor of the Y641 mutant of EZH2 when formation of trimethylated H3-K27 in the presence of the test compound is less than formation of trimethylated H3-K27 in the absence of the test compound.

An aspect of the invention is a method for identifying a selective inhibitor of a Y641 mutant of EZH2. In one embodiment the method includes combining an isolated Y641 mutant of EZH2 with a histone substrate, a methyl group donor (e.g., SAM), and a test compound, wherein the histone substrate comprises a form of H3-K27 selected from the group consisting of monomethylated H3-K27, dimethylated H3-K27, and a combination of monomethylated H3-K27 and dimethylated H3-K27, thereby forming a test mixture; combining an isolated wild-type EZH2 with a histone substrate, a methyl group donor (e.g., SAM), and a test compound, wherein the histone substrate comprises a form of H3-K27 selected from the group consisting of monomethylated H3-K27, dimethylated H3-K27, and a combination of monomethylated H3-K27 and dimethylated H3-K27, thereby forming a control mixture; performing an assay to detect trimethylation of the histone substrate in each of the test mixture and the control mixture; calculating the ratio of (a) trimethylation with the Y641 mutant of EZH2 and the test compound (M+) to (b) trimethylation with the Y641 mutant of EZH2 without the test compound (M−); calculating the ratio of (c) trimethylation with wild-type EZH2 and the test compound (WT+) to (d) trimethylation with wild-type EZH2 without the test compound (WT−); comparing the ratio (a)/(b) with the ratio (c)/(d); and identifying the test compound as a selective inhibitor of the Y641 mutant of EZH2 when the ratio (a)/(b) is less than the ratio (c)/(d). In one embodiment the method further includes taking into account a negative control without test compound for either or both of the test mixture and the control mixture.

Pharmaceutical Compositions

One or more EZH2 antagonists can be administered alone to a human patient or in pharmaceutical compositions where they are mixed with suitable carriers or excipient(s) at doses to treat or ameliorate a disease or condition as described herein. Mixtures of these EZH2 antagonists can also be administered to the patient as a simple mixture or in suitable formulated pharmaceutical compositions. For example, one aspect of the invention relates to pharmaceutical composition comprising a therapeutically effective dose of an EZH2 antagonist, or a pharmaceutically acceptable salt, hydrate, enantiomer or stereoisomer thereof; and a pharmaceutically acceptable diluent or carrier.

Techniques for formulation and administration of EZH2 antagonists may be found in references well known to one of ordinary skill in the art, such as Remington's "The Science and Practice of Pharmacy," 21st ed., Lippincott Williams & Wilkins 2005.

Suitable routes of administration may, for example, include oral, rectal, or intestinal administration; parenteral delivery, including intravenous, intramuscular, intraperitoneal, subcutaneous, or intramedullary injections, as well as intrathecal, direct intraventricular, or intraocular injections; topical delivery, including eyedrop and transdermal; and intranasal and other transmucosal delivery.

Alternatively, one may administer an EZH2 antagonist in a local rather than a systemic manner, for example, via injection of the EZH2 antagonist directly into an edematous site, often in a depot or sustained release formulation.

In one embodiment, an EZH2 antagonist is administered by direct injection into a tumor or lymph node.

Furthermore, one may administer an EZH2 antagonist in a targeted drug delivery system, for example, in a liposome coated with cancer cell-specific antibody.

The pharmaceutical compositions of the present invention may be manufactured, e.g., by conventional mixing, dissolving, granulating, dragee-making, levigating, emulsifying, encapsulating, entrapping or lyophilizing processes.

Pharmaceutical compositions for use in accordance with the present invention thus may be formulated in a conventional manner using one or more physiologically acceptable carriers comprising excipients and auxiliaries which facilitate processing of the active EZH2 antagonists into preparations which can be used pharmaceutically. Proper formulation is dependent upon the route of administration chosen.

For injection, the agents of the invention may be formulated in aqueous solutions, preferably in physiologically compatible buffers such as Hanks' solution, Ringer's solution, or physiological saline buffer. For transmucosal administration, penetrants are used in the formulation appropriate to the barrier to be permeated. Such penetrants are generally known in the art.

For oral administration, the EZH2 antagonists can be formulated readily by combining the active EZH2 antagonists with pharmaceutically acceptable carriers well known in the art. Such carriers enable the EZH2 antagonists of the invention to be formulated as tablets, pills, dragees, capsules, liquids, gels, syrups, slurries, suspensions and the like, for oral ingestion by a patient to be treated. Pharmaceutical preparations for oral use can be obtained by combining the active EZH2 antagonist with a solid excipient, optionally grinding a resulting mixture, and processing the mixture of granules, after adding suitable auxiliaries, if desired, to obtain tablets or dragee cores. Suitable excipients include fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active EZH2 antagonist doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active EZH2 antagonists may be dissolved or suspended in suitable liquids, such as fatty oils, liquid paraffin, or liquid polyethylene glycols. In addition, stabilizers may be added.

For buccal administration, the compositions may take the form of tablets or lozenges formulated in conventional manner.

For administration by inhalation, the EZH2 antagonists for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of pressurized aerosol the dosage unit may be determined by providing a valve to deliver a metered amount. Capsules and cartridges of e.g., gelatin for use in an inhaler or insufflator may be formulated containing a powder mix of the EZH2 antagonist and a suitable powder base such as lactose or starch.

The EZH2 antagonists can be formulated for parenteral administration by injection, e.g., bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active EZH2 antagonists in water-soluble form. Additionally, suspensions of the active EZH2 antagonists may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the EZH2 antagonists to allow for the preparation of highly concentrated solutions.

Alternatively, the active ingredient may be in powder form for reconstitution before use with a suitable vehicle, e.g., sterile pyrogen-free water.

The EZH2 antagonists may also be formulated in rectal compositions such as suppositories or retention enemas, e.g., containing conventional suppository bases, such as cocoa butter or other glycerides.

In addition to the formulations described previously, the EZH2 antagonists may also be formulated as a depot preparation. Such long acting formulations may be administered by implantation (for example, subcutaneously or intramuscularly or by intramuscular injection). Thus, for example, the EZH2 antagonists may be formulated with suitable polymeric or hydrophobic materials (for example as an emulsion in an acceptable oil) or ion exchange resins, or as sparingly soluble derivatives (for example, as a sparingly soluble salt).

Alternatively, other delivery systems for hydrophobic pharmaceutical EZH2 antagonists may be employed. Liposomes and emulsions are examples of delivery vehicles or carriers for hydrophobic drugs. Certain organic solvents such as dimethylsulfoxide also may be employed. Additionally, the EZH2 antagonists may be delivered using a sustained-release system, such as semi-permeable matrices of solid hydrophobic polymers containing the therapeutic agent. Various sustained-release materials have been established and are well known by those skilled in the art. Sustained-release capsules may, depending on their chemical nature, release the EZH2 antagonists for a few weeks up to over 100 days. Depending on the chemical nature and the biological stability of the therapeutic reagent, additional strategies for protein stabilization may be employed.

The pharmaceutical compositions may also comprise suitable solid or gel phase carriers or excipients. Examples of such carriers or excipients include but are not limited to calcium carbonate, calcium phosphate, various sugars, starches, cellulose derivatives, gelatin, and polymers, such as polyethylene glycols.

Methods of Treatment

Provided herein are methods of treating or preventing conditions and diseases the course of which can be influenced by modulating the methylation status of histones or other proteins, wherein said methylation status is mediated at least in part by the activity of EZH2. Modulation of the methylation status of histones can in turn influence the level of expression of target genes activated by methylation, and/or target genes suppressed by methylation.

For example, one aspect of the invention relates to a method for treating cancer. The method comprises the step of administering to a subject having a cancer expressing a Y641 mutant of EZH2 a therapeutically effective amount of an inhibitor of EZH2, wherein the inhibitor inhibits histone methyltransferase activity of EZH2, thereby treating the cancer. In one embodiment the inhibitor inhibits histone methyltransferase activity of the Y641 mutant of EZH2. In one embodiment the inhibitor selectively inhibits histone methyltransferase activity of the Y641 mutant of EZH2. In one embodiment the cancer is a follicular lymphoma. In one embodiment the cancer is a diffuse large B-cell lymphoma (DLBCL).

An aspect of the invention relates to a method for treating cancer. The method comprises the steps of performing an assay to detect a Y641 mutant of EZH2 in a sample comprising cancer cells from a subject having a cancer, and administering to a subject expressing a Y641 mutant of EZH2 a therapeutically effective amount of an inhibitor of EZH2, wherein the inhibitor inhibits histone methyltransferase activity of EZH2, thereby treating the cancer. In one embodiment the inhibitor inhibits histone methyltransferase activity of the Y641 mutant of EZH2. In one embodiment the inhibitor selectively inhibits histone methyltransferase activity of the Y641 mutant of EZH2. In one embodiment the cancer is a follicular lymphoma. In one embodiment the cancer is a diffuse large B-cell lymphoma (DLBCL).

Diseases such as cancers and neurological disease can be treated by administration of modulators of protein (e.g., histone) methylation, e.g., modulators of histone methyltransferase, or histone demethylase enzyme activity. Histone methylation has been reported to be involved in aberrant expression of certain genes in cancers, and in silencing of neuronal genes in non-neuronal cells. Modulators described herein can be used to treat such diseases, i.e., to inhibit methylation of histones in affected cells.

Based at least on the fact that increased histone methylation has been found to be associated with certain cancers, a method for treating cancer in a subject comprises administering to the subject in need thereof a therapeutically effective amount of a compound that inhibits methylation or restores methylation to roughly its level in counterpart normal cells. In one embodiment a method for treating cancer in a subject comprises administering to the subject in need thereof a therapeutically effective amount of a compound that inhibits conversion of unmethylated H3-K27 to monomethylated H3-K27 (H3-K27me1). In one embodiment a method for treating cancer in a subject comprises administering to the subject in need thereof a therapeutically effective amount of a compound that inhibits conversion of monomethylated H3-K27 (H3-K27me1) to dimethylated H3-K27 (H3-K27me2). In one embodiment a method for treating cancer in a subject comprises administering to the subject in need thereof a therapeutically effective amount of a compound that inhibits conversion of H3-K27me2 to trimethylated H3-K27 (H3-K27me3). In one embodiment a method for treating cancer in a subject comprises administering to the subject in need thereof a therapeutically effective amount of a compound that inhibits both conversion of H3-K27me1 to H3-K27me2 and conversion of H3-K27me2 to H3-K27me3. It is important to note that disease-specific increase in methylation can occur at chromatin in key genomic loci in the absence of a global increase in cellular levels of histone or protein methylation. For example, it is possible for aberrant hypermethylation at key disease-relevant genes to occur against a backdrop of global histone or protein hypomethylation.

Modulators of methylation can be used for modulating cell proliferation, generally. For example, in some cases excessive proliferation may be reduced with agents that decrease methylation, whereas insufficient proliferation may be stimulated with agents that increase methylation. Accordingly, diseases that may be treated include hyperproliferative diseases, such as benign cell growth and malignant cell growth (cancer).

Exemplary cancers that may be treated include lymphomas, including follicular lymphoma (FL) and diffuse large B-cell lymphoma (DLBCL).

Other cancers include Acute Lymphoblastic Leukemia; Acute Myeloid Leukemia; Adrenocortical Carcinoma; AIDS-Related Cancers; AIDS-Related Lymphoma; Anal Cancer; Astrocytoma, Childhood Cerebellar; Astrocytoma, Childhood Cerebral; Basal Cell Carcinoma, see Skin Cancer (non-Melanoma); Bile Duct Cancer, Extrahepatic; Bladder Cancer; Bone Cancer, osteosarcoma/Malignant Fibrous Histiocytoma; Brain Stem Glioma; Brain Tumor; Brain Tumor, Cerebellar Astrocytoma; Brain Tumor, Cerebral Astrocytoma/Malignant Glioma; Brain Tumor, Ependymoma; Brain Tumor, Medulloblastoma; Brain Tumor, Supratentorial Primitive Neuroectodermal Tumors; Brain Tumor, Visual Pathway and Hypothalamic Glioma; Breast Cancer; Bronchial Adenomas/Carcinoids; Burkitt's Lymphoma; Carcinoid Tumor; Carcinoid Tumor, Gastrointestinal; Carcinoma of Unknown Primary; Central Nervous System Lymphoma, Primary; Cerebellar Astrocytoma; Cervical Cancer; Childhood Cancers; Chronic Lymphocytic Leukemia; Chronic Myelogenous Leukemia; Chronic Myelogenous Leukemia, Hairy Cell; Chronic Myeloproliferative Disorders; Colon Cancer, Colorectal Cancer; Cutaneous T-Cell Lymphoma, see Mycosis Fungoides and Sezary Syndrome; Endometrial Cancer; Esophageal Cancer; Ewing's Family of Tumors; Extrahepatic Bile Duct Cancer; Eye Cancer, Intraocular Melanoma; Eye Cancer, Retinoblastoma; Gallbladder Cancer, Gastric (Stomach) Cancer; Gastrointestinal Carcinoid Tumor; Germ Cell Tumor, Extracranial; Germ Cell Tumor, Extragonadal; Germ Cell Tumor, Ovarian; Gestational Trophoblastic Tumor; Glioma; Glioma, Childhood Brain Stem; Glioma, Childhood Cerebral Astrocytoma; Glioma, Childhood Visual Pathway and Hypothalamic; Hairy Cell Leukemia; Head and Neck Cancer; Hepatocellular (Liver) Cancer, Adult (Primary); Hepatocellular (Liver) Cancer, Childhood (Primary); Hodgkin's Lymphoma; Hodgkin's Lymphoma During Pregnancy; Hypopharyngeal Cancer; Hypothalamic and Visual Pathway Glioma; Intraocular Melanoma; Islet Cell Carcinoma (Endocrine Pancreas); Kaposi's Sarcoma; Kidney (Renal Cell) Cancer; Kidney Cancer; Laryngeal Cancer; Leukemia; Lip and Oral Cavity Cancer, Liver Cancer, Adult (Primary); Liver Cancer, Childhood (Primary); Lung Cancer, Non-Small Cell; Lung Cancer, Small Cell; Lymphoma, Primary Central Nervous System; Macroglobulinemia, Waldenstrom's; Malignant Fibrous Histiocytoma of Bone/Osteosarcoma; Medulloblastoma; Melanoma; Merkel Cell Carcinoma; Mesothelioma; Mesothelioma, Adult Malignant; Metastatic Squamous Neck Cancer with Occult Primary; Multiple Endocrine Neoplasia Syndrome; Multiple Myeloma; Multiple Myeloma/Plasma Cell Neoplasm Mycosis Fungoides; Myelodysplastic Syndromes; Myelodysplastic/Myeloproliferative Diseases; Myeloid Leukemia, Adult Acute; Myeloid Leukemia, Childhood Acute; Myeloproliferative Disorders, Chronic; Nasal Cavity and Paranasal Sinus Cancer. Nasopharyngeal Cancer; Neuroblastoma; Non-Hodgkin's Lymphoma; Non-Hodgkin's Lymphoma During Pregnancy; Oral Cancer; Oral Cavity Cancer, Lip and; Oropharyngeal Cancer; Osteosarcoma/Malignant Fibrous Histiocytoma of Bone; Ovarian Cancer; Ovarian Epithelial Cancer; Ovarian Low Malignant Potential Tumor; Pancreatic Cancer; Pancreatic Cancer, Islet Cell; Paranasal Sinus and Nasal Cavity Cancer; Parathyroid Cancer; Penile Cancer; Pheochromocytoma; Pineoblastoma and Supratentorial Primitive Neuroectodermal Tumors; Pituitary Tumor; Plasma Cell Neoplasm/Multiple Myeloma; Pleuropulmonary Blastoma; Pregnancy and Breast Cancer; Prostate Cancer; Rectal Cancer Retinoblastoma; Rhabdomyosarcoma; Salivary Gland Cancer; Sarcoma, Ewing's Family of Tumors; Sarcoma, Soft Tissue; Sarcoma, Uterine; Sezary Syndrome; Skin Cancer; Skin Cancer (non-Melanoma); Small Intestine Cancer; Soft Tissue Sarcoma; Squamous Cell Carcinoma, see Skin Cancer (non-Melanoma); Squamous Neck Cancer with Occult Primary, Metastatic; Stomach (Gastric) Cancer, Testicular Cancer, Thymoma; Thymoma and Thymic Carcinoma; Thyroid Cancer, Transitional Cell Cancer of the Renal Pelvis and Ureter; Trophoblastic Tumor, Gestational; Unknown Primary Site, Cancer of; Unusual Cancers of Childhood; Urethral Cancer; Uterine Cancer, Endometrial; Uterine Sarcoma; Vaginal Cancer; Visual Pathway and Hypothalamic Glioma; Vulvar Cancer; Waldenstrom's Macroglobulinemia; Wilms' Tumor; and Women's Cancers.

Any other disease in which epigenetic methylation, which is mediated by EZH2, plays a role may be treatable or preventable using compounds and methods described herein.

For example, neurologic diseases that may be treated include epilepsy, schizophrenia, bipolar disorder or other psychological and/or psychiatric disorders, neuropathies, skeletal muscle atrophy, and neurodegenerative diseases, e.g., a neurodegenerative disease. Exemplary neurodegenerative diseases include: Alzheimer's, Amyotrophic Lateral Sclerosis (ALS), and Parkinson's disease. Another class of neurodegenerative diseases includes diseases caused at least in part by aggregation of poly-glutamine. Diseases of this class include: Huntington's Diseases. Spinalbulbar Muscular Atrophy (SBMA or Kennedy's Disease), Dentatorubropallidoluysian Atrophy (DRPLA), Spinocerebellar Ataxia 1 (SCA1), Spinocerebellar Ataxia 2 (SCA2), Machado-Joseph Disease (MJD; SCA3), Spinocerebellar Ataxia 6 (SCA6), Spinocerebellar Ataxia 7 (SCA7), and Spinocerebellar Ataxia 12 (SCA12).

Also provided herein are methods for selecting a treatment for a subject having a cancer. The method includes determining responsiveness of the subject to an EZH2 inhibitor by the dimethylated H3-K27 level, preferably by the levels of dimethylated H3-K27 and trimethlated H3-K27; and providing the EZH2 inhibitor to the subject when the subject is responsive to the EZH2 inhibitor. In one embodiment, the cancer is a follicular lymphoma. Alternatively, the cancer is a diffuse large B-cell lymphoma (DLBCL). In another preferred embodiment, the subject expresses a Y641 mutant EZH2. In a preferred embodiment, the Y641 mutant is Y641F, Y641H, Y641N or Y641S.

Combination Therapy

In one aspect of the invention, an EZH2 antagonist, or a pharmaceutically acceptable salt thereof, can be used in combination with another therapeutic agent to treat diseases such as cancer and/or neurological disorders. For example, the additional agent can be a therapeutic agent that is art-recognized as being useful to treat the disease or condition being treated by the compound of the present invention. The additional agent also can be an agent that imparts a beneficial attribute to the therapeutic composition (e.g., an agent that affects the viscosity of the composition).

The combination therapy contemplated by the invention includes, for example, administration of a compound of the invention, or a pharmaceutically acceptable salt thereof, and additional agent(s) in a single pharmaceutical formulation as well as administration of a compound of the invention, or a pharmaceutically acceptable salt thereof, and additional agent(s) in separate pharmaceutical formulations. In other words, co-administration shall mean the administration of at least two agents to a subject so as to provide the beneficial effects of the combination of both agents. For example, the agents may be administered simultaneously or sequentially over a period of time.

The agents set forth below are for illustrative purposes and not intended to be limiting. The combinations, which are part of this invention, can be the compounds of the present invention and at least one additional agent selected from the lists below. The combination can also include more than one additional agent, e.g., two or three additional agents if the combination is such that the formed composition can perform its intended function.

For example, one aspect of the invention relates to the use of an EZH2 antagonist in combination with another agent for the treatment of cancer and/or a neurological disorder. In one embodiment, an additional agent is an anticancer agent that is a compound that affects histone modifications, such as an HDAC inhibitor. In certain embodiments, an additional anticancer agent is selected from the group consisting of chemotherapeutics (such as 2CdA, 5-FU, 6-Mercaptopurine, 6-TG, Abraxane™, Accutane®, Actinomycin-D, Adriamycin®, Alimta®, all-trans retinoic acid, amethopterin, Ara-C, Azacitadine, BCNU, Blenoxane®, Camptosar®, CeeNU®, Clofarabine, Clolar™, Cytoxan®, daunorubicin hydrochloride, DaunoXome®, Dacogen®, DIC, Doxil®, Ellence®, Eloxatin®, Emcyt®, etoposide phosphate, Fludara®, FUDR®, Gemzar®, Gleevec®, hexamethylmelamine, Hycamtin®, Hydrea®, Idamycin®, Ifex®, ixabepilone, Ixempra®, L-asparaginase, Leukeran®, liposomal Ara-C, L-PAM, Lysodren, Matulane®, mithracin, Mitomycin-C, Myleran®, Navelbine®, Neutrexin®, nilotinib, Nipent®, Nitrogen Mustard, Novantrone®, Oncaspar®, Panretin®, Paraplatin®, Platinol®, prolifeprospan 20 with carmustine implant, Sandostatin®, Targretin®, Tasigna®, Taxotere®, Temodar®, TESPA, Trisenox®, Valstar®, Velban®, Vidaza™, vincristine sulfate, VM 26, Xeloda® and Zanosar®); biologics (such as Alpha Interferon, Bacillus Calmette-Guerin, Bexxar®, Campath®, Ergamisol®, Erlotinib, Herceptin®, Interleukin-2, Iressa®, lenalidomide, Mylotarg®, Ontak®, Pegasys®, Revlimid®, Rituxan®, Tarceva™, Thalomid®, Tykerb®, Velcade® and Zevalin™); corticosteroids, (such as dexamethasone sodium phosphate, DeltaSone® and Delta-Cortef)); hormonal therapies (such as Arimidex®, Aromasin®, Casodex®, Cytadren®, Eligard®, Eulexin®, Evista®, Faslodex®, Femara®, Halotestin®, Megace®, Nilandron®, Nolvadex®, Plenaxis™ and Zoladex®); and radiopharmaceuticals (such as Iodotope®, Metastron®, Phosphocol® and Samarium SM-153).

Dosage

As used herein, a "therapeutically effective amount" or "therapeutically effective dose" is an amount of an EZH2 antagonist or a combination of two or more such compounds, which inhibits, totally or partially, the progression of the condition or alleviates, at least partially, one or more symptoms of the condition. A therapeutically effective amount can also be an amount which is prophylactically effective. The amount which is therapeutically effective will depend upon the patient's size and gender, the condition to be treated, the severity of the condition and the result sought. In one embodiment, a therapeutically effective dose refers to that amount of the EZH2 antagonists that results in amelioration of symptoms in a patient. For a given patient, a therapeutically effective amount may be determined by methods known to those of skill in the art.

Toxicity and therapeutic efficacy of EZH2 antagonists can be determined by standard pharmaceutical procedures in cell cultures or experimental animals, e.g., for determining the maximum tolerated dose (MTD) and the $ED_{50}$ (effective dose for 50% maximal response). The dose ratio between toxic and therapeutic effects is the therapeutic index and it can be expressed as the ratio between MTD and $ED_{50}$. The data obtained from these cell culture assays and animal studies can be used in formulating a range of dosage for use in humans. Dosage may also be guided by monitoring the EZH2 antagonist's effect on pharmacodynamic markers of enzyme inhibition (e.g., histone methylation or target gene expression) in diseased or surrogate tissue. Cell culture or animal experiments can be used to determine the relationship between doses required for changes in pharmacodynamic markers and doses required for therapeutic efficacy can be determined in cell culture or animal experiments or early stage clinical trials. The dosage of such EZH2 antagonists lies preferably within a range of circulating concentrations that include the $ED_{50}$ with little or no toxicity. The dosage may vary within this range depending upon the dosage form employed and the route of administration utilized. The exact formulation, route of administration and dosage can be chosen by the individual physician in view of the patient's condition. In the treatment of crises, the administration of an acute bolus or an infusion approaching the MTD may be required to obtain a rapid response.

Dosage amount and interval may be adjusted individually to provide plasma levels of the active moiety which are sufficient to maintain the methyltransferase modulating effects, or minimal effective concentration (MEC) for the required period of time to achieve therapeutic efficacy. The MEC will vary for each EZH2 antagonist but can be estimated from in vitro data and animal experiments. Dosages necessary to achieve the MEC will depend on individual characteristics and route of administration. However, high pressure liquid chromatography (HPLC) assays or bioassays can be used to determine plasma concentrations.

Dosage intervals can also be determined using the MEC value. In certain embodiments, EZH2 antagonists should be administered using a regimen which maintains plasma levels above the MEC for 10-90% of the time, preferably between 30-90% and most preferably between 50-90% until the desired amelioration of symptoms is achieved. In other embodiments, different MEC plasma levels will be maintained for differing amounts of time. In cases of local administration or selective uptake, the effective local concentration of the drug may not be related to plasma concentration.

One of skill in the art can select from a variety of administration regimens and the amount of EZH2 antagonist administered will, of course, be dependent on the subject being treated, on the subject's weight, the severity of the affliction, the manner of administration and the judgment of the prescribing physician.

Compounds and Pharmaceutical Compositions

Aspects of the invention concern compounds which are useful according to the methods of the invention. These compounds are referred to herein as "inhibitors of EZH2" and, equivalently, "EZH2 antagonists". The compounds can be presented as the compounds per se, pharmaceutically acceptable salts of the compounds, or as pharmaceutical compositions.

Such compounds specifically include Compound 75

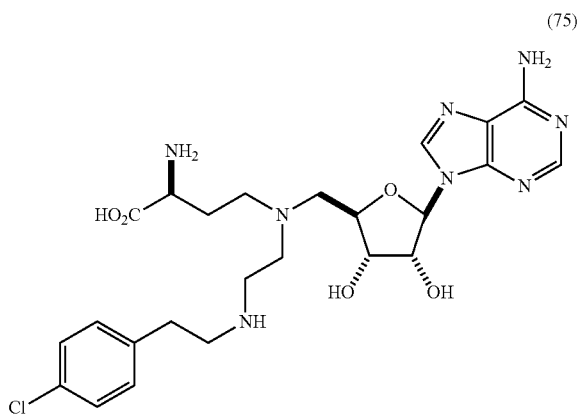

(75)

and pharmaceutically acceptable salts thereof.

The invention further includes a pharmaceutical composition comprising Compound 75

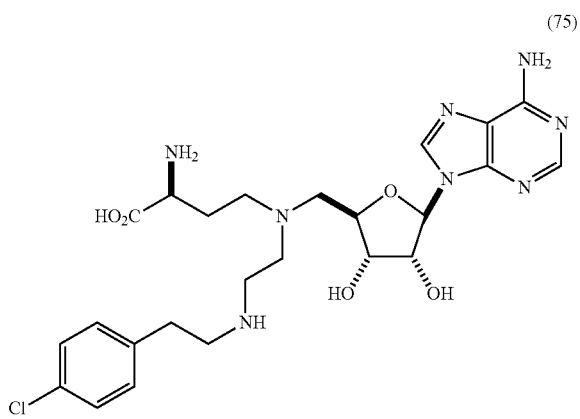

(75)

or a pharmaceutically acceptable salt thereof.

An EZH2 antagonist and optionally other therapeutics can be administered per se (neat) or in the form of a pharmaceutically acceptable salt. When used in medicine the salts should be pharmaceutically acceptable, but non-pharmaceutically acceptable salts can conveniently be used to prepare pharmaceutically acceptable salts thereof.

Compounds useful in accordance with the invention may be provided as salts with pharmaceutically compatible counterions (i.e., pharmaceutically acceptable salts). A "pharmaceutically acceptable salt" means any non-toxic salt that, upon administration to a recipient, is capable of providing, either directly or indirectly, a compound or a prodrug of a compound useful in accordance with this invention. A "pharmaceutically acceptable counterion" is an ionic portion of a salt that is not toxic when released from the salt upon administration to a subject. Pharmaceutically compatible salts may be formed with many acids, including but not limited to hydrochloric, sulfuric, acetic, lactic, tartaric, malic, and succinic acids. Salts tend to be more soluble in water or other protic solvents than their corresponding free base forms. The present invention includes the use of such salts.

Pharmaceutically acceptable acid addition salts include those formed with mineral acids such as hydrochloric acid and hydrobromic acid, and also those formed with organic acids such as maleic acid. For example, acids commonly employed to form pharmaceutically acceptable salts include inorganic acids such as hydrogen bisulfide, hydrochloric, hydrobromic, hydroiodic, sulfuric and phosphoric acid, as well as organic acids such as para-toluenesulfonic, salicylic, tartaric, bitartaric, ascorbic, maleic, besylic, fumaric, gluconic, glucuronic, formic, glutamic, methanesulfonic, ethanesulfonic, benzenesulfonic, lactic, oxalic, para-bromophenylsulfonic, carbonic, succinic, citric, benzoic and acetic acid, and related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephthalate, sulfonate, xylenesulfonate, phenylacetate, phenylpropionate, phenylbutyrate, citrate, lactate, β-hydroxybutyrate, glycolate, maleate, tartrate, methanesulfonate, propanesulfonate, naphthalene-1-sulfonate, naphthalene-2-sulfonate, mandelate and the like.

Suitable bases for forming pharmaceutically acceptable salts with acidic functional groups include, but are not limited to, hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or trialkylamines; dicyclohexylamine; tributyl amine; pyridine; N-methyl, N-ethylamine; diethylamine; triethylamine; mono-, bis-, or tris-(2-hydroxy-lower alkyl amines), such as mono-, bis-, or tris-(2-hydroxyethyl)amine, 2-hydroxy-tert-butylamine, or tris-(hydroxymethyl)methylamine, N,N-di alkyl-N-(hydroxy alkyl)-amines, such as N,N-dimethyl-N-(2-hydroxyethyl)amine, or tri-(2-hydroxyethyl)amine; N-methyl-D-glucamine; and amino acids such as arginine, lysine, and the like.

Certain compounds useful in accordance with the invention and their salts may exist in more than one crystalline form (i.e., polymorph); the present invention includes the use of each of the crystal forms and mixtures thereof.

Certain compounds useful in accordance with the invention may contain one or more chiral centers, and exist in different optically active forms. When compounds useful in accordance with the invention contain one chiral center, the compounds exist in two enantiomeric forms and the present invention includes the use of both enantiomers and mixtures of enantiomers, such as racemic mixtures thereof. The enantiomers may be resolved by methods known to those skilled in the art; for example, enantiomers may be resolved by formation of diastereoisomeric salts which may be separated, for example, by crystallization; formation of diastereoisomeric derivatives or complexes which may be separated, for example, by crystallization, gas-liquid or liquid chromatography; selective reaction of one enantiomer with an enantiomer-specific reagent, for example, via enzymatic esterification; or gas-liquid or liquid chromatography in a chiral environment, for example, on a chiral support (e.g., silica with a bound chiral ligand) or in the presence of a chiral solvent. Where the desired enantiomer is converted into another chemical entity by one of the separation procedures described above, a further step may be used to liberate the desired purified enantiomer. Alternatively, specific enantiomers may be synthesized by asymmetric synthesis using optically active reagents, substrates, catalysts or solvents, or by converting one enantiomer into the other by asymmetric transformation.

When a compound useful in accordance with the invention contains more than one chiral center, it may exist in diastereoisomeric forms. The diastereoisomeric compounds may be separated by methods known to those skilled in the art (for example, chromatography or crystallization) and the individual enantiomers may be separated as described above. The present invention includes the use of various diastereoisomers of compounds useful in accordance with the invention, and mixtures thereof. Compounds useful in accordance with the invention may exist in different tautomeric forms or as different geometric isomers, and the present invention includes the use of each tautomer and/or geometric isomer of compounds useful in accordance with the invention, and mixtures thereof. Compounds useful in accordance with the invention may exist in zwitterionic form. The present invention includes the use of each zwitterionic form of compounds useful in accordance with the invention, and mixtures thereof.

Kits

An EZH2 antagonist may, if desired, be presented in a kit (e.g., a pack or dispenser device) which may contain one or more unit dosage forms containing the EZH2 antagonist. The pack may for example comprise metal or plastic foil, such as a blister pack. The pack or dispenser device may be accompanied by instructions for administration. Compositions comprising an EZH2 antagonist of the invention formulated in a compatible pharmaceutical carrier may also be prepared, placed in an appropriate container, and labeled for treatment of an indicated condition. Instructions for use may also be provided.

Also provided herein are kits comprising a plurality of methylation detection reagents that detect the methylated H3-K27. For example, the kit includes mono-methylated H3-K27, di-methylated H3-K27 and tri-methylated H3-K27 detection reagents. The detection reagent is for example antibodies or fragments thereof, polypeptide or aptamers. The kit may contain in separate containers an aptamer or an antibody, control formulations (positive and/or negative), and/or a detectable label such as fluorescein, green fluorescent protein, rhodamine, cyanine dyes, Alexa dyes, luciferase, radiolabels, among others. Instructions (e.g., written, tape, VCR, CD-ROM, etc.) for carrying out the assay may be included in the kit. The assay may for example be in the form of a Western Blot analysis, Immunohistochemistry (IHC), immunofluorescence (IF) and Mass spectrometry (MS) as known in the art.

DEFINITIONS

For convenience, certain terms employed in the specification, examples, and appended claims are collected here. All definitions, as defined and used herein, supersede dictionary definitions, definitions in documents incorporated by reference, and/or ordinary meanings of the defined terms.

The articles "a" and "an" are used herein to refer to one or to more than one (i.e., to at least one) of the grammatical object of the article. By way of example, "an element" means one element or more than one element.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The terms "co-administration" and "co-administering" refer to both concurrent administration (administration of two or more therapeutic agents at the same time) and time varied administration (administration of one or more therapeutic agents at a time different from that of the administration of an additional therapeutic agent or agents), as long as the therapeutic agents are present in the patient to some extent at the same time.

The term "treating" as used herein refers to alleviate of at least one symptom of the disease, disorder or condition. The term encompasses the administration and/or application of one or more compounds described herein, to a subject, for the purpose of providing management of, or remedy for a condition. "Treatment" for the purposes of this disclosure, may, but does not have to, provide a cure; rather, "treatment" may be in the form of management of the condition. When the compounds described herein are used to treat unwanted proliferating cells, including cancers, "treatment" includes partial or total destruction of the undesirable proliferating cells with minimal destructive effects on normal cells. A desired mechanism of treatment of unwanted rapidly proliferating cells, including cancer cells, at the cellular level is apoptosis.

The term "preventing" as used herein includes either preventing or slowing the onset of a clinically evident disease progression altogether or preventing or slowing the onset of a preclinically evident stage of a disease in individuals at risk. This includes prophylactic treatment of those at risk of developing a disease.

The term "subject" as used herein for purposes of treatment includes any human subject who has been diagnosed with, has symptoms of, or is at risk of developing a disorder. For methods of prevention the subject is any human subject. To illustrate, for purposes of prevention, a subject may be a human subject who is at risk of or is genetically predisposed to obtaining a disorder characterized by unwanted, rapid cell proliferation, such as cancer. The subject may be at risk due to exposure to carcinogenic agents, being genetically predisposed to disorders characterized by unwanted, rapid cell proliferation, and so on.

Except as otherwise indicated, standard methods can be used for the production of recombinant and synthetic polypeptides, fusion proteins, antibodies or antigen-binding fragments thereof, manipulation of nucleic acid sequences, production of transformed cells, and the like. Such techniques are known to those skilled in the art. See, e.g., Sambrook et al., *Molecular Cloning: A Laboratory Manual*, 3rd Ed. (Cold Spring Harbor, N.Y., 2001); F. M. Ausubel et al. *Current Protocols in Molecular Biology* (Green Publishing Associates, Inc. and John Wiley & Sons, Inc., New York).

The term "EZH2 polypeptide" encompasses functional fragments of the full-length polypeptides and functional equivalents of either of the foregoing that have substantially similar or substantially identical amino acid sequences (at least about 75%, 80%, 85%, 90%, 95% 98% or more amino acid sequence similarity or identity), where the functional fragment or functional equivalent retains one or more of the functional properties of the native polypeptide.

By "functional" it is meant that the polypeptide (or nucleic acid) has the same or substantially similar activity with respect to one or more of the biological properties of the native polypeptide (or nucleic acid), e.g., at least about 50%, 75%, 85%, 90%, 95% or 98% or more of the activity of the native polypeptide (or nucleic acid).

The term "modulate" (and grammatical equivalents) refers to an increase or decrease in activity. In particular embodiments, the term "increase" or "enhance" (and grammatical equivalents) means an elevation by at least about 25%, 50%, 75%, 2-fold, 3-fold, 5-fold, 10-fold, 15-fold, 20-fold or more. In particular embodiments, the terms "decrease" or "reduce" (and grammatical equivalents) means a diminishment by at least about 25%, 40%, 50%, 60%, 75%, 80%, 85%, 90%, 95%, 98% or more. In some embodiments, the indicated activity, substance or other parameter is not detectable. Specifically provided are antagonists of EZH2.

The term "pharmacodynamic marker" refers to a molecular marker of drug response that can be measured in patients receiving the drug. The marker should be a direct measure of modulation of the drug target and be able to show quantitative changes in response to dose. A potential pharmacodynamic marker for EZH2 antagonists could be levels of histone H3-K27 methylation in disease or surrogate tissue.

As used herein, the term "responsiveness" is interchangeable with terms "responsive", "sensitive", and "sensitivity", and it is meant that a subject showing therapeutic response when administered an EZH inhibitor, e.g., tumor cells or tumor tissues of the subject undergo apoptosis and/or necrosis, and/or display reduced growing, dividing, or proliferation.

The term "control" or "reference" refers to methylation levels (e.g., monomethylation level, dimethylation level or trimethylation level) detected in an adjacent non-tumor tissue isolated from the subject, detected in a healthy tissue from a healthy subject, or established by a pathologist with standard methods in the art.

By "sample" it means any biological sample derived from the subject, includes but is not limited to, cells, tissues samples and body fluids (including, but not limited to, mucus, blood, plasma, serum, urine, saliva, and semen).

EXAMPLES

The invention now being generally described, it will be more readily understood by reference to the following examples, which are included merely for purposes of illustration of certain aspects and embodiments of the present invention, and are not intended to limit the invention.

Example 1

Recombinant Five-Component PRC2 Complex

Wild-type EZH2 (GenBank Accession No. NM_004456) or Tyr641 mutants were co-expressed with wild-type AEBP2 (GenBank Accession No. NM_153207), EED (GenBank Accession No. NM_003797), SUZ12 (GenBank Accession No. NM_015355) and RbAp48 (GenBank Accession No. NM_005610) in *Spodoptera frugiperda* (Sf9) cells using a baculovirus expression system. An N-terminal FLAG tag on the EED was used to purify active PRC2 complex from cell lysates (BPS Bioscience, catalog number 51004). The purity of the final PRC2 preparations was assessed by SDS-PAGE with Coomassie blue staining.

Example 2

H3, H4 Peptide Panel

A library consisting of 44 peptides of 15 amino acids each was synthesized by $21^{st}$ Century Biochemicals (Marlboro, Mass.). This peptide panel encompassed all of the amino acids of human histones H3 and H4 with 5 residue overlaps between consecutive peptide sequences. The N-terminus of each peptide was appended with biotin, and the C-termini were represented as the amide. Purity (>95%) and identity were confirmed by liquid chromatography/mass spectral analysis.

For study of the H3-K27 methylation status dependence of enzyme activity, peptides were synthesized representing the amino acid sequence of human H3 from residues 21-44 (H3:

21-44) with lysine 27 represented as the unmodified, monomethylated, di-methylated or tri-methylated side chain amine. These peptides were purchased from New England Peptide (Gardner, Mass.) with biotin appended to the C-terminus of each peptide.

Example 3

Evaluation of H3-K27 Methylation Status in Cells

The cell lines OCI-LY19 (ACC 528), KARPAS-422 (ACC 32), and WSU-DLCL2 (ACC 575) were obtained from DSMZ. The cell lines DB (CRL-2289) and SU-DHL2 (CRL-2959) were obtained from ATCC. OCI-LY19, WSU-DLCL2, and DB cell lines were grown in RPMI-1640 with 10% FBS, and KARPAS-422 and SU-DHL2 cell lines were grown in RPMI-1640 plus 20% FBS. Cells were grown to a density of $1.5$-$2\times10^6$ cells/mL and $1\times10^7$ cells were harvested by centrifugation at 264×g, washed in ice cold PBS and lysed by resuspension in a 10× pellet volume of RIPA lysis buffer containing 50 mM Tris-HCl, 150 mM NaCl, 0.25% DOC, 1% NP-40, and 1 mM EDTA (Millipore #20-188), plus 0.1% SDS and protease inhibitor tablets (Roche #1836153). Lysates were sonicated by 2 rounds of 10 1-second bursts at setting 3 with a Misonix XL-2000 to ensure efficient histone extraction, and cleared by centrifugation at 4° C. using a bench top centrifuge at 14,000 rpm for 10 minutes. Protein concentration was determined by BCA assay (Pierce). Four micrograms of each lysate was fractionated on 4-20% Tris-Glycine gel (Invitrogen), transferred to PVDF, and probed with the following antibodies in Odyssey blocking buffer: mouse anti-EZH2 (CST 3147; 1:2000 dilution), rabbit anti-H3-K27me3 (CST 9733; 1:10000 dilution), rabbit anti-H3-K27me2 (CST 9755; 1:5000 dilution), rabbit anti-H3-K27me1 (Active Motif 39377; 1:5000 dilution), and mouse anti-Total H3 (CST 3638; 1:20000 dilution). Following primary Ab incubation, membranes were probed with IRDye 800CW donkey-anti-mouse IgG (LiCOR #926-32212) or Alexa Fluor 680 goat-anti-rabbit IgG (Invitrogen #A-21076) secondary Ab and imaged using the LiCOR Odyssey system.

Example 4

Enzymology

As noted above, it had previously been concluded that the disease-associated changes at Tyr641 resulted in loss of function with respect to EZH2-catalyzed H3-K27 methylation. However, a presumptive reduction in the rate of H3-K27 methylation due to enzyme heterozygosity was difficult to rationalize as the basis for a malignant phenotype, especially in light of previous data indicating that overexpression of EZH2, loss-of-function mutations in the corresponding H3-K27 demethylase UTX, or overexpression of components of the PRC2, such as PHF19/PCL3, involved in increased H3-K27 trimethylation, all result in malignant phenotypes in specific human cancers. Morin et al. (2010) *Nat Genet* 42:181-5; Martinez-Garcia et al. (2010) *Nat Genet* 42:100-1; Bracken et al. (2003) *EMBO J* 22:5323-35; Kleer et al. (2003) *Proc Natl Acad Sci USA* 100:11606-11; Varambally et al. (2002) *Nature* 419:624-9; Simon et al. (2008) *Mutat Res* 647:21-9; van Haaften et al. (2009) *Nat Genet* 41:521-3; Wang et al. (2004) *Gene* 343:69-78; Cao et al. (2008) *Mol Cell Biol* 28:1862-72; and Sarma et al. (2008) *Mol Cell Biol* 28:2718-31). Therefore, the enzymology of these mutations was explored in greater detail.

Figure 1A:
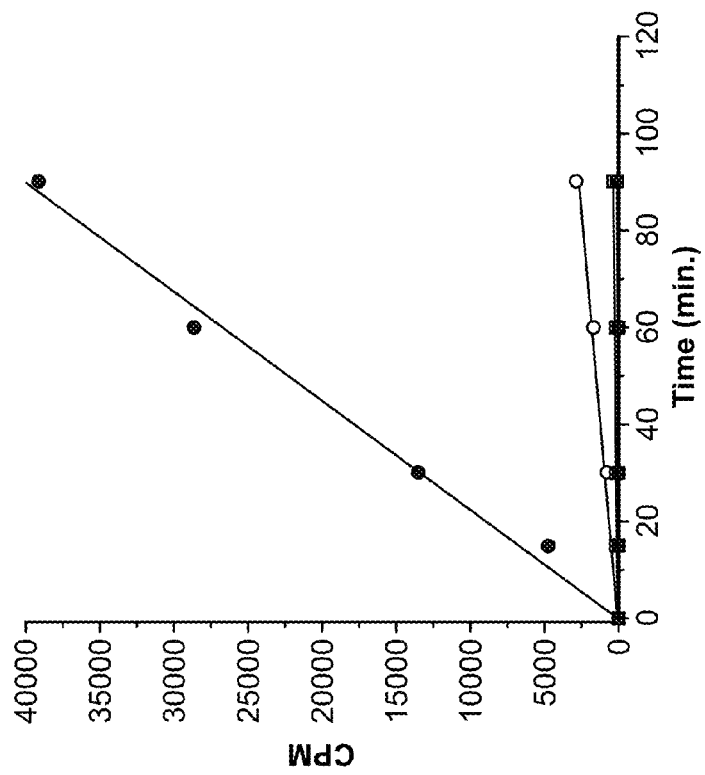
Figure 2A:
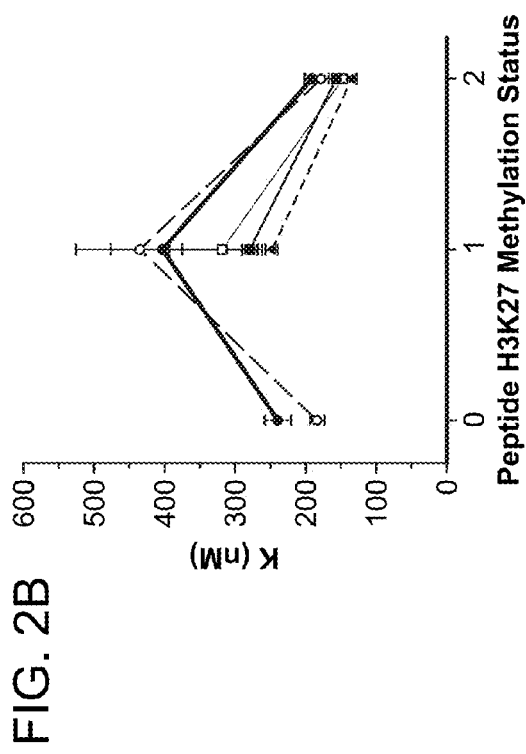
FIGS. 2A-D are four graphs establishing that PRC2 complexes containing mutant EZH2 preferentially catalyze di- and tri-methylation of histone H3-K27.
Figure 2B:
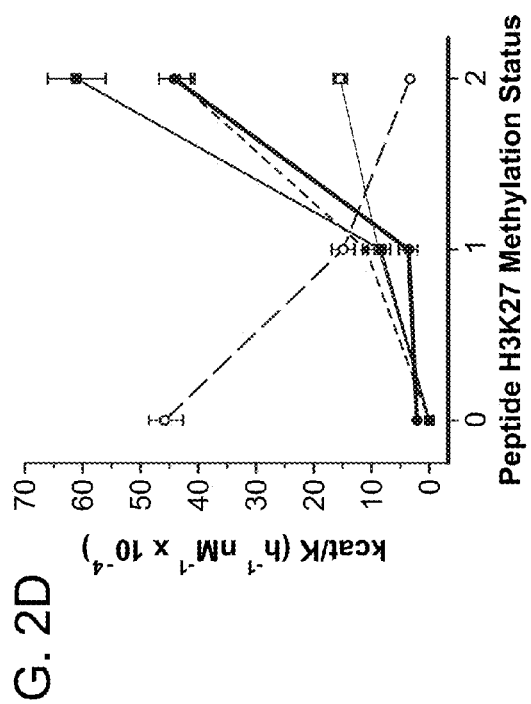
Figure 2C:
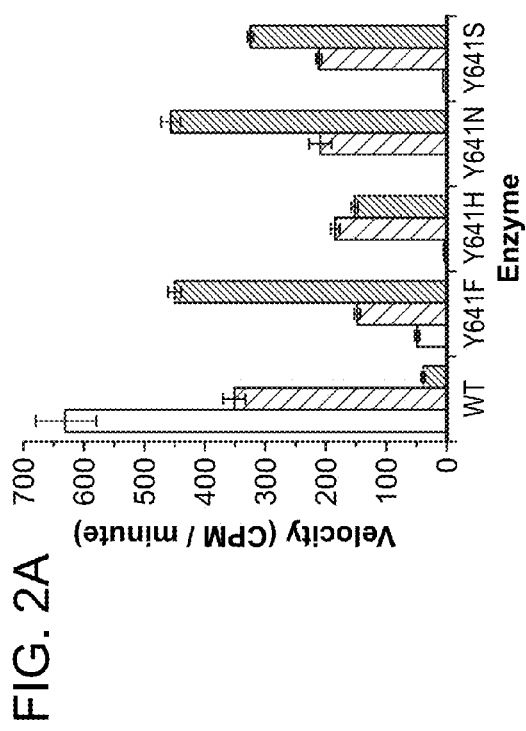
Figure 2D:
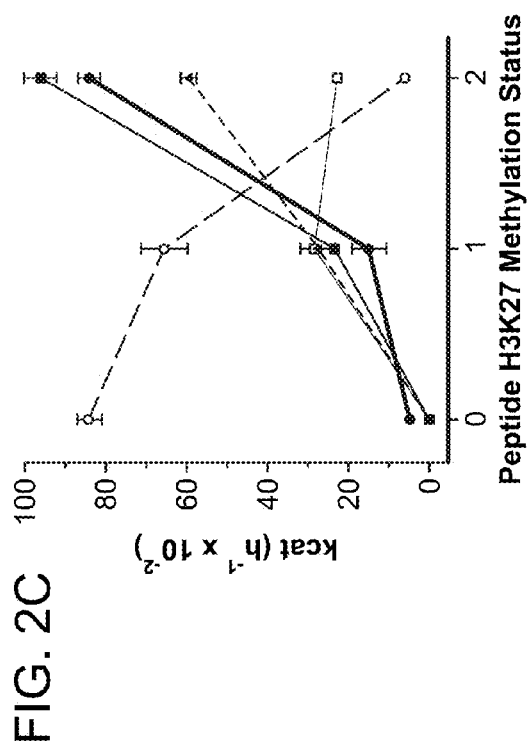

Recombinant PRC2 complexes were prepared with WT and Tyr641 mutant versions of human EZH2 (see Example 1 above; Cao et al. (2004) *Mol Cell* 15:57-67). Equal concentrations (nominally 8 nM, based on protein determinations) of each complex were initially tested for the ability to catalyze $^3$H-methyl transfer from labeled S-adenosyl methionine (SAM) to an unmodified peptide representing the amino acid sequence surrounding H3-K27 (H3:21-44) or to native avian erythrocyte oligonucleosomes. As previously reported (Morin et al. (2010) *Nat Genet* 42:181-5), it was found that the WT enzyme displayed robust activity for methyl transfer to this unmethylated peptidic substrate, but that none of the mutant enzymes displayed significant methyltransferase activity (FIG. 1A). In contrast to the previously reported data and that in FIG. 1A, it was found that all of the mutant EZH2 constructs were active methyltransferases against the avian nucleosome substrate (FIG. 1B). The nucleosomes isolated from the avian natural source represent an admixture of states of histone modification, including various states of H3-K27 methylation as judged by Western blotting with H3-K27 methylation-specific antibodies.

There are several potential explanations for the discordant activity of the mutant PRC2 complexes on peptide and nucleosome substrates. One possibility is that substrate recognition sites distal to the enzyme active site (i.e., exosites) are important determinants of substrate binding and turnover; these sites would engage complementary recognition elements on the nucleosome that are not available on small peptidic substrates. However, when *E. coli*-expressed, recombinant human histone H3 was tested as a substrate for the WT and mutant PRC2 complexes, the resulting pattern of activity was identical to that seen for the peptide substrate; that is, the WT enzyme demonstrated robust methyltransferase activity against the H3 substrate, the Y641F mutant showed 7% the activity of WT complex, and all other mutants displayed ≤1% the activity of WT complex. Hence, exosite engagement seems an unlikely explanation for the current results. The nucleosome presents many lysine residues beyond H3-K27 as potential sites of methylation that would not be present in the small peptidic substrate. Thus, another possibility is that mutation of Y641 alters the substrate specificity of EZH2 to result in methylation of lysine residues other than H3-K27. This possibility is unlikely given the excellent agreement between mutant activity on small peptide and recombinant H3 protein substrates.

The apparent discordance between the present results and those previously reported was resolved when the enzymatic activity of the WT and mutant PRC2 complexes were tested against a panel of peptidic substrates that represent all possible lysine (K) residues of histone H3 and histone H4 (see Example 2 above). All of the enzyme forms showed significant activity only against peptides containing the equivalent of residue H3-K27. The specific activity of the mutants, however, was greatly reduced relative to WT in the order WT>>Y641F>Y641S~Y641H>Y641N, again consistent with previous reported findings.

Example 5

Enzymology

To understand further the enzymatic activity of these mutants, and to reconcile the apparent discrepancy between activity against peptidic and nucleosome substrates, the ability of the enzyme forms to catalyze further methylation of various H3-K27 methylation states in the context of the H3:21-44 peptide was studied. As stated above, it was found that all of the mutant enzymes were deficient catalysts of unmodified H3-K27 peptide methylation, relative to the WT enzyme. Remarkably, however, all of the mutant enzymes were found to be superior to WT enzyme in catalyzing further methylation of the mono- and especially the di-methylated H3-K27 peptides (FIGS. 2A-D). Thus, the data suggest that the WT enzyme is most efficient in catalyzing the zero- to mono-methylation reaction. The mutant enzymes are defective in catalyzing this initial step, but are more efficient than the WT enzyme in catalyzing the subsequent steps leading from mono-methyl to di- and tri-methyl H3-K27.

The origins of the differential substrate specificities of WT and mutant EZH2 were explored through steady state enzyme kinetics. As summarized in Table 1, the mutations have minimal effects on ground-state substrate recognition, as demonstrated by the similar values of $K_m$ for nucleosome and of $K_{1/2}$ for peptide substrates. In all cases the peptidic substrates displayed sigmoidal binding behavior; hence the concentration of peptide resulting in half-maximal velocity is reported here as $K_{1/2}$ instead of the more common Michaelis constant, $K_m$. Copeland (2005) *Evaluation of Enzyme Inhibitors in Drug Discovery: A Guide to Medicinal Chemists and Pharmacologists*, Wiley. The SAM $K_m$ likewise displayed minimal variation among the enzyme forms, ranging from 208±50 to 304±64 nM. Instead, the differences in substrate utilization appear to have their origin in transition state recognition, as demonstrated by differences in $k_{cat}$ values among the enzymes for various substrates (Table 1). As a result, the catalytic efficiency, quantified as the ratio $k_{cat}/K$ (where K is either $K_m$ or $K_{1/2}$, depending on substrate identity; vide supra), varies between the WT and mutant enzymes for different states of H3-K27 methylation (Table 1).

TABLE 1

Steady state kinetic parameters for methylation reactions catalyzed by PRC2 containing wild-type or Y641 mutants of EZH2.

| Enzyme | Substrate H3-K27 Methylation Status | K (nM) | $k_{cat}$ ($h^{-1} \times 10^{-2}$) | $k_{cat}/K$ ($h^{-1} \cdot nM^{-1} \times 10^{-4}$) |
|---|---|---|---|---|
| WT | 0 | 184 ± 10 | 84.0 ± 3.0 | 45.7 ± 3.0 |
|  | 1 | 436 ± 42 | 65.4 ± 5.8 | 15.0 ± 2.0 |
|  | 2 | 178 ± 16 | 6.0 ± 0.3 | 3.4 ± 0.3 |
|  | Nucleosome | 141 ± 31 | 42.6 ± 2.6 | 30.2 ± 6.9 |
| Y641F | 0 | 240 ± 19 | 4.8 ± 0.3 | 2.0 ± 0.2 |
|  | 1 | 404 ± 124 | 15.0 ± 4.3 | 3.7 ± 1.6 |
|  | 2 | 191 ± 10 | 84.0 ± 2.8 | 44.0 ± 2.7 |
|  | Nucleosome | 176 ± 19 | 65.4 ± 2.0 | 37.2 ± 4.2 |
| Y641H | 0 | —[a] | — | — |
|  | 1 | 319 ± 57 | 28.2 ± 3.7 | 8.8 ± 2.0 |
|  | 2 | 148 ± 9 | 22.8 ± 0.9 | 15.4 ± 1.1 |
|  | Nucleosome | 140 ± 22 | 23.4 ± 1.0 | 16.7 ± 2.7 |
| Y641N | 0 | — | — | — |
|  | 1 | 280 ± 11 | 23.4 ± 0.8 | 8.4 ± 0.4 |
|  | 2 | 157 ± 11 | 96.0 ± 4.0 | 61.1 ± 5.0 |
|  | Nucleosome | 191 ± 34 | 23.4 ± 1.3 | 12.3 ± 2.3 |
| Y641S | 0 | — | — | — |
|  | 1 | 249 ± 8 | 27.6 ± 0.8 | 11.1 ± 0.5 |
|  | 2 | 136 ± 8 | 59.4 ± 2.0 | 43.7 ± 3.0 |
|  | Nucleosome | 137 ± 28 | 23.4 ± 1.4 | 17.1 ± 3.6 |

[a] Activity too low to measure.

Example 6

Enzymology

The steady state kinetic parameters listed in Table 1 made it possible to calculate the expected levels of different H3-K27 methylation states for cells heterozygous for the various mutant EZH2 forms, relative to cells homozygous for the WT enzyme. To perform these simulations, a number of simplifying assumptions were made: (1) that steady state enzyme kinetics are relevant to PRC2-catalyzed H3-K27 methylation in the cellular context and that all measurements are made at the same time point in cell growth; (2) that the mutant and WT enzyme are expressed at equal levels in heterozygous cells and that the total EZH2 level is equal in all cells; (3) that the cellular concentration of SAM, relative to its $K_m$ is saturating and does not change among the cells; (4) that the cellular concentration of nucleosome, is similar to its $K_m$ and likewise does not change among cells; (5) that EZH1 catalyzed methylation of H3-K27 was insignificant and constant among the cells; and (6) that any H3-K27 demethylase activity was also constant among the cells.

Figure 3B:
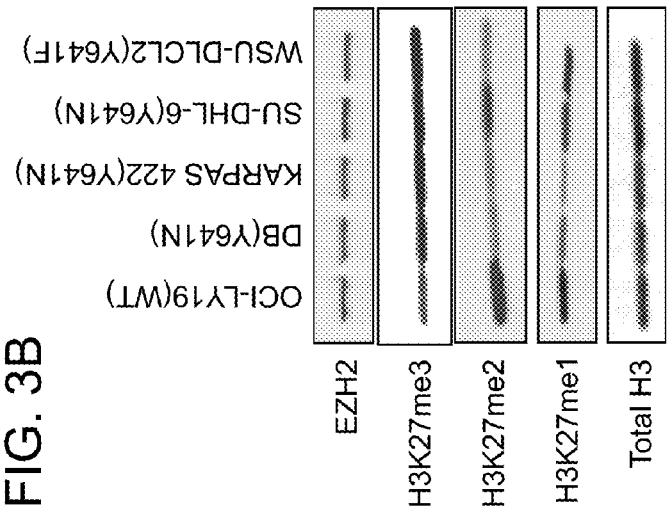
FIG. 3B is a series of Western blot analyses of relative patterns of H3-K27 methylation status for lymphoma cell lines homozygous for WT EZH2, or heterozygous for the indicated EZH2 Y641 mutation. Panels from top to bottom depict the results of probing with antibodies specific for the following: total EZH2; H3-K27me3; H3-K27me2; H3-K27me1; and total histone H3 as loading control.
Figure 3A:
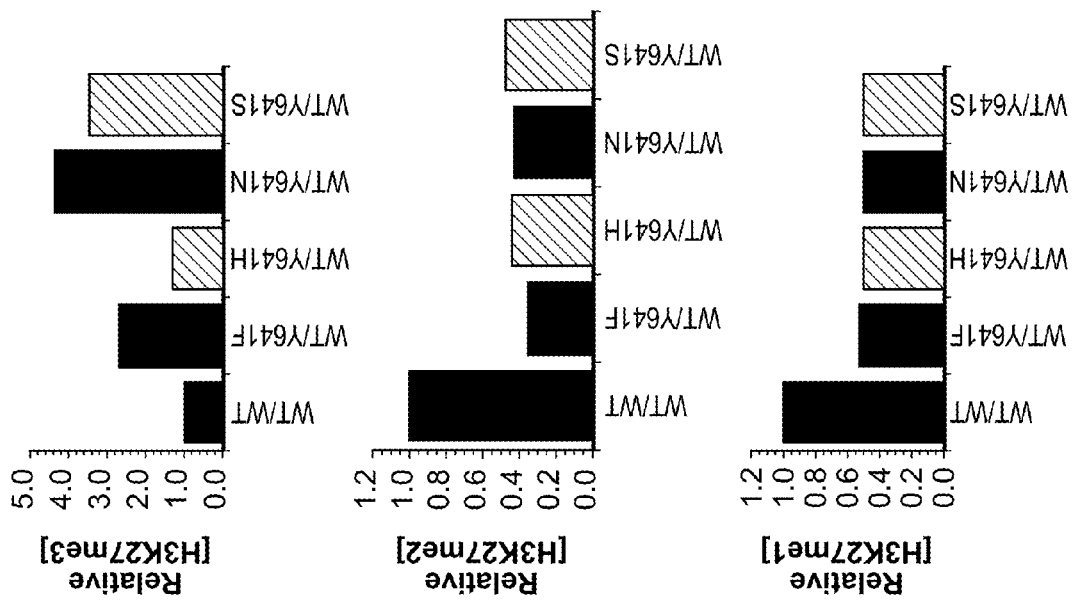
FIG. 3A is a trio of graphs depicting predicted relative levels of H3-K27me3 (top panel), H3-K27me2 (middle panel), and H3-K27me1 (bottom panel) for cells containing different EZH2 mutants. Simulations were performed using a coupled enzyme steady state velocity equation and the steady state kinetic parameters shown in Table 1. All values are relative to the homozygous WT EZH2-containing cells and assume saturating concentrations of intracellular SAM, relative to Km and intracellular nucleosome concentrations similar to Km.
Figure 4A:
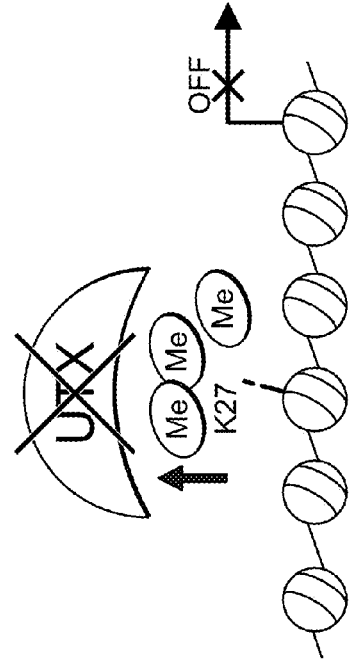
FIGS. 4A-D depict selected proposed mechanisms leading to aberrantly high levels of trimethylation on histone H3-K27 in cancer. These include.
Figure 4C:
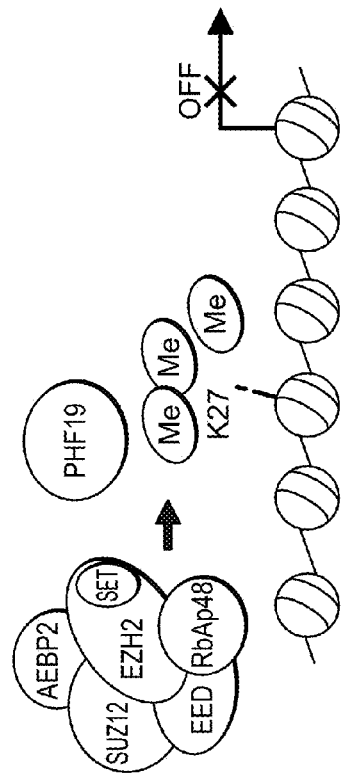
Figure 4B:
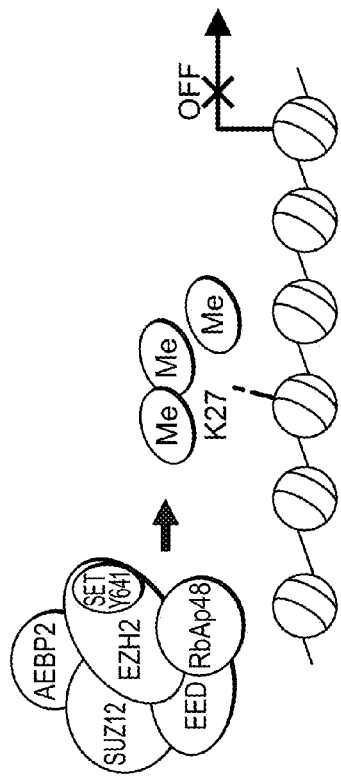
Figure 4D:
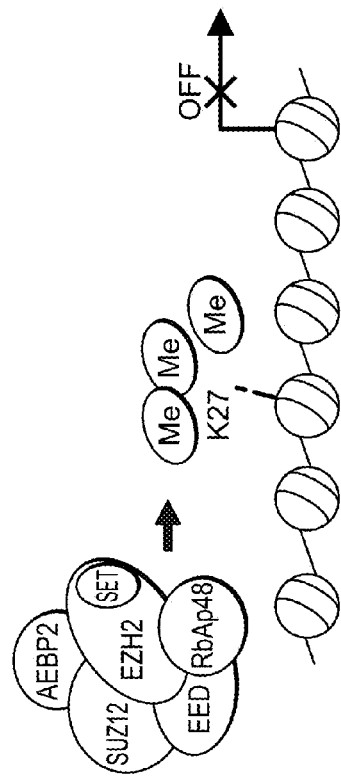
Figure 5:
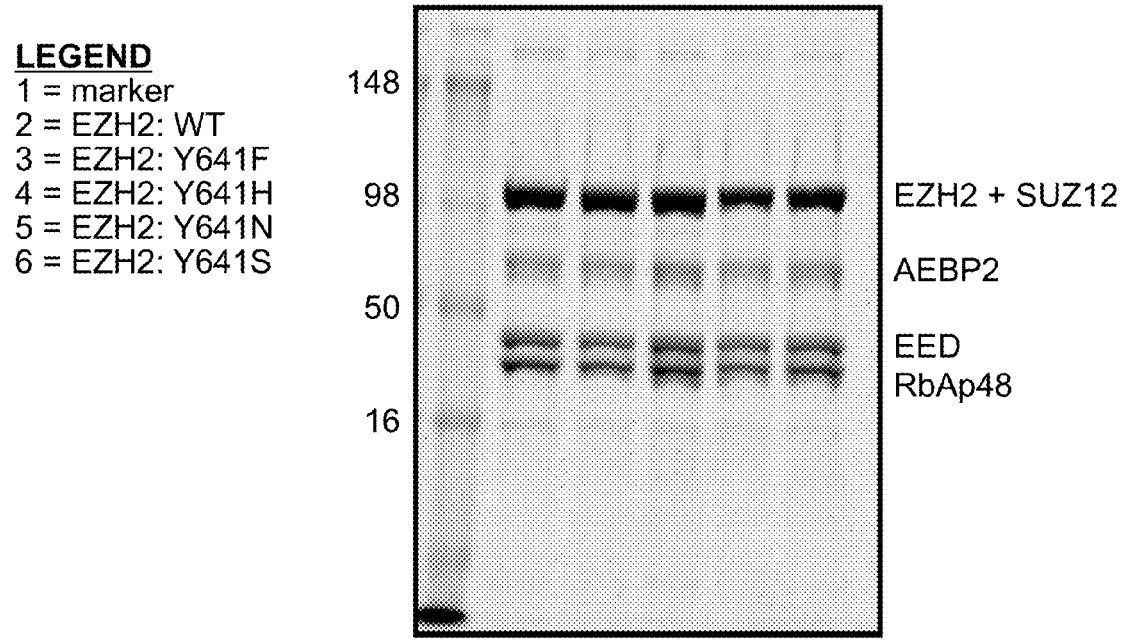
FIG. 5 depicts a SDS-PAGE gel showing that the expression levels of each of the five-component PRC2 complexes are similar with mutant and wild-type EZH2.

With these assumptions in place, the predictions illustrated in FIG. 3A were obtained for relative levels of H3-K27me3 (top panel), H3-K27me2 (middle panel) and H3-K27me1 (bottom panel). A clear pattern emerges from these simulations. The level of H3-K27me3 increases relative to WT cells for all mutant-harboring cells, ranging from a 30% increase for the Y641H mutant to >400% for the Y641N mutant. At the same time, the levels of H3-K27me2 decreases to <50% of WT for all of the mutants, and the levels of H3-K27me1 are reduced by approximately half for all mutants, relative to WT.

The relative levels of the H3-K27 methylation states in B-cell lymphoma cell lines that are known to be homozygous for WT EZH2 (OCI-LY19) or heterozygous for EZH2 Y641N (DB, KARPAS 422, and SU-DHL-6) or EZH2 Y641F (WSU-DLCL2) were then measured by Western blotting (FIG. 3B). The pattern of relative H3-K27 methylation states seen in FIG. 3b is in excellent agreement with the results of the simulations based on in vitro steady state kinetic parameters, despite the assumptions used in the simulations and the use of a non-physiological peptide surrogate as substrate.

Thus, increased H3-K27me3 was observed for all Y641 mutant-harboring cells relative to WT, decreased H3-K27me2 was observed for all Y641 mutant-harboring cells relative to WT, and decreased H3-K27me1 was observed for at least two of the four mutant cell lines. The near-comparable levels of H3-K27me1 in WT and KARPAS 422 and SU-DHL-6 cells may reflect different expression levels of WT and mutant EZH2, different contributions of EZH1, or other factors not accounted for in the simulations. Nevertheless, the concordance between the predicted and experimental patterns of H3-K27 methylation status is remarkable and supports the view that enzymatic coupling between WT and mutant EZH2 leads to increased H3-K27me3, thus resulting in the malignant phenotype of cells that are heterozygous for these mutants.

Example 7

In Vitro Assays of PRC2 Methyltransferase Activity

Flashplate Assay with Peptide Substrate.

For initial comparison of WT and Y641 mutants of EZH2, biotinylated histone H3:21-44 peptide containing unmethylated K27 (New England Peptide), monomethylated K27 (Millipore) or dimethylated K27 (Millipore) at a concentration of 800 nM was combined with a mixture of S-adenosyl-methionine-Cl (SAM) at 1,700 nM, and 300 nM tritiated SAM (Perkin Elmer). This substrate combination was then added to the PRC2 in assay buffer (20 mM BICINE, 1 mM DTT, 0.002% Tween 20, 0.005% bovine skin gelatin (BSG), pH 7.6). Reactions were allowed to proceed for the indicated time interval and then quenched by addition of excess cold SAM (600 μM final concentration). Quenched reaction mixtures were transferred to a streptavidin-coated Flashplate (Perkin Elmer, catalog number SMP410), allowed to bind for one hour, and then detected on a TopCount NXT HTS scintillation and luminescence counter (Perkin Elmer). Each time point represented the average of six individual reactions. Steady state kinetic parameters were determined under identical reaction conditions except that the concentration of peptide or SAM was varied, while at saturating conditions of the other substrate. Velocity was plotted as a function of varied substrate concentration and the data were fitted to the untransformed version of the Michaelis-Menten equation or the untransformed version of a sigmoidal kinetic equation to calculate values of K and $k_{cat}$. Standard errors of fitted parameters are listed in Table 1 and were used to construct the error bars illustrated in FIG. 2 panels B and C. Error associated with $k_{cat}/K$ (Table 1) were calculated according to standard methods of error propagation; the fractional error of $k_{cat}/K$ was determined as:

$$\mu \frac{k_{cat}}{K} = \sqrt{\left(\frac{\mu k_{cat}}{k_{cat}}\right)^2 + \left(\frac{\mu K}{K}\right)^2} \quad (1)$$

where $\mu k_{cat}$ is the standard error of $k_{cat}$ and $\mu K$ is the standard error of K.

Filterplate Assay with Oligonucleosome.

Chicken erythrocyte oligonucleosomes were purified as previously described. Fang et al. (2004) *Methods Enzymnol* 377:213-26. Nucleosomes were combined with a mixture of SAM and tritiated SAM, and added to PRC2 in assay buffer (20 mM BICINE, 100 mM KCl, 1 mM DTT, 0.002% Tween 20, 0.005% BSG, pH 7.6). Reactions were run and quenched as above. Quenched reaction mixture was transferred to a glass fiber filterplate (Millipore, catalog number MSFBN6B) and washed three times with 10% trichloroacetic acid and allowed to dry. Microscint Zero (30 μL) was added and tritium incorporation was detected on a TopCount scintillation and luminescence counter. Steady state parameters were determined under identical reaction conditions except that the concentration of nucleosome or SAM was varied while at saturating conditions of the other substrate. Velocity was plotted as a function of varied substrate concentration and fitted to the untransformed version of the Michaelis-Menten equation to derive the values of $K_m$ and $k_{cat}$ as described above.

Example 8

Preparation of Compound 75

A. Preparation of Compound 37

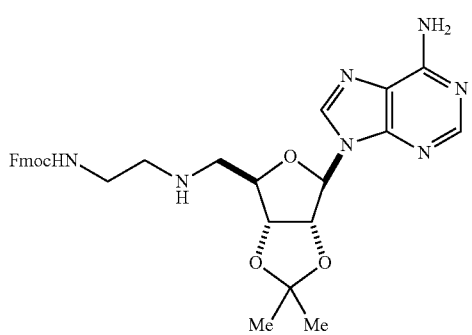

To a solution of 9-((3aR,4R,6R,6aR)-6-(aminomethyl)-2,2-dimethyltetrahydrofuro[3,4-d][1,3]dioxol-4-yl)-9H-purin-6-amine (Townsend, A. P. et al. (2009) *Org. Let.* 11:2976-2979) (3.05 g, 9.96 mmol) in DCE (250 mL) was added (9H-fluoren-9-yl)methyl(2-oxoethyl)carbamate (2.8 g, 9.96 mmol) and NaB(OAc)₃H (2.96 g, 13.95 mmol), the mixture stirred for 4 h at room temperature. K₂CO₃ solution was added to pH at 8-9. DCM was added, the organic layer was dried with Na₂SO4, concentrated and purified by SGC (DCM:MeOH=30:1) to give 37 (2.9 g, yield: 50.9%).

B. Preparation of Compound 65

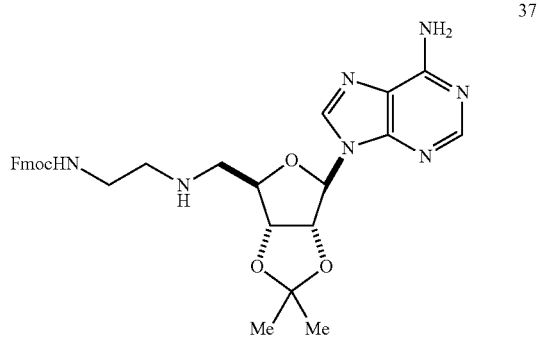

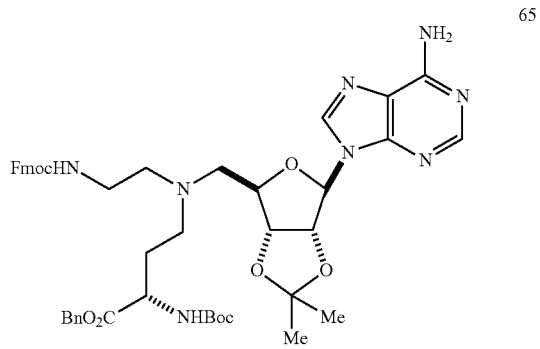

To a solution of 37 (2.9 g, 5.08 mmol) in DCE (250 mL), (S)-benzyl 2-((tert-butoxycarbonyl)amino)-4-oxobutanoate (1.56 g, 5.08 mmol) and NaB(OAc)₃H (1.51 g, 7.11 mmol) were added, the mixture stirred for 4 h at room temperature. K₂CO₃ solution was added to pH at 8-9. DCM was added, the organic layer was dried with Na₂SO₄, concentrated and purified with SGC (DCM: MeOH=100:1) to give 65 (2.8 g, yield: 63.9%).

C. Preparation of Compound 75

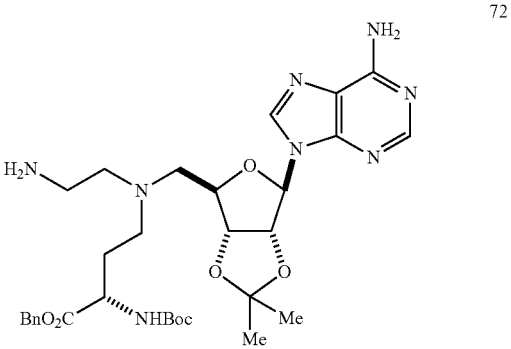

-continued

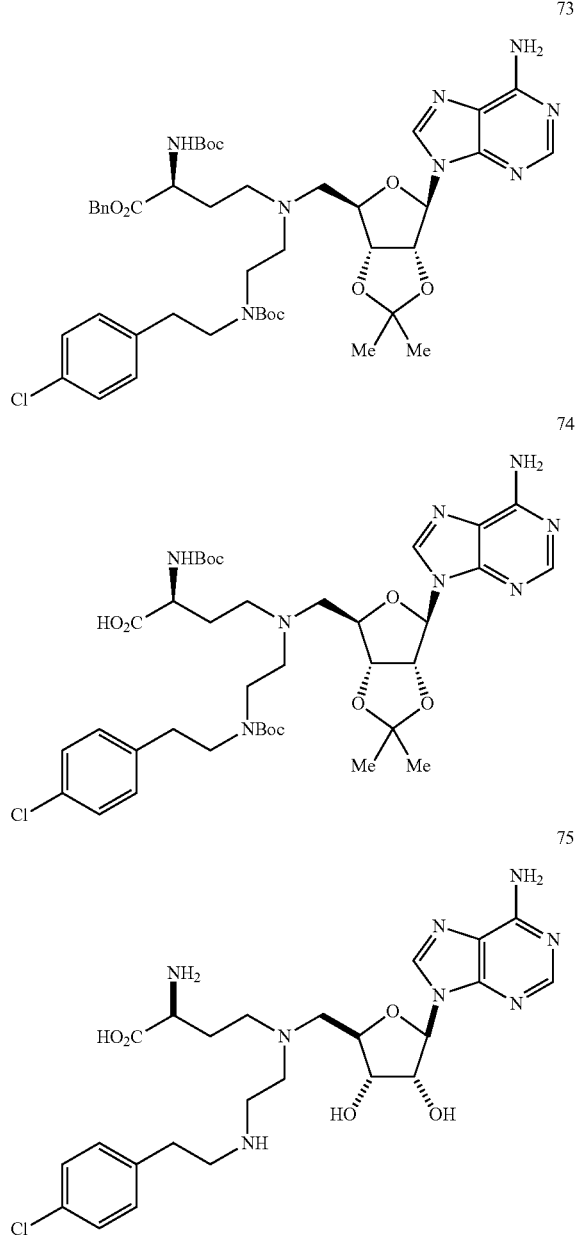

Step 1.

To a solution of 65B (2.2 g, 2.55 mmol) in DCM (10 mL), Et$_2$NH (1.1 g, 15.3 mmol) were added, the mixture stirred for 4 h at room temperature. The mixture was concentrated to give crude 72 (2.2 g).

Step 2.

To a stirred solution of 72 (167 mg, 0.26 mmol) in MeOH (4 mL), 2-(4-chlorophenyl)acetaldehyde (40 mg, 0.26 mmol) was added and stirred at room temperature for 20 min. Then Na(OAc)$_3$BH (83 mg, 0.39 mmol) and HOAc (0.4 mL) was added and stirred overnight. Then NaHCO$_3$ (aq) was added and extracted with DCM (25 mL×3), washed with brine, dried with Na$_2$SO$_4$ and concentrated. The crude product was purified by preparative TLC (DCM/MeOH=10:1) to afford 73 (30 mg, yield: 14%) as white powder. LC/MS (m/z): 779.7 [M+1]$^+$.

Step 3.

A mixture of 73 (30 mg, 0.038 mmol) and 10% Pd/C (15 mg) in MeOH (2 mL) was stirred at room temperature under H$_2$ overnight. The mixture was filtered and the filtrate was concentrated to give crude product. The crude product was purified by preparative TLC (DCM/MeOH=8:1) to afford 74 (20 mg, yield: 69%) as white powder. LC/MS (m/z): 689.7 [M+1]$^+$.

Step 4.

A solution of 74 (20 mg, 0.028 mmol) in 90% TFA (1 mL) was stirred at room temperature for 1 h, and concentrated as a solid to remove TFA to give the compound 75 (TFA salt) as a colorless oil without purification. LC/MS (m/z): 549.7 [M+1]$^+$.

Example 9

Inhibition of EZH2 Wild-Type and Y641 Mutants by SAH

S-Adenosyl-L-homocysteine (SAH) was serially diluted 3 fold in DMSO for 10 points and 1 μL was plated in a 384 well microtiter plate. Positive control (100% inhibition standard) was 100 μM final concentration of SAH and negative control (0% inhibition standard) contained 1 μL of DMSO. SAH was then incubated for 30 minutes with 40 μL per well of EZH2 wild-type and mutants at 8 nM in pH 7.6 assay buffer (20 mM BICINE, 100 mM KCl, 1 mM DTT, 0.002% Tween 20, 0.005% BSG). A substrate mix at 10 μL per well was added which contained S-adenosylmethionine-Cl (SAM) at 150 nM and tritiated SAM at 100 nM, and biotinylated oligonucleosome at 150 nM in pH 7.6 assay buffer. Quenched enzyme reaction was transferred to a streptavidin-coated Flashplate (Perkin Elmer, catalog number SMP410), allowed to bind for one hour, and detected on a TopCount NXT HTS (Perkin Elmer).

Figure 7:
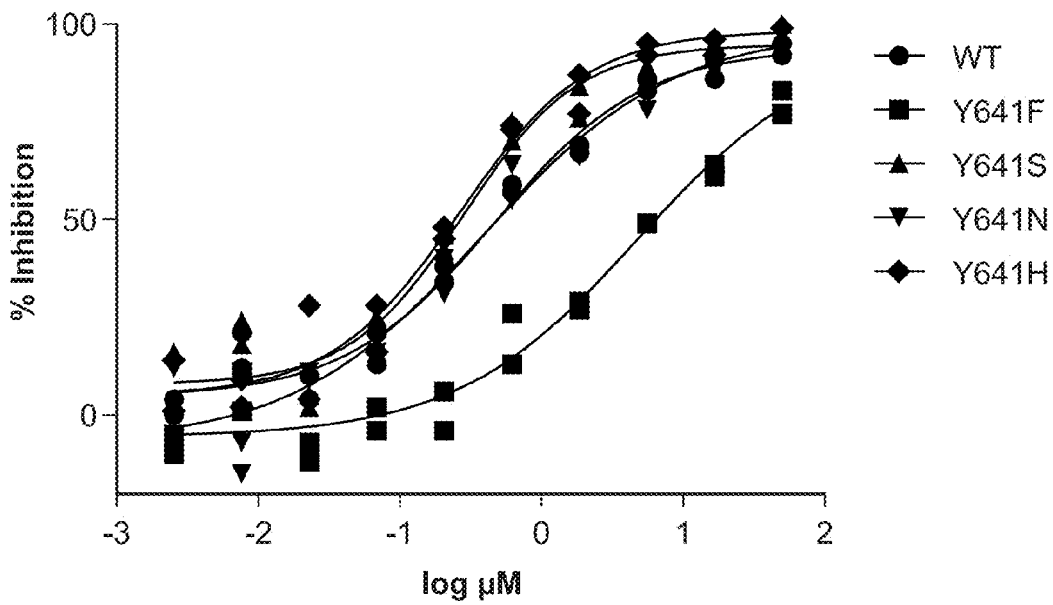
FIG. 7 is a graph depicting inhibitory potency of S-adenosyl-L-homocysteine (SAH) against EZH2 WT and Y641 mutants of EZH2. The X axis shows log concentration of SAH; the Y axis shows percent inhibition.

Results are shown in FIG. 7. IC50 values are shown in Table 2.

TABLE 2

Inhibition of WT EZH2 and Y641 mutants of EZH2 by SAH.

| | WT | Y641H | Y641S | Y641N | Y641F |
|---|---|---|---|---|---|
| IC50, μM | 0.467 | 0.263 | 0.283 | 0.380 | 4.80 |

Example 10

Inhibition of EZH2 Wild-Type and Y641 Mutants by Compound 75

Compound 75 was serially diluted 3 fold in DMSO for 10 points and 1 μL was plated in a 384 well microtiter plate. Positive control (100% inhibition standard) was 100 μM final concentration of SAH and negative control (0% inhibition standard) contained 1 μL of DMSO. Compound 75 was then incubated for 30 minutes with 40 μL per well of EZH2 wild-type and mutants at 8 nM in pH 7.6 assay buffer (20 mM BICINE, 100 mM KCl, 1 mM DTT, 0.002% Tween 20, 0.005% BSG). A substrate mix at 10 μL per well was added which contained S-adenosylmethionine-Cl (SAM) at 150 nM and tritiated SAM at 100 nM, and biotinylated oligonucleosome at 150 nM in pH 7.6 assay buffer. Quenched enzyme reaction was transferred to a streptavidin-coated Flashplate (Perkin Elmer, catalog number SMP410), allowed to bind for one hour, and detected on a TopCount NXT HTS (Perkin Elmer).

Figure 8:
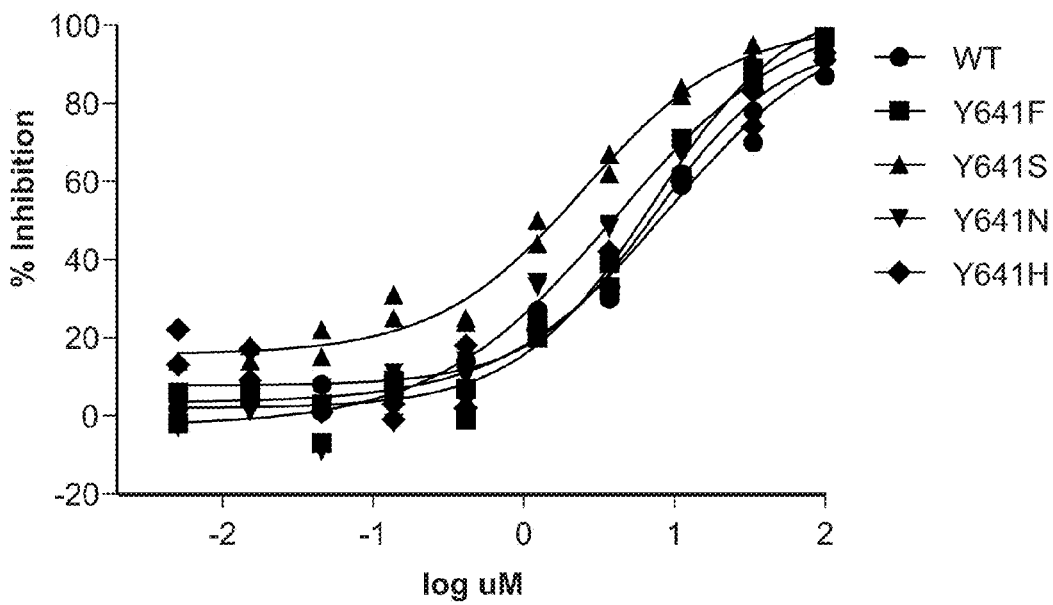
FIG. 8 is a graph depicting inhibitory potency of Compound 75 against EZH2 WT and Y641 mutants of EZH2. The X axis shows log concentration of Compound 75; the Y axis shows percent inhibition.

Results are shown in FIG. 8. IC50 values are shown in Table 3.

TABLE 3

Inhibition of WT EZH2 and Y641 mutants of EZH2 by Compound 75.

|          | WT   | Y641S | Y641N | Y641F | Y641H |
|----------|------|-------|-------|-------|-------|
| IC50, µM | 8.95 | 2.50  | 4.10  | 7.18  | 7.56  |

Example 11

H3-K27me2/me3 Ratios Predict Sensitivity to an EZH2 Inhibitor

Tumor cell lines heterozygous for the EZH2 (Y641) mutation display increased levels of H3-K27me3, the methylation state of H3-K27 thought to be important in tumorigenesis. Levels of the mono (H3-K27me1), di (H3-K27me2), or tri-methylated (H3-K27me3) forms of H3-K27 in a panel of cell lines that were WT for EZH2, or heterozygous for EZH2 (Y641) mutations were evaluated. Cell lines used are listed in Table 4. The majority of lines are B-cell lymphoma lines, however two melanoma lines were also included. IGR1 is a melanoma line that has recently been found to contain a Y641N mutation in EZH2, and A375 cells were included as a WT EZH2 melanoma control line. FIGS. 9A and 9B show the results of western blot analysis of histones isolated from this cell line panel probed with antibodies recognizing H3-K27me1, H3-K27me2, or H3-K27me3. In general, global H3-K27me3 levels are higher in Y641 mutant containing cell lines than in cell lines expressing WT EZH2 exclusively. Two exceptions are Farage and Pfeiffer cells, where H3-K27me3 levels were similar to those in WT lines. More striking are the dramatically lower levels of H3-K27me2 in EZH2 Y641 mutant cell lines relative to wild type cell lines. Little or no H3-K27me2 signal was observed in western blot of histones extracted from Y641 mutant cell lines, whereas the signal observed with the same antibody in WT cell lines was more intense than that observed with the antibody specific for H3-K27me3. Overall, in WT cell lines the western blot signal with an HK27me2 antibody was higher than the signal observed with the H3-K27me3 antibody, whereas the opposite was true in Y641 mutant cell lines. Thus the ratio of H3-K27me3/me2 signal in Y641 lines is higher than that observed in WT lines. The one exception to this is the Pfeiffer cell line, which does not contain a Y641 EZH2 mutation, but has high H3-K27me3 signal, and little or no H3-K27me2 signal. Pfeiffer cells therefore have a H3-K27me3/me2 ratio similar to Y641 mutant cell lines.

The H3-K27 methylation state can also be examined by Mass spectrometry (MS), an independent method that does not rely on antibody reagents. The MS analysis demonstrated that H3-K27me3 levels are higher in Y641 mutant and Pfeiffer lines than in the other WT lines, whereas the opposite is true for H3-K27me2 levels. In the Y641 mutant and Pfeiffer lines, H3-K27me3 levels were higher than H3-K27me2 levels, whereas the opposite was true in the other WT lines. These results are consistent with those observed by western blot analysis in FIGS. 9A and 9B.

The differences in H3-K27 methylation state was also detected by immunocytochemistry using antibodies to H3-K27me2 or H3-K27me3. This immunohistochemistry assay is used for detecting aberrant H3-K27me2/3 ratios associated with Y641 mutant EZH2 in formalin fixed paraffin embedded patient tumor tissue samples. A panel of five WT and five Y641 mutant lymphoma cell line pellets were fixed and embedded in paraffin blocks and stained with anti-H3-K27me2 or H3-K27me3 antibodies. An antibody to histone H3 was included as a positive control, since all cells should contain nuclear histone H3. FIG. 10 shows that all cell lines were positive in 100% of cells for both H3-K27me3 and H3 staining. Under these conditions, no clear difference in H3-K27me3 staining intensity was observed between WT and Y641 mutant cell lines. This may reflect the limited dynamic range of chromogenic immunocytochemistry staining compared to other methods of detection. However, as shown in FIG. 11, cell lines could be clearly segregated into those staining positive or negative for H3-K27me2. All WT cell lines, with the exception of Pfeiffer cells, stained positive for H3-K27me2, whereas all Y641 mutant cell lines and Pfeiffer cells showed no staining with the H3-K27me2 antibody. These results are consistent with those obtained by western and MS analysis.

Figure 12:
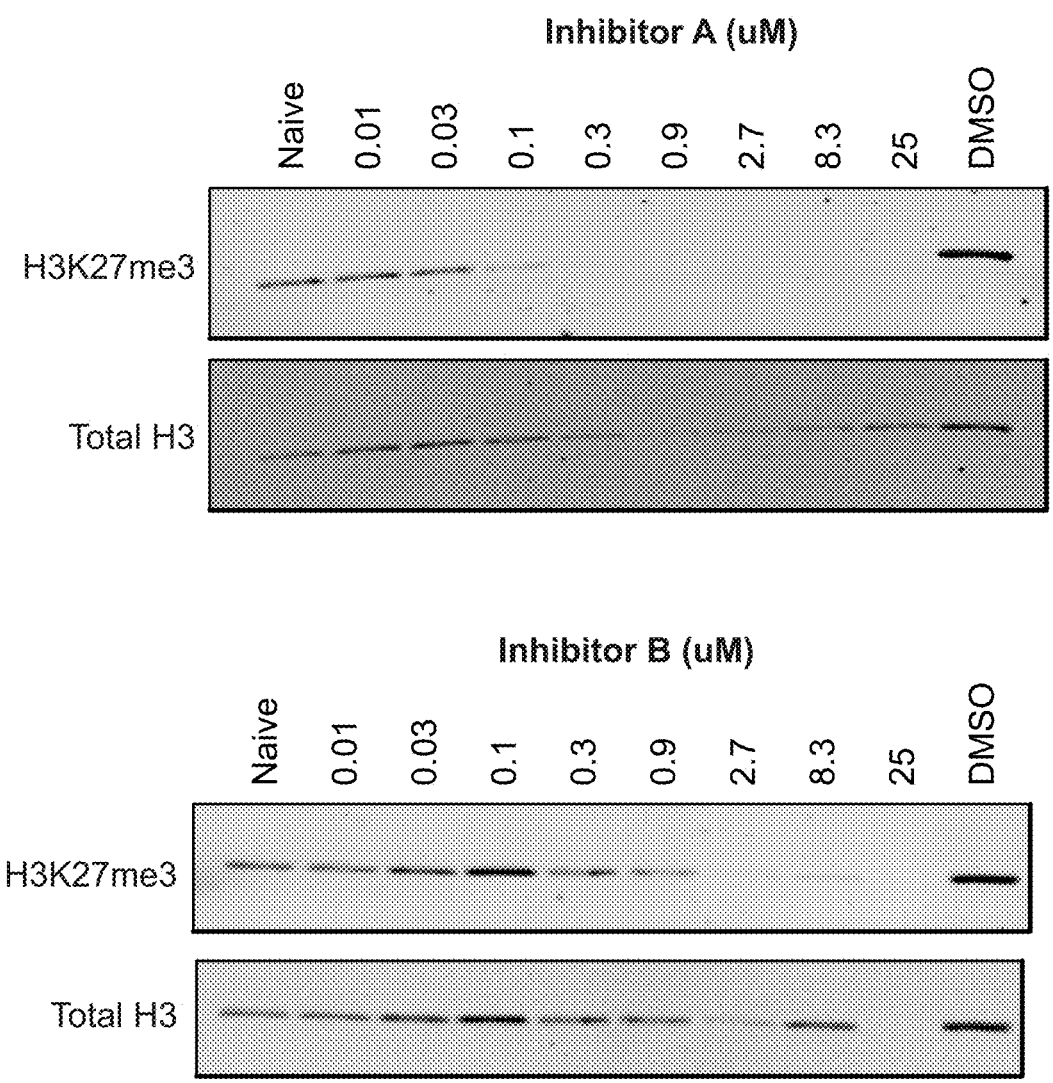
FIG. 12 is a graph depicting the inhibition of global H3-K27me3 levels by EZH2 inhibitor treatment in Y641 mutant WSU-DLCL2 cells. WSU-DLCL2 cells were treated for 4 days with the indicated concentrations of EZH2 inhibitor A or B. Following compound treatment, histones were extracted, fractionated by SDS-PAGE on a 4-20% gel, transferred to nitrocellulose membranes, and probed with antibodies to Histone H3, or H3-K27me3.

Without wishing to be bound by theory, the increased levels of H3-K27me3 associated with the gain of function EZH2 (Y641) mutations may render cells bearing EZH2 mutations more sensitive to small molecule EZH2 inhibitors. To evaluate whether the increased H3-K27me3 and/or decreased H3-K27me2 levels observed in Pfeiffer cells in the absence of an EZH2 Y641 mutation would also correlate with sensitivity to EZH2 inhibitors, two compounds that demonstrate potent inhibition of EZH2 in biochemical assays with IC50s of 85 and 16 nM respectively were tested. Treatment of WSU-DLCL2 cells with either compound led to inhibition of global H3-K27me3 levels, confirming their ability to enter cells and inhibit cellular EZH2 methyltransferase activity (FIG. 12).

Figure 14A:
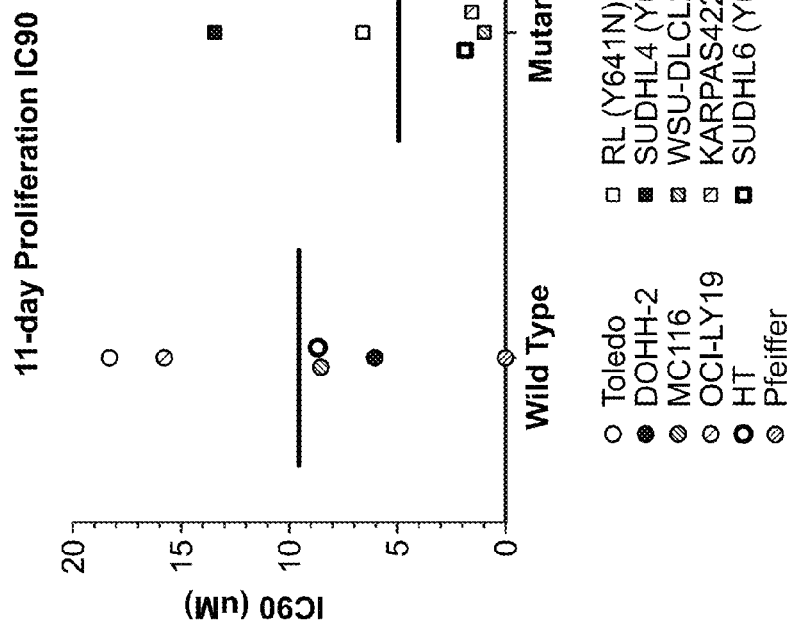

The sensitivity of a panel of WT and Y641 mutant cell lines to each compound was evaluated in proliferation assays. Because the anti-proliferative activity of EZH2 inhibitors takes several days to manifest, compounds were assessed in 11-day proliferation assays. FIG. 13 shows representative growth curves for WT (OCI-LY19), or Y641 mutant (WSU-DLCL2) cell lines treated with the test compounds. Both compounds demonstrated anti-proliferative activity against WSU-DLCL2 cells, but little activity against OCI-LY19 cells. Inhibitor A was a more potent inhibitor of WSU-DLCL2 proliferation than Inhibitor B and this is consistent with Inhibitor A being a more potent inhibitor of EZH2 in biochemical assays. Proliferation assays were performed in a panel of WT and Y641 mutant lymphoma cell lines, with Inhibitor B, and day 11 IC90 values were derived. FIG. 14A shows IC90 values of lymphoma cell lines grouped by EZH2 Y641 status. Overall, Y641 mutant cell lines demonstrated increased sensitivity to EZH2 inhibitors relative to WT cell lines, although RL and SUDHL4 cells were significantly less sensitive than other mutant lines. Pfeiffer cells are an exception, since they are WT, but are highly sensitive to the anti-proliferative effects of both compounds with IC90s in the low or sub-nanomolar range. Pfeiffer cells demonstrate high H3-K27me3 and low H3-K27me2 levels, and so grouping cell lines according to high H3-K27me3 and low H3-K27me2 gives better discrimination of EZH2 inhibitor sensitivity as shown for Inhibitor B in FIG. 14B.

Thus, high H3-K27me3 and low H3-K27me2 levels can be used to predict sensitivity to EZH2 inhibitors, independent of knowledge of mutational status. The aberrant methylation ratio observed in Pfeiffer cells occurs by a separate mechanism that confers dependence upon EZH2 activity.

These results demonstrates that identifying EZH2 Y641 mutations in patient tumors and/or detecting low levels of H3-K27me2 relative to H3-K27me3 through use of techniques such as western blot, MS or IHC in a patient can be used to identify which patient will respond to EZH2 inhibitor treatment.

TABLE 4

Cell lines used in this study.

| Cancer | EZH2 Status | Cell Line |
|---|---|---|
| Lymphoma: DLBCL (Diffuse Large Cell B Cell Lymphoma) and other B-cell Lymphoma | Wild Type | OCI-LY19 |
| | | HT |
| | | MC116 |
| | | BC-1 |
| | | BC-3 |
| | | Pfeiffer |
| | | Toledo |
| | | DOHH-2 |
| | | Farage |
| | | SR |
| | | NU-DHL-1 |
| | | NU-DUL-1 |
| | Y641 Mutation | SU-DHL-10 (Y641F) |
| | | DB (Y641N) |
| | | KARPAS 422 (Y641N) |
| | | SU-DHL-6 (Y641N) |
| | | WSU-DLCL-2 (Y641F) |
| | | RL (Y641N) |
| | | SU-DHL-4 (Y641S) |
| Melanoma | Wild Type | A375 |
| | Y641 Mutation | IGR-1 (Y641N) |

EQUIVALENTS

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

We claim:

1. A method for treating cancer in a subject, comprising (i) contacting a biological sample obtained from the subject with at least one antibody that binds specifically to a mutant Enhancer of Zeste Homolog 2 (EZH2) comprising a mutation at position Y641 in the EZH2 of SEQ ID NO: 1, wherein the mutation increases EZH2 trimethylation of Lys27 of histone H3 (H3-K27), wherein the mutation at position Y641 in the EZH2 of SEQ ID NO: 1 is selected from the group consisting of Y641F, Y641H, Y641N and Y641S, and wherein the at least one antibody and the mutant form a complex;
   (ii) detecting the presence of the mutation at position Y641 in the EZH2 of SEQ ID NO: 1 by detecting the complex formed in step (i); and
   (iii) administering a therapeutically effective amount of an inhibitor of EZH2 to the subject if the mutation at position Y641 in the EZH2 of SEQ ID NO: 1 is detected in the biological sample obtained from the subject, wherein the EZH2 inhibitor inhibits the conversion of H3-K27 to trimethylated H3-K27.

2. The method of claim 1, wherein said subject has a cancer selected from leukemia, melanoma, and lymphoma, or is at risk of developing a cancer selected from leukemia, melanoma, and lymphoma.

3. The method of claim 2, wherein said lymphoma is selected from the group consisting of Non-Hodgkin's lymphoma, follicular lymphoma and diffuse large B-cell lymphoma (DLBCL) of germinal center B cell-like (GCB) subtype.

4. The method of claim 1, wherein inhibition of EZH2 is selective inhibition.

5. The method claim 1, wherein the inhibitor of EZH2 is a small molecule.

6. The method of claim 1, wherein the cancer is lymphoma.

* * * * *

SEQUENCE LISTING

```
<160> NUMBER OF SEQ ID NOS: 13

<210> SEQ ID NO 1
<211> LENGTH: 746
<212> TYPE: PRT
<213> ORGANISM: Homo sapiens

<400> SEQUENCE: 1

Met Gly Gln Thr Gly Lys Lys Ser Glu Lys Gly Pro Val Cys Trp Arg
1               5                   10                  15

Lys Arg Val Lys Ser Glu Tyr Met Arg Leu Arg Gln Leu Lys Arg Phe
            20                  25                  30

Arg Arg Ala Asp Glu Val Lys Ser Met Phe Ser Ser Asn Arg Gln Lys
        35                  40                  45

Ile Leu Glu Arg Thr Glu Ile Leu Asn Gln Glu Trp Lys Gln Arg Arg
    50                  55                  60

Ile Gln Pro Val His Ile Leu Thr Ser Val Ser Ser Leu Arg Gly Thr
65                  70                  75                  80

Arg Glu Cys Ser Val Thr Ser Asp Leu Asp Phe Pro Thr Gln Val Ile
                85                  90                  95

Pro Leu Lys Thr Leu Asn Ala Val Ala Ser Val Pro Ile Met Tyr Ser
            100                 105                 110

Trp Ser Pro Leu Gln Gln Asn Phe Met Val Glu Asp Glu Thr Val Leu
        115                 120                 125

His Asn Ile Pro Tyr Met Gly Asp Glu Val Leu Asp Gln Asp Gly Thr
    130                 135                 140

Phe Ile Glu Glu Leu Ile Lys Asn Tyr Asp Gly Lys Val His Gly Asp
145                 150                 155                 160
```

```
Arg Glu Cys Gly Phe Ile Asn Asp Glu Ile Phe Val Glu Leu Val Asn
            165                 170                 175
Ala Leu Gly Gln Tyr Asn Asp Asp Asp Asp Asp Gly Asp Asp
        180                 185                 190
Pro Glu Glu Arg Glu Glu Lys Gln Lys Asp Leu Glu Asp His Arg Asp
            195                 200                 205
Asp Lys Glu Ser Arg Pro Pro Arg Lys Phe Pro Ser Asp Lys Ile Phe
    210                 215                 220
Glu Ala Ile Ser Ser Met Phe Pro Asp Lys Gly Thr Ala Glu Glu Leu
225                 230                 235                 240
Lys Glu Lys Tyr Lys Glu Leu Thr Glu Gln Gln Leu Pro Gly Ala Leu
                245                 250                 255
Pro Pro Glu Cys Thr Pro Asn Ile Asp Gly Pro Asn Ala Lys Ser Val
            260                 265                 270
Gln Arg Glu Gln Ser Leu His Ser Phe His Thr Leu Phe Cys Arg Arg
        275                 280                 285
Cys Phe Lys Tyr Asp Cys Phe Leu His Pro Phe His Ala Thr Pro Asn
    290                 295                 300
Thr Tyr Lys Arg Lys Asn Thr Glu Thr Ala Leu Asp Asn Lys Pro Cys
305                 310                 315                 320
Gly Pro Gln Cys Tyr Gln His Leu Glu Gly Ala Lys Glu Phe Ala Ala
                325                 330                 335
Ala Leu Thr Ala Glu Arg Ile Lys Thr Pro Pro Lys Arg Pro Gly Gly
            340                 345                 350
Arg Arg Arg Gly Arg Leu Pro Asn Asn Ser Ser Arg Pro Ser Thr Pro
        355                 360                 365
Thr Ile Asn Val Leu Glu Ser Lys Asp Thr Asp Ser Asp Arg Glu Ala
    370                 375                 380
Gly Thr Glu Thr Gly Gly Glu Asn Asn Asp Lys Glu Glu Glu Glu Lys
385                 390                 395                 400
Lys Asp Glu Thr Ser Ser Ser Ser Glu Ala Asn Ser Arg Cys Gln Thr
                405                 410                 415
Pro Ile Lys Met Lys Pro Asn Ile Glu Pro Pro Glu Asn Val Glu Trp
            420                 425                 430
Ser Gly Ala Glu Ala Ser Met Phe Arg Val Leu Ile Gly Thr Tyr Tyr
        435                 440                 445
Asp Asn Phe Cys Ala Ile Ala Arg Leu Ile Gly Thr Lys Thr Cys Arg
    450                 455                 460
Gln Val Tyr Glu Phe Arg Val Lys Glu Ser Ser Ile Ile Ala Pro Ala
465                 470                 475                 480
Pro Ala Glu Asp Val Asp Thr Pro Pro Arg Lys Lys Lys Arg Lys His
                485                 490                 495
Arg Leu Trp Ala Ala His Cys Arg Lys Ile Gln Leu Lys Lys Asp Gly
            500                 505                 510
Ser Ser Asn His Val Tyr Asn Tyr Gln Pro Cys Asp His Pro Arg Gln
        515                 520                 525
Pro Cys Asp Ser Ser Cys Pro Cys Val Ile Ala Gln Asn Phe Cys Glu
    530                 535                 540
Lys Phe Cys Gln Cys Ser Ser Glu Cys Gln Asn Arg Phe Pro Gly Cys
545                 550                 555                 560
Arg Cys Lys Ala Gln Cys Asn Thr Lys Gln Cys Pro Cys Tyr Leu Ala
                565                 570                 575
Val Arg Glu Cys Asp Pro Asp Leu Cys Leu Thr Cys Gly Ala Ala Asp
```

```
              580                 585                 590
His Trp Asp Ser Lys Asn Val Ser Cys Lys Asn Cys Ser Ile Gln Arg
                595                 600                 605

Gly Ser Lys Lys His Leu Leu Leu Ala Pro Ser Asp Val Ala Gly Trp
            610                 615                 620

Gly Ile Phe Ile Lys Asp Pro Val Gln Lys Asn Glu Phe Ile Ser Glu
625                 630                 635                 640

Tyr Cys Gly Glu Ile Ile Ser Gln Asp Glu Ala Asp Arg Arg Gly Lys
                645                 650                 655

Val Tyr Asp Lys Tyr Met Cys Ser Phe Leu Phe Asn Leu Asn Asn Asp
            660                 665                 670

Phe Val Val Asp Ala Thr Arg Lys Gly Asn Lys Ile Arg Phe Ala Asn
            675                 680                 685

His Ser Val Asn Pro Asn Cys Tyr Ala Lys Val Met Met Val Asn Gly
            690                 695                 700

Asp His Arg Ile Gly Ile Phe Ala Lys Arg Ala Ile Gln Thr Gly Glu
705                 710                 715                 720

Glu Leu Phe Phe Asp Tyr Arg Tyr Ser Gln Ala Asp Ala Leu Lys Tyr
                725                 730                 735

Val Gly Ile Glu Arg Glu Met Glu Ile Pro
            740                 745

<210> SEQ ID NO 2
<211> LENGTH: 2723
<212> TYPE: DNA
<213> ORGANISM: Homo sapiens

<400> SEQUENCE: 2
ggcggcgctt gattgggctg gggggggccaa ataaaagcga tggcgattgg gctgccgcgt    60
ttggcgctcg gtccggtcgc gtccgacacc cggtgggact cagaaggcag tggagccccg   120
gcggcggcgg cggcggcgcg cggggggcgac gcgcgggaac aacgcgagtc ggcgcgcggg   180
acgaagaata atcatgggcc agactgggaa gaaatctgag aagggaccag tttgttggcg   240
gaagcgtgta aaatcagagt acatgcgact gagacagctc aagaggttca gacgagctga   300
tgaagtaaag agtatgttta gttccaatcg tcagaaaatt ttggaaagaa cggaaatctt   360
aaaccaagaa tggaaacagc gaaggataca gcctgtgcac atcctgactt ctgtgagctc   420
attgcgcggg actagggagt gttcggtgac cagtgacttg gattttccaa cacaagtcat   480
cccattaaag actctgaatg cagttgcttc agtacccata atgtattctt ggtctcccct   540
acagcagaat tttatggtgg aagatgaaac tgttttacat aacattcctt atatgggaga   600
tgaagtttta gatcaggatg gtactttcat tgaagaacta ataaaaaatt atgatgggaa   660
agtacacggg gatagagaat gtgggtttat aaatgatgaa attttttgtgg agttggtgaa   720 tgcccttggt caatataatg atgatgacga tgatgatgat ggagacgatc ctgaagaaag   780
agaagaaaag cagaaagatc tggaggatca ccgagatgat aaagaaagcc gcccacctcg   840
gaaatttcct tctgataaaa ttttttgaagc catttcctca atgtttccag ataagggcac   900
agcagaagaa ctaaaggaaa aatataagaa actcaccgaa cagcagctcc caggcgcact   960
tcctcctgaa tgtaccccca acatagatgg accaaatgct aaatctgttc agagagagca  1020
aagcttacac tcctttcata cgcttttctg taggcgatgt tttaaatatg actgcttcct  1080
acatcgtaag tgcaattatt cttttcatgc aacacccaac acttataagc ggaagaacac  1140
agaaacagct ctagacaaca aaccttgtgg accacagtgt taccagcatt ggagggagc   1200
```

```
aaaggagttt gctgctgctc tcaccgctga gcggataaag accccaccaa aacgtccagg    1260
aggccgcaga agaggacggc ttcccaataa cagtagcagg cccagcaccc ccaccattaa    1320
tgtgctggaa tcaaaggata cagacagtga tagggaagca gggactgaaa cggggggaga    1380
gaacaatgat aaagaagaag aagagaagaa agatgaaact tcgagctcct ctgaagcaaa    1440
ttctcggtgt caaacaccaa taaagatgaa gccaaatatt gaacctcctg agaatgtgga    1500
gtggagtggt gctgaagcct caatgtttag agtcctcatt ggcacttact atgacaattt    1560
ctgtgccatt gctaggttaa ttgggaccaa acatgtaga caggtgtatg agtttagagt    1620
caaagaatct agcatcatag ctccagctcc cgctgaggat gtggatactc ctccaaggaa    1680
aaagaagagg aaacaccggt tgtgggctgc acactgcaga aagatacagc tgaaaaagga    1740
cggctcctct aaccatgttt acaactatca accctgtgat catccacggc agccttgtga    1800
cagttcgtgc ccttgtgtga tagcacaaaa ttttgtgaa aagttttgtc aatgtagttc    1860
agagtgtcaa aaccgctttc cgggatgccg ctgcaaagca cagtgcaaca ccaagcagtg    1920
cccgtgctac ctggctgtcc gagagtgtga ccctgacctc tgtcttactt gtggagccgc    1980
tgaccattgg gacagtaaaa atgtgtcctg caagaactgc agtattcagc ggggctccaa    2040
aaagcatcta ttgctggcac catctgacgt ggcaggctgg gggattttta tcaaagatcc    2100
tgtgcagaaa aatgaattca tctcagaata ctgtggagag attatttctc aagatgaagc    2160
tgacagaaga gggaaagtgt atgataaata catgtgcagc tttctgttca acttgaacaa    2220
tgattttgtg gtggatgcaa cccgcaaggg taacaaaatt cgttttgcaa atcattcggt    2280
aaatccaaac tgctatgcaa aagttatgat ggttaacggt gatcacagga taggtatttt    2340
tgccaagaga gccatccaga ctggcgaaga gctgtttttt gattacagat acagccaggc    2400
tgatgccctg aagtatgtcg gcatcgaaag agaaatggaa atcccttgac atctgctacc    2460
tcctcccccc tcctctgaaa cagctgcctt agcttcagga acctcgagta ctgtgggcaa    2520
tttagaaaaa gaacatgcag tttgaaattc tgaatttgca aagtactgta agaataattt    2580
atagtaatga gtttaaaaat caactttta ttgccttctc accagctgca aagtgttttg    2640
taccagtgaa ttttgcaat aatgcagtat ggtacatttt tcaactttga ataaagaata    2700
cttgaacttg tccttgttga atc                                          2723
```

<210> SEQ ID NO 3
<211> LENGTH: 751
<212> TYPE: PRT
<213> ORGANISM: Homo sapiens

<400> SEQUENCE: 3

```
Met Gly Gln Thr Gly Lys Lys Ser Glu Lys Gly Pro Val Cys Trp Arg
1               5                   10                  15

Lys Arg Val Lys Ser Glu Tyr Met Arg Leu Arg Gln Leu Lys Arg Phe
            20                  25                  30

Arg Arg Ala Asp Glu Val Lys Ser Met Phe Ser Ser Asn Arg Gln Lys
        35                  40                  45

Ile Leu Glu Arg Thr Glu Ile Leu Asn Gln Glu Trp Lys Gln Arg Arg
    50                  55                  60

Ile Gln Pro Val His Ile Leu Thr Ser Val Ser Ser Leu Arg Gly Thr
65                  70                  75                  80

Arg Glu Cys Ser Val Thr Ser Asp Leu Asp Phe Pro Thr Gln Val Ile
                85                  90                  95
```

```
Pro Leu Lys Thr Leu Asn Ala Val Ala Ser Val Pro Ile Met Tyr Ser
                100                 105                 110

Trp Ser Pro Leu Gln Gln Asn Phe Met Val Glu Asp Glu Thr Val Leu
            115                 120                 125

His Asn Ile Pro Tyr Met Gly Asp Glu Val Leu Asp Gln Asp Gly Thr
        130                 135                 140

Phe Ile Glu Glu Leu Ile Lys Asn Tyr Asp Gly Lys Val His Gly Asp
145                 150                 155                 160

Arg Glu Cys Gly Phe Ile Asn Asp Glu Ile Phe Val Glu Leu Val Asn
                165                 170                 175

Ala Leu Gly Gln Tyr Asn Asp Asp Asp Asp Asp Gly Asp
            180                 185                 190

Pro Glu Glu Arg Glu Glu Lys Gln Lys Asp Leu Glu Asp His Arg Asp
            195                 200                 205

Asp Lys Glu Ser Arg Pro Pro Arg Lys Phe Pro Ser Asp Lys Ile Phe
210                 215                 220

Glu Ala Ile Ser Ser Met Phe Pro Asp Lys Gly Thr Ala Glu Glu Leu
225                 230                 235                 240

Lys Glu Lys Tyr Lys Glu Leu Thr Glu Gln Gln Leu Pro Gly Ala Leu
                245                 250                 255

Pro Pro Glu Cys Thr Pro Asn Ile Asp Gly Pro Asn Ala Lys Ser Val
            260                 265                 270

Gln Arg Glu Gln Ser Leu His Ser Phe His Thr Leu Phe Cys Arg Arg
            275                 280                 285

Cys Phe Lys Tyr Asp Cys Phe Leu His Arg Lys Cys Asn Tyr Ser Phe
290                 295                 300

His Ala Thr Pro Asn Thr Tyr Lys Arg Lys Asn Thr Glu Thr Ala Leu
305                 310                 315                 320

Asp Asn Lys Pro Cys Gly Pro Gln Cys Tyr Gln His Leu Glu Gly Ala
                325                 330                 335

Lys Glu Phe Ala Ala Ala Leu Thr Ala Glu Arg Ile Lys Thr Pro Pro
            340                 345                 350

Lys Arg Pro Gly Gly Arg Arg Arg Gly Arg Leu Pro Asn Asn Ser Ser
            355                 360                 365

Arg Pro Ser Thr Pro Thr Ile Asn Val Leu Glu Ser Lys Asp Thr Asp
370                 375                 380

Ser Asp Arg Glu Ala Gly Thr Glu Thr Gly Gly Glu Asn Asn Asp Lys
385                 390                 395                 400

Glu Glu Glu Glu Lys Lys Asp Glu Thr Ser Ser Ser Glu Ala Asn
                405                 410                 415

Ser Arg Cys Gln Thr Pro Ile Lys Met Lys Pro Asn Ile Glu Pro Pro
            420                 425                 430

Glu Asn Val Glu Trp Ser Gly Ala Glu Ala Ser Met Phe Arg Val Leu
            435                 440                 445

Ile Gly Thr Tyr Tyr Asp Asn Phe Cys Ala Ile Ala Arg Leu Ile Gly
            450                 455                 460

Thr Lys Thr Cys Arg Gln Val Tyr Glu Phe Arg Val Lys Glu Ser Ser
465                 470                 475                 480

Ile Ile Ala Pro Ala Pro Ala Glu Asp Val Asp Thr Pro Pro Arg Lys
                485                 490                 495

Lys Lys Arg Lys His Arg Leu Trp Ala Ala His Cys Arg Lys Ile Gln
            500                 505                 510

Leu Lys Lys Asp Gly Ser Ser Asn His Val Tyr Asn Tyr Gln Pro Cys
```

```
                515                 520                 525
Asp His Pro Arg Gln Pro Cys Asp Ser Ser Cys Pro Cys Val Ile Ala
    530                 535                 540

Gln Asn Phe Cys Glu Lys Phe Cys Gln Cys Ser Ser Glu Cys Gln Asn
545                 550                 555                 560

Arg Phe Pro Gly Cys Arg Cys Lys Ala Gln Cys Asn Thr Lys Gln Cys
                565                 570                 575

Pro Cys Tyr Leu Ala Val Arg Glu Cys Asp Pro Asp Leu Cys Leu Thr
            580                 585                 590

Cys Gly Ala Ala Asp His Trp Asp Ser Lys Asn Val Ser Cys Lys Asn
        595                 600                 605

Cys Ser Ile Gln Arg Gly Ser Lys Lys His Leu Leu Leu Ala Pro Ser
    610                 615                 620

Asp Val Ala Gly Trp Gly Ile Phe Ile Lys Asp Pro Val Gln Lys Asn
625                 630                 635                 640

Glu Phe Ile Ser Glu Tyr Cys Gly Glu Ile Ile Ser Gln Asp Glu Ala
                645                 650                 655

Asp Arg Arg Gly Lys Val Tyr Asp Lys Tyr Met Cys Ser Phe Leu Phe
            660                 665                 670

Asn Leu Asn Asn Asp Phe Val Val Asp Ala Thr Arg Lys Gly Asn Lys
        675                 680                 685

Ile Arg Phe Ala Asn His Ser Val Asn Pro Asn Cys Tyr Ala Lys Val
    690                 695                 700

Met Met Val Asn Gly Asp His Arg Ile Gly Ile Phe Ala Lys Arg Ala
705                 710                 715                 720

Ile Gln Thr Gly Glu Glu Leu Phe Phe Asp Tyr Arg Tyr Ser Gln Ala
                725                 730                 735

Asp Ala Leu Lys Tyr Val Gly Ile Glu Arg Glu Met Glu Ile Pro
            740                 745                 750

<210> SEQ ID NO 4
<211> LENGTH: 2591
<212> TYPE: DNA
<213> ORGANISM: Homo sapiens

<400> SEQUENCE: 4
ggcggcgctt gattgggctg ggggggccaa ataaaagcga tgcgattgg gctgccgcgt    60 ttggcgctcg gtccggtcgc gtccgacacc cggtgggact cagaaggcag tggagccccg   120
gcggcggcgg cggcggcgcg cggggggcgac gcgcgggaac aacgcgagtc ggcgcgcggg   180
acgaagaata atcatgggcc agactgggaa gaaatctgag aagggaccag tttgttggcg   240
gaagcgtgta aaatcagagt acatgcgact gagacagctc aagaggttca gacgagctga   300
tgaagtaaag agtatgttta gttccaatcg tcagaaaatt ttggaaagaa cggaaatctt   360
aaaccaagaa tggaaacagc gaaggataca gcctgtgcac atcctgactt ctgtgagctc   420
attgcgcggg actagggagg tggaagatga aactgtttta cataacattc cttatatggg   480
agatgaagtt ttagatcagg atggtacttt cattgaagaa ctaataaaaa attatgatgg   540
gaaagtacac ggggatagag aatgtgggtt tataaatgat gaaattttg tggagttggt   600 gaatgccctt ggtcaatata tgatgatga cgatgatgat gatgggagcg atcctgaaga   660
aagagaagaa aagcagaaag atctggagga tcaccgagat gataaagaaa gccgcccacc   720
tcggaaattt ccttctgata aaatttttga agccatttcc tcaatgtttc agataaggg    780 cacagcagaa gaactaaagg aaaaatataa agaactcacc gaacagcagc tcccaggcgc   840
```

```
acttcctcct gaatgtaccc ccaacataga tggaccaaat gctaaatctg ttcagagaga      900
gcaaagctta cactcctttc atacgctttt ctgtaggcga tgttttaaat atgactgctt      960
cctacatcct tttcatgcaa cacccaacac ttataagcgg aagaacacag aaacagctct     1020
agacaacaaa ccttgtggac cacagtgtta ccagcatttg gagggagcaa aggagtttgc     1080
tgctgctctc accgctgagc ggataaagac cccaccaaaa cgtccaggag gccgcagaag     1140
aggacggctt cccaataaca gtagcaggcc cagcaccccc accattaatg tgctggaatc     1200
aaaggataca gacagtgata gggaagcagg gactgaaacg ggggagaga acaatgataa      1260 agaagaagaa gagaagaaag atgaaacttc gagctcctct gaagcaaatt ctcggtgtca     1320
aacaccaata aagatgaagc caaatattga acctcctgag aatgtggagt ggagtggtgc     1380
tgaagcctca atgtttagag tcctcattgg cacttactat gacaatttct gtgccattgc     1440
taggttaatt gggaccaaaa catgtagaca ggtgtatgag tttagagtca agaatctag      1500 catcatagct ccagctcccg ctgaggatgt ggatactcct ccaaggaaaa agaagaggaa     1560
acaccggttg tgggctgcac actgcagaaa gatacagctg aaaaaggacg gctcctctaa     1620
ccatgtttac aactatcaac cctgtgatca tccacggcag ccttgtgaca gttcgtgccc     1680
ttgtgtgata gcacaaaatt tttgtgaaaa gttttgtcaa tgtagttcag agtgtcaaaa     1740
ccgctttccg ggatgccgct gcaaagcaca gtgcaacacc aagcagtgcc cgtgctacct     1800
ggctgtccga gagtgtgacc ctgacctctg tcttacttgt ggagccgctg accattggga     1860
cagtaaaaat gtgtcctgca agaactgcag tattcagcgg ggctccaaaa agcatctatt     1920
gctggcacca tctgacgtgg caggctgggg gatttttatc aaagatcctg tgcagaaaaa     1980
tgaattcatc tcagaatact gtggagagat tatttctcaa gatgaagctg acagaagagg     2040
gaaagtgtat gataaataca tgtgcagctt tctgttcaac ttgaacaatg attttgtggt     2100
ggatgcaacc cgcaagggta acaaaattcg ttttgcaaat cattcggtaa atccaaactg     2160
ctatgcaaaa gttatgatgg ttaacggtga tcacaggata ggtattttg ccaagagagc      2220 catccagact ggcgaagagc tgttttttga ttacagatac agccaggctg atgccctgaa     2280
gtatgtcggc atcgaaagag aaatggaaat cccttgacat ctgctacctc ctccccctc      2340 ctctgaaaca gctgccttag cttcaggaac ctcgagtact gtgggcaatt tagaaaaaga     2400
acatgcagtt tgaaattctg aatttgcaaa gtactgtaag aataatttat agtaatgagt     2460
ttaaaaatca acttttttatt gccttctcac cagctgcaaa gtgttttgta ccagtgaatt     2520
tttgcaataa tgcagtatgg tacattttttc aactttgaat aaagaatact tgaacttgtc     2580
cttgttgaat c                                                         2591
```

<210> SEQ ID NO 5
<211> LENGTH: 707
<212> TYPE: PRT
<213> ORGANISM: Homo sapiens

<400> SEQUENCE: 5

Met Gly Gln Thr Gly Lys Lys Ser Glu Lys Gly Pro Val Cys Trp Arg
1               5                   10                  15

Lys Arg Val Lys Ser Glu Tyr Met Arg Leu Arg Gln Leu Lys Arg Phe
            20                  25                  30

Arg Arg Ala Asp Glu Val Lys Ser Met Phe Ser Ser Asn Arg Gln Lys
        35                  40                  45

Ile Leu Glu Arg Thr Glu Ile Leu Asn Gln Glu Trp Lys Gln Arg Arg

```
                50              55                  60
Ile Gln Pro Val His Ile Leu Thr Ser Val Ser Ser Leu Arg Gly Thr
 65                  70                  75                  80

Arg Glu Val Glu Asp Glu Thr Val Leu His Asn Ile Pro Tyr Met Gly
                 85                  90                  95

Asp Glu Val Leu Asp Gln Asp Gly Thr Phe Ile Glu Glu Leu Ile Lys
            100                 105                 110

Asn Tyr Asp Gly Lys Val His Gly Asp Arg Glu Cys Gly Phe Ile Asn
            115                 120                 125

Asp Glu Ile Phe Val Glu Leu Val Asn Ala Leu Gly Gln Tyr Asn Asp
            130                 135                 140

Asp Asp Asp Asp Asp Gly Asp Asp Pro Glu Glu Arg Glu Glu Lys
145                 150                 155                 160

Gln Lys Asp Leu Glu Asp His Arg Asp Lys Glu Ser Arg Pro Pro
            165                 170                 175

Arg Lys Phe Pro Ser Asp Lys Ile Phe Glu Ala Ile Ser Ser Met Phe
            180                 185                 190

Pro Asp Lys Gly Thr Ala Glu Glu Leu Lys Glu Lys Tyr Lys Glu Leu
            195                 200                 205

Thr Glu Gln Gln Leu Pro Gly Ala Leu Pro Pro Glu Cys Thr Pro Asn
210                 215                 220

Ile Asp Gly Pro Asn Ala Lys Ser Val Gln Arg Glu Gln Ser Leu His
225                 230                 235                 240

Ser Phe His Thr Leu Phe Cys Arg Arg Cys Phe Lys Tyr Asp Cys Phe
                245                 250                 255

Leu His Pro Phe His Ala Thr Pro Asn Thr Tyr Lys Arg Lys Asn Thr
            260                 265                 270

Glu Thr Ala Leu Asp Asn Lys Pro Cys Gly Pro Gln Cys Tyr Gln His
            275                 280                 285

Leu Glu Gly Ala Lys Glu Phe Ala Ala Ala Leu Thr Ala Glu Arg Ile
            290                 295                 300

Lys Thr Pro Pro Lys Arg Pro Gly Gly Arg Arg Arg Gly Arg Leu Pro
305                 310                 315                 320

Asn Asn Ser Ser Arg Pro Ser Thr Pro Thr Ile Asn Val Leu Glu Ser
                325                 330                 335

Lys Asp Thr Asp Ser Asp Arg Glu Ala Gly Thr Glu Thr Gly Gly Glu
            340                 345                 350

Asn Asn Asp Lys Glu Glu Glu Lys Lys Asp Glu Thr Ser Ser Ser
            355                 360                 365

Ser Glu Ala Asn Ser Arg Cys Gln Thr Pro Ile Lys Met Lys Pro Asn
            370                 375                 380

Ile Glu Pro Pro Glu Asn Val Glu Trp Ser Gly Ala Glu Ala Ser Met
385                 390                 395                 400

Phe Arg Val Leu Ile Gly Thr Tyr Tyr Asp Asn Phe Cys Ala Ile Ala
                405                 410                 415

Arg Leu Ile Gly Thr Lys Thr Cys Arg Gln Val Tyr Glu Phe Arg Val
            420                 425                 430

Lys Glu Ser Ser Ile Ile Ala Pro Ala Pro Ala Glu Asp Val Asp Thr
            435                 440                 445

Pro Pro Arg Lys Lys Lys Arg Lys His Arg Leu Trp Ala Ala His Cys
            450                 455                 460

Arg Lys Ile Gln Leu Lys Lys Asp Gly Ser Ser Asn His Val Tyr Asn
465                 470                 475                 480
```

```
Tyr Gln Pro Cys Asp His Pro Arg Gln Pro Cys Asp Ser Ser Cys Pro
                485                 490                 495

Cys Val Ile Ala Gln Asn Phe Cys Glu Lys Phe Cys Gln Cys Ser Ser
            500                 505                 510

Glu Cys Gln Asn Arg Phe Pro Gly Cys Arg Cys Lys Ala Gln Cys Asn
        515                 520                 525

Thr Lys Gln Cys Pro Cys Tyr Leu Ala Val Arg Glu Cys Asp Pro Asp
    530                 535                 540

Leu Cys Leu Thr Cys Gly Ala Ala Asp His Trp Asp Ser Lys Asn Val
545                 550                 555                 560

Ser Cys Lys Asn Cys Ser Ile Gln Arg Gly Ser Lys Lys His Leu Leu
                565                 570                 575

Leu Ala Pro Ser Asp Val Ala Gly Trp Gly Ile Phe Ile Lys Asp Pro
            580                 585                 590

Val Gln Lys Asn Glu Phe Ile Ser Glu Tyr Cys Gly Glu Ile Ile Ser
        595                 600                 605

Gln Asp Glu Ala Asp Arg Arg Gly Lys Val Tyr Asp Lys Tyr Met Cys
    610                 615                 620

Ser Phe Leu Phe Asn Leu Asn Asn Asp Phe Val Val Asp Ala Thr Arg
625                 630                 635                 640

Lys Gly Asn Lys Ile Arg Phe Ala Asn His Ser Val Asn Pro Asn Cys
                645                 650                 655

Tyr Ala Lys Val Met Met Val Asn Gly Asp His Arg Ile Gly Ile Phe
            660                 665                 670

Ala Lys Arg Ala Ile Gln Thr Gly Glu Glu Leu Phe Phe Asp Tyr Arg
        675                 680                 685

Tyr Ser Gln Ala Asp Ala Leu Lys Tyr Val Gly Ile Glu Arg Glu Met
    690                 695                 700

Glu Ile Pro
705

<210> SEQ ID NO 6
<211> LENGTH: 114
<212> TYPE: PRT
<213> ORGANISM: Homo sapiens

<400> SEQUENCE: 6

His Leu Leu Leu Ala Pro Ser Asp Val Ala Gly Trp Gly Ile Phe Ile
1               5                   10                  15

Lys Asp Pro Val Gln Lys Asn Glu Phe Ile Ser Glu Tyr Cys Gly Glu
            20                  25                  30

Ile Ile Ser Gln Asp Glu Ala Asp Arg Arg Gly Lys Val Tyr Asp Lys
        35                  40                  45

Tyr Met Cys Ser Phe Leu Phe Asn Leu Asn Asn Asp Phe Val Val Asp
    50                  55                  60

Ala Thr Arg Lys Gly Asn Lys Ile Arg Phe Ala Asn His Ser Val Asn
65                  70                  75                  80

Pro Asn Cys Tyr Ala Lys Val Met Met Val Asn Gly Asp His Arg Ile
                85                  90                  95

Gly Ile Phe Ala Lys Arg Ala Ile Gln Thr Gly Glu Glu Leu Phe Phe
            100                 105                 110

Asp Tyr

<210> SEQ ID NO 7
```

<211> LENGTH: 342
<212> TYPE: DNA
<213> ORGANISM: Homo sapiens

<400> SEQUENCE: 7

```
catctattgc tggcaccatc tgacgtggca ggctggggga tttttatcaa agatcctgtg    60
cagaaaaatg aattcatctc agaatactgt ggagagatta tttctcaaga tgaagctgac   120
agaagaggga agtgtatga taaatacatg tgcagctttc tgttcaactt gaacaatgat   180
tttgtggtgg atgcaacccg caagggtaac aaaattcgtt ttgcaaatca ttcggtaaat   240
ccaaactgct atgcaaaagt tatgatggtt aacggtgatc acaggatagg tattttgcc    300
aagagagcca tccagactgg cgaagagctg ttttttgatt ac                      342
```

<210> SEQ ID NO 8
<211> LENGTH: 746
<212> TYPE: PRT
<213> ORGANISM: Homo sapiens
<220> FEATURE:
<221> NAME/KEY: MISC_FEATURE
<222> LOCATION: (641)..(641)
<223> OTHER INFORMATION: Wherein X can be any amino acid residue other
      than tyrosine (Y)

<400> SEQUENCE: 8

```
Met Gly Gln Thr Gly Lys Lys Ser Glu Lys Gly Pro Val Cys Trp Arg
1               5                   10                  15

Lys Arg Val Lys Ser Glu Tyr Met Arg Leu Arg Gln Leu Lys Arg Phe
            20                  25                  30

Arg Arg Ala Asp Glu Val Lys Ser Met Phe Ser Ser Asn Arg Gln Lys
        35                  40                  45

Ile Leu Glu Arg Thr Glu Ile Leu Asn Gln Glu Trp Lys Gln Arg Arg
    50                  55                  60

Ile Gln Pro Val His Ile Leu Thr Ser Val Ser Ser Leu Arg Gly Thr
65                  70                  75                  80

Arg Glu Cys Ser Val Thr Ser Asp Leu Asp Phe Pro Thr Gln Val Ile
                85                  90                  95

Pro Leu Lys Thr Leu Asn Ala Val Ala Ser Val Pro Ile Met Tyr Ser
            100                 105                 110

Trp Ser Pro Leu Gln Gln Asn Phe Met Val Glu Asp Glu Thr Val Leu
        115                 120                 125

His Asn Ile Pro Tyr Met Gly Asp Glu Val Leu Asp Gln Asp Gly Thr
    130                 135                 140

Phe Ile Glu Glu Leu Ile Lys Asn Tyr Asp Gly Lys Val His Gly Asp
145                 150                 155                 160

Arg Glu Cys Gly Phe Ile Asn Asp Glu Ile Phe Val Glu Leu Val Asn
                165                 170                 175

Ala Leu Gly Gln Tyr Asn Asp Asp Asp Asp Asp Gly Asp Asp
            180                 185                 190

Pro Glu Glu Arg Glu Glu Lys Gln Lys Asp Leu Glu Asp His Arg Asp
        195                 200                 205

Asp Lys Glu Ser Arg Pro Pro Arg Lys Phe Pro Ser Asp Lys Ile Phe
    210                 215                 220

Glu Ala Ile Ser Ser Met Phe Pro Asp Lys Gly Thr Ala Glu Glu Leu
225                 230                 235                 240

Lys Glu Lys Tyr Lys Glu Leu Thr Glu Gln Gln Leu Pro Gly Ala Leu
                245                 250                 255
```

```
Pro Pro Glu Cys Thr Pro Asn Ile Asp Gly Pro Asn Ala Lys Ser Val
            260                 265                 270

Gln Arg Glu Gln Ser Leu His Ser Phe His Thr Leu Phe Cys Arg Arg
        275                 280                 285

Cys Phe Lys Tyr Asp Cys Phe Leu His Pro Phe His Ala Thr Pro Asn
    290                 295                 300

Thr Tyr Lys Arg Lys Asn Thr Glu Thr Ala Leu Asp Asn Lys Pro Cys
305                 310                 315                 320

Gly Pro Gln Cys Tyr Gln His Leu Glu Gly Ala Lys Glu Phe Ala Ala
                325                 330                 335

Ala Leu Thr Ala Glu Arg Ile Lys Thr Pro Lys Arg Pro Gly Gly
            340                 345                 350

Arg Arg Gly Arg Leu Pro Asn Asn Ser Ser Arg Pro Ser Thr Pro
        355                 360                 365

Thr Ile Asn Val Leu Glu Ser Lys Asp Thr Asp Ser Asp Arg Glu Ala
    370                 375                 380

Gly Thr Glu Thr Gly Gly Glu Asn Asn Asp Lys Glu Glu Glu Glu Lys
385                 390                 395                 400

Lys Asp Glu Thr Ser Ser Ser Glu Ala Asn Ser Arg Cys Gln Thr
                405                 410                 415

Pro Ile Lys Met Lys Pro Asn Ile Glu Pro Pro Glu Asn Val Glu Trp
                420                 425                 430

Ser Gly Ala Glu Ala Ser Met Phe Arg Val Leu Ile Gly Thr Tyr Tyr
            435                 440                 445

Asp Asn Phe Cys Ala Ile Ala Arg Leu Ile Gly Thr Lys Thr Cys Arg
    450                 455                 460

Gln Val Tyr Glu Phe Arg Val Lys Glu Ser Ser Ile Ile Ala Pro Ala
465                 470                 475                 480

Pro Ala Glu Asp Val Asp Thr Pro Arg Lys Lys Arg Lys His
                485                 490                 495

Arg Leu Trp Ala Ala His Cys Arg Lys Ile Gln Leu Lys Lys Asp Gly
            500                 505                 510

Ser Ser Asn His Val Tyr Asn Tyr Gln Pro Cys Asp His Pro Arg Gln
        515                 520                 525

Pro Cys Asp Ser Ser Cys Pro Cys Val Ile Ala Gln Asn Phe Cys Glu
    530                 535                 540

Lys Phe Cys Gln Cys Ser Ser Glu Cys Gln Asn Arg Phe Pro Gly Cys
545                 550                 555                 560

Arg Cys Lys Ala Gln Cys Asn Thr Lys Gln Cys Pro Cys Tyr Leu Ala
                565                 570                 575

Val Arg Glu Cys Asp Pro Asp Leu Cys Leu Thr Cys Gly Ala Ala Asp
            580                 585                 590

His Trp Asp Ser Lys Asn Val Ser Cys Lys Asn Cys Ser Ile Gln Arg
        595                 600                 605

Gly Ser Lys Lys His Leu Leu Leu Ala Pro Ser Asp Val Ala Gly Trp
    610                 615                 620

Gly Ile Phe Ile Lys Asp Pro Val Gln Lys Asn Glu Phe Ile Ser Glu
625                 630                 635                 640

Xaa Cys Gly Glu Ile Ile Ser Gln Asp Glu Ala Asp Arg Arg Gly Lys
                645                 650                 655

Val Tyr Asp Lys Tyr Met Cys Ser Phe Leu Phe Asn Leu Asn Asn Asp
            660                 665                 670

Phe Val Val Asp Ala Thr Arg Lys Gly Asn Lys Ile Arg Phe Ala Asn
```

```
              675                 680                 685
His Ser Val Asn Pro Asn Cys Tyr Ala Lys Val Met Met Val Asn Gly
    690                 695                 700

Asp His Arg Ile Gly Ile Phe Ala Lys Arg Ala Ile Gln Thr Gly Glu
705                 710                 715                 720

Glu Leu Phe Phe Asp Tyr Arg Tyr Ser Gln Ala Asp Ala Leu Lys Tyr
                725                 730                 735

Val Gly Ile Glu Arg Glu Met Glu Ile Pro
                740                 745

<210> SEQ ID NO 9
<211> LENGTH: 746
<212> TYPE: PRT
<213> ORGANISM: Homo sapiens

<400> SEQUENCE: 9

Met Gly Gln Thr Gly Lys Lys Ser Glu Lys Gly Pro Val Cys Trp Arg
1               5                   10                  15

Lys Arg Val Lys Ser Glu Tyr Met Arg Leu Arg Gln Leu Lys Arg Phe
            20                  25                  30

Arg Arg Ala Asp Glu Val Lys Ser Met Phe Ser Ser Asn Arg Gln Lys
        35                  40                  45

Ile Leu Glu Arg Thr Glu Ile Leu Asn Gln Glu Trp Lys Gln Arg Arg
    50                  55                  60

Ile Gln Pro Val His Ile Leu Thr Ser Val Ser Ser Leu Arg Gly Thr
65              70                  75                  80

Arg Glu Cys Ser Val Thr Ser Asp Leu Asp Phe Pro Thr Gln Val Ile
                85                  90                  95

Pro Leu Lys Thr Leu Asn Ala Val Ala Ser Val Pro Ile Met Tyr Ser
            100                 105                 110

Trp Ser Pro Leu Gln Gln Asn Phe Met Val Glu Asp Glu Thr Val Leu
        115                 120                 125

His Asn Ile Pro Tyr Met Gly Asp Glu Val Leu Asp Gln Asp Gly Thr
    130                 135                 140

Phe Ile Glu Glu Leu Ile Lys Asn Tyr Asp Gly Lys Val His Gly Asp
145             150                 155                 160

Arg Glu Cys Gly Phe Ile Asn Asp Glu Ile Phe Val Glu Leu Val Asn
                165                 170                 175

Ala Leu Gly Gln Tyr Asn Asp Asp Asp Asp Asp Gly Asp Asp
            180                 185                 190

Pro Glu Glu Arg Glu Glu Lys Gln Lys Asp Leu Glu Asp His Arg Asp
        195                 200                 205

Asp Lys Glu Ser Arg Pro Pro Arg Lys Phe Pro Ser Asp Lys Ile Phe
    210                 215                 220

Glu Ala Ile Ser Ser Met Phe Pro Asp Lys Gly Thr Ala Glu Glu Leu
225             230                 235                 240

Lys Glu Lys Tyr Lys Glu Leu Thr Glu Gln Gln Leu Pro Gly Ala Leu
                245                 250                 255

Pro Pro Glu Cys Thr Pro Asn Ile Asp Gly Pro Asn Ala Lys Ser Val
            260                 265                 270

Gln Arg Glu Gln Ser Leu His Ser Phe His Thr Leu Phe Cys Arg Arg
        275                 280                 285

Cys Phe Lys Tyr Asp Cys Phe Leu His Pro Phe His Ala Thr Pro Asn
    290                 295                 300
```

-continued

Thr Tyr Lys Arg Lys Asn Thr Glu Thr Ala Leu Asp Asn Lys Pro Cys
305                 310                 315                 320

Gly Pro Gln Cys Tyr Gln His Leu Glu Gly Ala Lys Glu Phe Ala Ala
            325                 330                 335

Ala Leu Thr Ala Glu Arg Ile Lys Thr Pro Lys Arg Pro Gly Gly
        340                 345                 350

Arg Arg Arg Gly Arg Leu Pro Asn Asn Ser Ser Arg Pro Ser Thr Pro
        355                 360                 365

Thr Ile Asn Val Leu Glu Ser Lys Asp Thr Asp Ser Asp Arg Glu Ala
370                 375                 380

Gly Thr Glu Thr Gly Gly Glu Asn Asn Asp Lys Glu Glu Glu Glu Lys
385                 390                 395                 400

Lys Asp Glu Thr Ser Ser Ser Glu Ala Asn Ser Arg Cys Gln Thr
            405                 410                 415

Pro Ile Lys Met Lys Pro Asn Ile Glu Pro Pro Glu Asn Val Glu Trp
            420                 425                 430

Ser Gly Ala Glu Ala Ser Met Phe Arg Val Leu Ile Gly Thr Tyr Tyr
        435                 440                 445

Asp Asn Phe Cys Ala Ile Ala Arg Leu Ile Gly Thr Lys Thr Cys Arg
450                 455                 460

Gln Val Tyr Glu Phe Arg Val Lys Glu Ser Ser Ile Ile Ala Pro Ala
465                 470                 475                 480

Pro Ala Glu Asp Val Asp Thr Pro Pro Arg Lys Lys Lys Arg Lys His
            485                 490                 495

Arg Leu Trp Ala Ala His Cys Arg Lys Ile Gln Leu Lys Lys Asp Gly
        500                 505                 510

Ser Ser Asn His Val Tyr Asn Tyr Gln Pro Cys Asp His Pro Arg Gln
        515                 520                 525

Pro Cys Asp Ser Ser Cys Pro Cys Val Ile Ala Gln Asn Phe Cys Glu
530                 535                 540

Lys Phe Cys Gln Cys Ser Ser Glu Cys Gln Asn Arg Phe Pro Gly Cys
545                 550                 555                 560

Arg Cys Lys Ala Gln Cys Asn Thr Lys Gln Cys Pro Cys Tyr Leu Ala
            565                 570                 575

Val Arg Glu Cys Asp Pro Asp Leu Cys Leu Thr Cys Gly Ala Ala Asp
        580                 585                 590

His Trp Asp Ser Lys Asn Val Ser Cys Lys Asn Cys Ser Ile Gln Arg
        595                 600                 605

Gly Ser Lys Lys His Leu Leu Leu Ala Pro Ser Asp Val Ala Gly Trp
610                 615                 620

Gly Ile Phe Ile Lys Asp Pro Val Gln Lys Asn Glu Phe Ile Ser Glu
625                 630                 635                 640

Phe Cys Gly Glu Ile Ile Ser Gln Asp Glu Ala Asp Arg Arg Gly Lys
            645                 650                 655

Val Tyr Asp Lys Tyr Met Cys Ser Phe Leu Phe Asn Leu Asn Asn Asp
        660                 665                 670

Phe Val Val Asp Ala Thr Arg Lys Gly Asn Lys Ile Arg Phe Ala Asn
        675                 680                 685

His Ser Val Asn Pro Asn Cys Tyr Ala Lys Val Met Met Val Asn Gly
        690                 695                 700

Asp His Arg Ile Gly Ile Phe Ala Lys Arg Ala Ile Gln Thr Gly Glu
705                 710                 715                 720

Glu Leu Phe Phe Asp Tyr Arg Tyr Ser Gln Ala Asp Ala Leu Lys Tyr

-continued

```
                725                 730                 735
Val Gly Ile Glu Arg Glu Met Glu Ile Pro
            740                 745

<210> SEQ ID NO 10
<211> LENGTH: 746
<212> TYPE: PRT
<213> ORGANISM: Homo sapiens

<400> SEQUENCE: 10

Met Gly Gln Thr Gly Lys Lys Ser Glu Lys Gly Pro Val Cys Trp Arg
1               5                   10                  15

Lys Arg Val Lys Ser Glu Tyr Met Arg Leu Arg Gln Leu Lys Arg Phe
            20                  25                  30

Arg Arg Ala Asp Glu Val Lys Ser Met Phe Ser Ser Asn Arg Gln Lys
        35                  40                  45

Ile Leu Glu Arg Thr Glu Ile Leu Asn Gln Glu Trp Lys Gln Arg Arg
    50                  55                  60

Ile Gln Pro Val His Ile Leu Thr Ser Val Ser Ser Leu Arg Gly Thr
65                  70                  75                  80

Arg Glu Cys Ser Val Thr Ser Asp Leu Asp Phe Pro Thr Gln Val Ile
                85                  90                  95

Pro Leu Lys Thr Leu Asn Ala Val Ala Ser Val Pro Ile Met Tyr Ser
            100                 105                 110

Trp Ser Pro Leu Gln Gln Asn Phe Met Val Glu Asp Glu Thr Val Leu
        115                 120                 125

His Asn Ile Pro Tyr Met Gly Asp Glu Val Leu Asp Gln Asp Gly Thr
    130                 135                 140

Phe Ile Glu Glu Leu Ile Lys Asn Tyr Asp Gly Lys Val His Gly Asp
145                 150                 155                 160

Arg Glu Cys Gly Phe Ile Asn Asp Glu Ile Phe Val Glu Leu Val Asn
                165                 170                 175

Ala Leu Gly Gln Tyr Asn Asp Asp Asp Asp Asp Gly Asp Asp
            180                 185                 190

Pro Glu Glu Arg Glu Glu Lys Gln Lys Asp Leu Glu Asp His Arg Asp
        195                 200                 205

Asp Lys Glu Ser Arg Pro Pro Arg Lys Phe Pro Ser Asp Lys Ile Phe
    210                 215                 220

Glu Ala Ile Ser Ser Met Phe Pro Asp Lys Gly Thr Ala Glu Glu Leu
225                 230                 235                 240

Lys Glu Lys Tyr Lys Glu Leu Thr Glu Gln Gln Leu Pro Gly Ala Leu
                245                 250                 255

Pro Pro Glu Cys Thr Pro Asn Ile Asp Gly Pro Asn Ala Lys Ser Val
            260                 265                 270

Gln Arg Glu Gln Ser Leu His Ser Phe His Thr Leu Phe Cys Arg Arg
        275                 280                 285

Cys Phe Lys Tyr Asp Cys Phe Leu His Pro Phe His Ala Thr Pro Asn
    290                 295                 300

Thr Tyr Lys Arg Lys Asn Thr Glu Thr Ala Leu Asp Asn Lys Pro Cys
305                 310                 315                 320

Gly Pro Gln Cys Tyr Gln His Leu Glu Gly Ala Lys Glu Phe Ala Ala
                325                 330                 335

Ala Leu Thr Ala Glu Arg Ile Lys Thr Pro Pro Lys Arg Pro Gly Gly
            340                 345                 350
```

Arg Arg Arg Gly Arg Leu Pro Asn Asn Ser Ser Arg Pro Ser Thr Pro
        355                 360                 365

Thr Ile Asn Val Leu Glu Ser Lys Asp Thr Asp Ser Asp Arg Glu Ala
370                 375                 380

Gly Thr Glu Thr Gly Gly Glu Asn Asn Asp Lys Glu Glu Glu Glu Lys
385                 390                 395                 400

Lys Asp Glu Thr Ser Ser Ser Glu Ala Asn Ser Arg Cys Gln Thr
                405                 410                 415

Pro Ile Lys Met Lys Pro Asn Ile Glu Pro Pro Glu Asn Val Glu Trp
                420                 425                 430

Ser Gly Ala Glu Ala Ser Met Phe Arg Val Leu Ile Gly Thr Tyr Tyr
        435                 440                 445

Asp Asn Phe Cys Ala Ile Ala Arg Leu Ile Gly Thr Lys Thr Cys Arg
        450                 455                 460

Gln Val Tyr Glu Phe Arg Val Lys Glu Ser Ser Ile Ile Ala Pro Ala
465                 470                 475                 480

Pro Ala Glu Asp Val Asp Thr Pro Pro Arg Lys Lys Arg Lys His
                485                 490                 495

Arg Leu Trp Ala Ala His Cys Arg Lys Ile Gln Leu Lys Lys Asp Gly
        500                 505                 510

Ser Ser Asn His Val Tyr Asn Tyr Gln Pro Cys Asp His Pro Arg Gln
        515                 520                 525

Pro Cys Asp Ser Ser Cys Pro Cys Val Ile Ala Gln Asn Phe Cys Glu
        530                 535                 540

Lys Phe Cys Gln Cys Ser Ser Glu Cys Gln Asn Arg Phe Pro Gly Cys
545                 550                 555                 560

Arg Cys Lys Ala Gln Cys Asn Thr Lys Gln Cys Pro Cys Tyr Leu Ala
                565                 570                 575

Val Arg Glu Cys Asp Pro Asp Leu Cys Leu Thr Cys Gly Ala Ala Asp
                580                 585                 590

His Trp Asp Ser Lys Asn Val Ser Cys Lys Asn Cys Ser Ile Gln Arg
        595                 600                 605

Gly Ser Lys Lys His Leu Leu Leu Ala Pro Ser Asp Val Ala Gly Trp
610                 615                 620

Gly Ile Phe Ile Lys Asp Pro Val Gln Lys Asn Glu Phe Ile Ser Glu
625                 630                 635                 640

His Cys Gly Glu Ile Ile Ser Gln Asp Glu Ala Asp Arg Arg Gly Lys
                645                 650                 655

Val Tyr Asp Lys Tyr Met Cys Ser Phe Leu Phe Asn Leu Asn Asn Asp
                660                 665                 670

Phe Val Val Asp Ala Thr Arg Lys Gly Asn Lys Ile Arg Phe Ala Asn
        675                 680                 685

His Ser Val Asn Pro Asn Cys Tyr Ala Lys Val Met Met Val Asn Gly
        690                 695                 700

Asp His Arg Ile Gly Ile Phe Ala Lys Arg Ala Ile Gln Thr Gly Glu
705                 710                 715                 720

Glu Leu Phe Phe Asp Tyr Arg Tyr Ser Gln Ala Asp Ala Leu Lys Tyr
                725                 730                 735

Val Gly Ile Glu Arg Glu Met Glu Ile Pro
                740                 745

<210> SEQ ID NO 11
<211> LENGTH: 746
<212> TYPE: PRT

<213> ORGANISM: Homo sapiens

<400> SEQUENCE: 11

```
Met Gly Gln Thr Gly Lys Lys Ser Glu Lys Gly Pro Val Cys Trp Arg
1               5                   10                  15

Lys Arg Val Lys Ser Glu Tyr Met Arg Leu Arg Gln Leu Lys Arg Phe
            20                  25                  30

Arg Arg Ala Asp Glu Val Lys Ser Met Phe Ser Ser Asn Arg Gln Lys
        35                  40                  45

Ile Leu Glu Arg Thr Glu Ile Leu Asn Gln Glu Trp Lys Gln Arg Arg
50                  55                  60

Ile Gln Pro Val His Ile Leu Thr Ser Val Ser Ser Leu Arg Gly Thr
65                  70                  75                  80

Arg Glu Cys Ser Val Thr Ser Asp Leu Asp Phe Pro Thr Gln Val Ile
            85                  90                  95

Pro Leu Lys Thr Leu Asn Ala Val Ala Ser Val Pro Ile Met Tyr Ser
        100                 105                 110

Trp Ser Pro Leu Gln Gln Asn Phe Met Val Glu Asp Glu Thr Val Leu
    115                 120                 125

His Asn Ile Pro Tyr Met Gly Asp Glu Val Leu Asp Gln Asp Gly Thr
130                 135                 140

Phe Ile Glu Glu Leu Ile Lys Asn Tyr Asp Gly Lys Val His Gly Asp
145                 150                 155                 160

Arg Glu Cys Gly Phe Ile Asn Asp Glu Ile Phe Val Glu Leu Val Asn
            165                 170                 175

Ala Leu Gly Gln Tyr Asn Asp Asp Asp Asp Asp Gly Asp Asp
        180                 185                 190

Pro Glu Glu Arg Glu Glu Lys Gln Lys Asp Leu Glu Asp His Arg Asp
    195                 200                 205

Asp Lys Glu Ser Arg Pro Pro Arg Lys Phe Pro Ser Asp Lys Ile Phe
210                 215                 220

Glu Ala Ile Ser Ser Met Phe Pro Asp Lys Gly Thr Ala Glu Glu Leu
225                 230                 235                 240

Lys Glu Lys Tyr Lys Glu Leu Thr Glu Gln Gln Leu Pro Gly Ala Leu
            245                 250                 255

Pro Pro Glu Cys Thr Pro Asn Ile Asp Gly Pro Asn Ala Lys Ser Val
        260                 265                 270

Gln Arg Glu Gln Ser Leu His Ser Phe His Thr Leu Phe Cys Arg Arg
    275                 280                 285

Cys Phe Lys Tyr Asp Cys Phe Leu His Pro Phe His Ala Thr Pro Asn
290                 295                 300

Thr Tyr Lys Arg Lys Asn Thr Glu Thr Ala Leu Asp Asn Lys Pro Cys
305                 310                 315                 320

Gly Pro Gln Cys Tyr Gln His Leu Glu Gly Ala Lys Glu Phe Ala Ala
            325                 330                 335

Ala Leu Thr Ala Glu Arg Ile Lys Thr Pro Pro Lys Arg Pro Gly Gly
        340                 345                 350

Arg Arg Arg Gly Arg Leu Pro Asn Asn Ser Ser Arg Pro Ser Thr Pro
    355                 360                 365

Thr Ile Asn Val Leu Glu Ser Lys Asp Thr Asp Ser Asp Arg Glu Ala
370                 375                 380

Gly Thr Glu Thr Gly Gly Glu Asn Asn Asp Lys Glu Glu Glu Glu Lys
385                 390                 395                 400
```

```
Lys Asp Glu Thr Ser Ser Ser Glu Ala Asn Ser Arg Cys Gln Thr
                405                 410                 415

Pro Ile Lys Met Lys Pro Asn Ile Glu Pro Pro Glu Asn Val Glu Trp
        420                 425                 430

Ser Gly Ala Glu Ala Ser Met Phe Arg Val Leu Ile Gly Thr Tyr Tyr
            435                 440                 445

Asp Asn Phe Cys Ala Ile Ala Arg Leu Ile Gly Thr Lys Thr Cys Arg
450                 455                 460

Gln Val Tyr Glu Phe Arg Val Lys Glu Ser Ser Ile Ile Ala Pro Ala
465                 470                 475                 480

Pro Ala Glu Asp Val Asp Thr Pro Pro Arg Lys Lys Arg Lys His
                485                 490                 495

Arg Leu Trp Ala Ala His Cys Arg Lys Ile Gln Leu Lys Lys Asp Gly
        500                 505                 510

Ser Ser Asn His Val Tyr Asn Tyr Gln Pro Cys Asp His Pro Arg Gln
            515                 520                 525

Pro Cys Asp Ser Ser Cys Pro Cys Val Ile Ala Gln Asn Phe Cys Glu
530                 535                 540

Lys Phe Cys Gln Cys Ser Ser Glu Cys Gln Asn Arg Phe Pro Gly Cys
545                 550                 555                 560

Arg Cys Lys Ala Gln Cys Asn Thr Lys Gln Cys Pro Cys Tyr Leu Ala
                565                 570                 575

Val Arg Glu Cys Asp Pro Asp Leu Cys Leu Thr Cys Gly Ala Ala Asp
            580                 585                 590

His Trp Asp Ser Lys Asn Val Ser Cys Lys Asn Cys Ser Ile Gln Arg
        595                 600                 605

Gly Ser Lys Lys His Leu Leu Leu Ala Pro Ser Asp Val Ala Gly Trp
    610                 615                 620

Gly Ile Phe Ile Lys Asp Pro Val Gln Lys Asn Glu Phe Ile Ser Glu
625                 630                 635                 640

Asn Cys Gly Glu Ile Ile Ser Gln Asp Glu Ala Asp Arg Arg Gly Lys
                645                 650                 655

Val Tyr Asp Lys Tyr Met Cys Ser Phe Leu Phe Asn Leu Asn Asn Asp
            660                 665                 670

Phe Val Val Asp Ala Thr Arg Lys Gly Asn Lys Ile Arg Phe Ala Asn
        675                 680                 685

His Ser Val Asn Pro Asn Cys Tyr Ala Lys Val Met Met Val Asn Gly
    690                 695                 700

Asp His Arg Ile Gly Ile Phe Ala Lys Arg Ala Ile Gln Thr Gly Glu
705                 710                 715                 720

Glu Leu Phe Phe Asp Tyr Arg Tyr Ser Gln Ala Asp Ala Leu Lys Tyr
                725                 730                 735

Val Gly Ile Glu Arg Glu Met Glu Ile Pro
            740                 745

<210> SEQ ID NO 12
<211> LENGTH: 746
<212> TYPE: PRT
<213> ORGANISM: Homo sapiens

<400> SEQUENCE: 12

Met Gly Gln Thr Gly Lys Lys Ser Glu Lys Gly Pro Val Cys Trp Arg
1               5                   10                  15

Lys Arg Val Lys Ser Glu Tyr Met Arg Leu Arg Gln Leu Lys Arg Phe
            20                  25                  30
```

```
Arg Arg Ala Asp Glu Val Lys Ser Met Phe Ser Ser Asn Arg Gln Lys
        35                  40                  45

Ile Leu Glu Arg Thr Glu Ile Leu Asn Gln Glu Trp Lys Gln Arg Arg
    50                  55                  60

Ile Gln Pro Val His Ile Leu Thr Ser Val Ser Ser Leu Arg Gly Thr
65                  70                  75                  80

Arg Glu Cys Ser Val Thr Ser Asp Leu Asp Phe Pro Thr Gln Val Ile
                85                  90                  95

Pro Leu Lys Thr Leu Asn Ala Val Ala Ser Val Pro Ile Met Tyr Ser
                100                 105                 110

Trp Ser Pro Leu Gln Gln Asn Phe Met Val Glu Asp Glu Thr Val Leu
            115                 120                 125

His Asn Ile Pro Tyr Met Gly Asp Glu Val Leu Asp Gln Asp Gly Thr
        130                 135                 140

Phe Ile Glu Glu Leu Ile Lys Asn Tyr Asp Gly Lys Val His Gly Asp
145                 150                 155                 160

Arg Glu Cys Gly Phe Ile Asn Asp Glu Ile Phe Val Glu Leu Val Asn
                165                 170                 175

Ala Leu Gly Gln Tyr Asn Asp Asp Asp Asp Asp Asp Gly Asp Asp
                180                 185                 190

Pro Glu Glu Arg Glu Glu Lys Gln Lys Asp Leu Glu Asp His Arg Asp
            195                 200                 205

Asp Lys Glu Ser Arg Pro Pro Arg Lys Phe Pro Ser Asp Lys Ile Phe
        210                 215                 220

Glu Ala Ile Ser Ser Met Phe Pro Asp Lys Gly Thr Ala Glu Glu Leu
225                 230                 235                 240

Lys Glu Lys Tyr Lys Glu Leu Thr Glu Gln Gln Leu Pro Gly Ala Leu
                245                 250                 255

Pro Pro Glu Cys Thr Pro Asn Ile Asp Gly Pro Asn Ala Lys Ser Val
            260                 265                 270

Gln Arg Glu Gln Ser Leu His Ser Phe His Thr Leu Phe Cys Arg Arg
        275                 280                 285

Cys Phe Lys Tyr Asp Cys Phe Leu His Pro Phe His Ala Thr Pro Asn
        290                 295                 300

Thr Tyr Lys Arg Lys Asn Thr Glu Thr Ala Leu Asp Asn Lys Pro Cys
305                 310                 315                 320

Gly Pro Gln Cys Tyr Gln His Leu Glu Gly Ala Lys Glu Phe Ala Ala
                325                 330                 335

Ala Leu Thr Ala Glu Arg Ile Lys Thr Pro Pro Lys Arg Pro Gly Gly
            340                 345                 350

Arg Arg Arg Gly Arg Leu Pro Asn Asn Ser Ser Arg Pro Ser Thr Pro
        355                 360                 365

Thr Ile Asn Val Leu Glu Ser Lys Asp Thr Asp Ser Asp Arg Glu Ala
        370                 375                 380

Gly Thr Glu Thr Gly Gly Glu Asn Asn Asp Lys Glu Glu Glu Glu Lys
385                 390                 395                 400

Lys Asp Glu Thr Ser Ser Ser Ser Glu Ala Asn Ser Arg Cys Gln Thr
                405                 410                 415

Pro Ile Lys Met Lys Pro Asn Ile Glu Pro Pro Glu Asn Val Glu Trp
            420                 425                 430

Ser Gly Ala Glu Ala Ser Met Phe Arg Val Leu Ile Gly Thr Tyr Tyr
            435                 440                 445
```

Asp Asn Phe Cys Ala Ile Ala Arg Leu Ile Gly Thr Lys Thr Cys Arg
            450                 455                 460

Gln Val Tyr Glu Phe Arg Val Lys Glu Ser Ser Ile Ile Ala Pro Ala
465                 470                 475                 480

Pro Ala Glu Asp Val Asp Thr Pro Pro Arg Lys Lys Arg Lys His
                485                 490                 495

Arg Leu Trp Ala Ala His Cys Arg Lys Ile Gln Leu Lys Lys Asp Gly
            500                 505                 510

Ser Ser Asn His Val Tyr Asn Tyr Gln Pro Cys Asp His Pro Arg Gln
            515                 520                 525

Pro Cys Asp Ser Ser Cys Pro Cys Val Ile Ala Gln Asn Phe Cys Glu
            530                 535                 540

Lys Phe Cys Gln Cys Ser Ser Glu Cys Gln Asn Arg Phe Pro Gly Cys
545                 550                 555                 560

Arg Cys Lys Ala Gln Cys Asn Thr Lys Gln Cys Pro Cys Tyr Leu Ala
            565                 570                 575

Val Arg Glu Cys Asp Pro Asp Leu Cys Leu Thr Cys Gly Ala Ala Asp
            580                 585                 590

His Trp Asp Ser Lys Asn Val Ser Cys Lys Asn Cys Ser Ile Gln Arg
            595                 600                 605

Gly Ser Lys Lys His Leu Leu Leu Ala Pro Ser Asp Val Ala Gly Trp
            610                 615                 620

Gly Ile Phe Ile Lys Asp Pro Val Gln Lys Asn Glu Phe Ile Ser Glu
625                 630                 635                 640

Ser Cys Gly Glu Ile Ile Ser Gln Asp Glu Ala Asp Arg Arg Gly Lys
            645                 650                 655

Val Tyr Asp Lys Tyr Met Cys Ser Phe Leu Phe Asn Leu Asn Asn Asp
            660                 665                 670

Phe Val Val Asp Ala Thr Arg Lys Gly Asn Lys Ile Arg Phe Ala Asn
            675                 680                 685

His Ser Val Asn Pro Asn Cys Tyr Ala Lys Val Met Met Val Asn Gly
            690                 695                 700

Asp His Arg Ile Gly Ile Phe Ala Lys Arg Ala Ile Gln Thr Gly Glu
705                 710                 715                 720

Glu Leu Phe Phe Asp Tyr Arg Tyr Ser Gln Ala Asp Ala Leu Lys Tyr
            725                 730                 735

Val Gly Ile Glu Arg Glu Met Glu Ile Pro
            740                 745

<210> SEQ ID NO 13
<211> LENGTH: 24
<212> TYPE: PRT
<213> ORGANISM: Homo sapiens

<400> SEQUENCE: 13

Leu Ala Thr Lys Ala Ala Arg Lys Ser Ala Pro Ala Thr Gly Gly Val
1               5                   10                  15

Lys Lys Pro His Arg Tyr Arg Pro
            20